United States Patent
Holsten et al.

(10) Patent No.: US 7,588,174 B2
(45) Date of Patent: *Sep. 15, 2009

(54) SURGICAL STAPLING INSTRUMENTS INCLUDING A CARTRIDGE HAVING MULTIPLE STAPLES SIZES

(75) Inventors: Henry E. Holsten, Covington, GA (US); Frank J. Viola, Sandy Hook, CT (US); Clifford L. Emmons, Oakville, CT (US); John W. Beardsley, Wallingford, CT (US); Russell Heinrich, Madison, CT (US); Nicola Cullinan, Bethal, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/178,739

(22) Filed: Jul. 24, 2008

(65) Prior Publication Data

US 2009/0026245 A1    Jan. 29, 2009

Related U.S. Application Data

(60) Division of application No. 11/974,637, filed on Oct. 15, 2007, now Pat. No. 7,455,676, which is a continuation of application No. 11/592,566, filed on Nov. 3, 2006, now Pat. No. 7,398,908, which is a continuation-in-part of application No. 11/436,222, filed on May 18, 2006, now Pat. No. 7,401,721, which is a continuation-in-part of application No. 11/204,060, filed on Aug. 15, 2005, now Pat. No. 7,407,075.

(51) Int. Cl.
  *A61B 17/068* (2006.01)

(52) U.S. Cl. .................. 227/176.1; 227/19; 227/180.1

(58) Field of Classification Search ............... 227/19, 227/178.1, 176.1, 180.1, 175.1, 179.1; 606/139, 606/219
See application file for complete search history.

(56) References Cited

U.S. PATENT DOCUMENTS

| 3,499,591 | A | 3/1970 | Green |
| 3,771,526 | A | 11/1973 | Rudie |
| 4,319,576 | A | 3/1982 | Rothfuss |
| 4,429,695 | A | 2/1984 | Green |
| 4,605,001 | A | 8/1986 | Rothfuss et al. |

(Continued)

FOREIGN PATENT DOCUMENTS

EP    0878169    11/1998

(Continued)

OTHER PUBLICATIONS

European Search Report for EP 06016963.8-2318 date of completion is Mar. 9, 2007 (9 pages).

*Primary Examiner*—Scott A. Smith

(57) ABSTRACT

A surgical stapling apparatus includes a staple cartridge and an anvil member. The staple cartridge includes a plurality of surgical fasteners disposed in rows of retention slots. The staple cartridge may have an annular or linear configuration of retention slots. The tissue contacting surface of the staple cartridge may be tapered or stepped. The anvil member has a tissue contacting surface that includes a number of pockets arranged for substantially aligning with the retention slots. In addition, the tissue contacting surface of the anvil member may complement the tissue contacting surface of the staple cartridge.

48 Claims, 35 Drawing Sheets

U.S. PATENT DOCUMENTS

| | | | |
|---|---|---|---|
| 4,608,981 A | 9/1986 | Rothfuss et al. |
| 4,610,383 A | 9/1986 | Rothfuss et al. |
| 4,767,044 A | 8/1988 | Green |
| 4,809,695 A | 3/1989 | Gwathmey et al. |
| 4,848,637 A | 7/1989 | Pruitt |
| 4,930,503 A | 6/1990 | Pruitt |
| 4,941,623 A | 7/1990 | Pruitt |
| 4,978,049 A | 12/1990 | Green |
| 5,027,834 A | 7/1991 | Pruitt |
| 5,180,092 A | 1/1993 | Crainich |
| 5,240,163 A | 8/1993 | Stein et al. |
| 5,342,396 A | 8/1994 | Cook |
| 5,452,836 A | 9/1995 | Huitema et al. |
| 5,452,837 A | 9/1995 | Williamson, IV et al. |
| 5,480,089 A | 1/1996 | Blewett |
| 5,484,095 A | 1/1996 | Green et al. |
| 5,497,931 A | 3/1996 | Nakamura |
| 5,571,116 A | 11/1996 | Bolanos et al. |
| 5,571,285 A | 11/1996 | Chow et al. |
| 5,667,526 A | 9/1997 | Levin |
| 5,676,674 A | 10/1997 | Bolanos et al. |
| 5,697,542 A | 12/1997 | Knodel et al. |
| 5,709,680 A | 1/1998 | Yates et al. |
| 5,865,361 A | 2/1999 | Milliman et al. |
| 5,871,135 A | 2/1999 | Williamson IV et al. |
| 5,915,616 A | 6/1999 | Viola et al. |
| 5,964,394 A | 10/1999 | Robertson |
| 6,202,914 B1 | 3/2001 | Geiste et al. |
| 6,325,810 B1 | 12/2001 | Hamilton et al. |
| 6,330,956 B1 | 12/2001 | Willinger |
| 6,503,259 B2 | 1/2003 | Huxel et al. |
| 6,669,073 B2 | 12/2003 | Milliman et al. |
| 6,786,382 B1 | 9/2004 | Hoffman |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,044,352 B2 | 5/2006 | Shelton, IV et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,114,642 B2 | 10/2006 | Whitman |
| 7,398,908 B2 * | 7/2008 | Holsten et al. ............ 227/176.1 |
| 7,401,721 B2 * | 7/2008 | Holsten et al. ............ 227/176.1 |
| 7,407,075 B2 * | 8/2008 | Holsten et al. ............ 227/175.1 |
| 7,455,676 B2 * | 11/2008 | Holsten et al. ............... 606/139 |
| 2004/0004105 A1 | 1/2004 | Jankowski |
| 2004/0232195 A1 | 11/2004 | Shelton, IV et al. |
| 2004/0232199 A1 | 11/2004 | Shelton, IV et al. |
| 2005/0006430 A1 | 1/2005 | Wales |
| 2005/0006431 A1 | 1/2005 | Shelton et al. |
| 2005/0006434 A1 | 1/2005 | Wales et al. |
| 2005/0023324 A1 | 2/2005 | Doll et al. |
| 2005/0070925 A1 | 3/2005 | Shelton et al. |
| 2005/0070958 A1 | 3/2005 | Swayze et al. |
| 2005/0173490 A1 | 8/2005 | Shelton, IV |
| 2005/0178813 A1 | 8/2005 | Swayze et al. |
| 2005/0187576 A1 | 8/2005 | Whitman et al. |
| 2005/0263562 A1 | 12/2005 | Shelton et al. |
| 2006/0000868 A1 | 1/2006 | Shelton et al. |
| 2006/0022014 A1 | 2/2006 | Shelton et al. |
| 2006/0022015 A1 | 2/2006 | Shelton et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0025816 A1 | 2/2006 | Shelton, IV |
| 2006/0025817 A1 | 2/2006 | Ortiz et al. |
| 2006/0049230 A1 | 3/2006 | Shelton et al. |
| 2006/0097026 A1 | 5/2006 | Shelton, IV |
| 2006/0226196 A1 | 10/2006 | Hueil et al. |
| 2007/0010838 A1 | 1/2007 | Shelton et al. |
| 2007/0045379 A1 | 3/2007 | Shelton |

FOREIGN PATENT DOCUMENTS

| | | |
|---|---|---|
| EP | 0640315 | 12/1998 |
| EP | 1090592 | 4/2001 |
| EP | 1316290 | 11/2002 |
| EP | 1479346 | 5/2004 |
| EP | 1728473 | 12/2006 |
| FR | 2838952 | 10/2003 |
| RU | 1442191 | 12/1998 |
| SU | 405234 | 9/1975 |
| SU | 1333319 | 8/1987 |
| SU | 1459659 | 2/1989 |
| WO | WO 90/05489 | 5/1990 |
| WO | WO 97/34533 | 9/1997 |
| WO | WO 03/094743 | 11/2003 |
| WO | WO 03/094747 | 11/2003 |

* cited by examiner

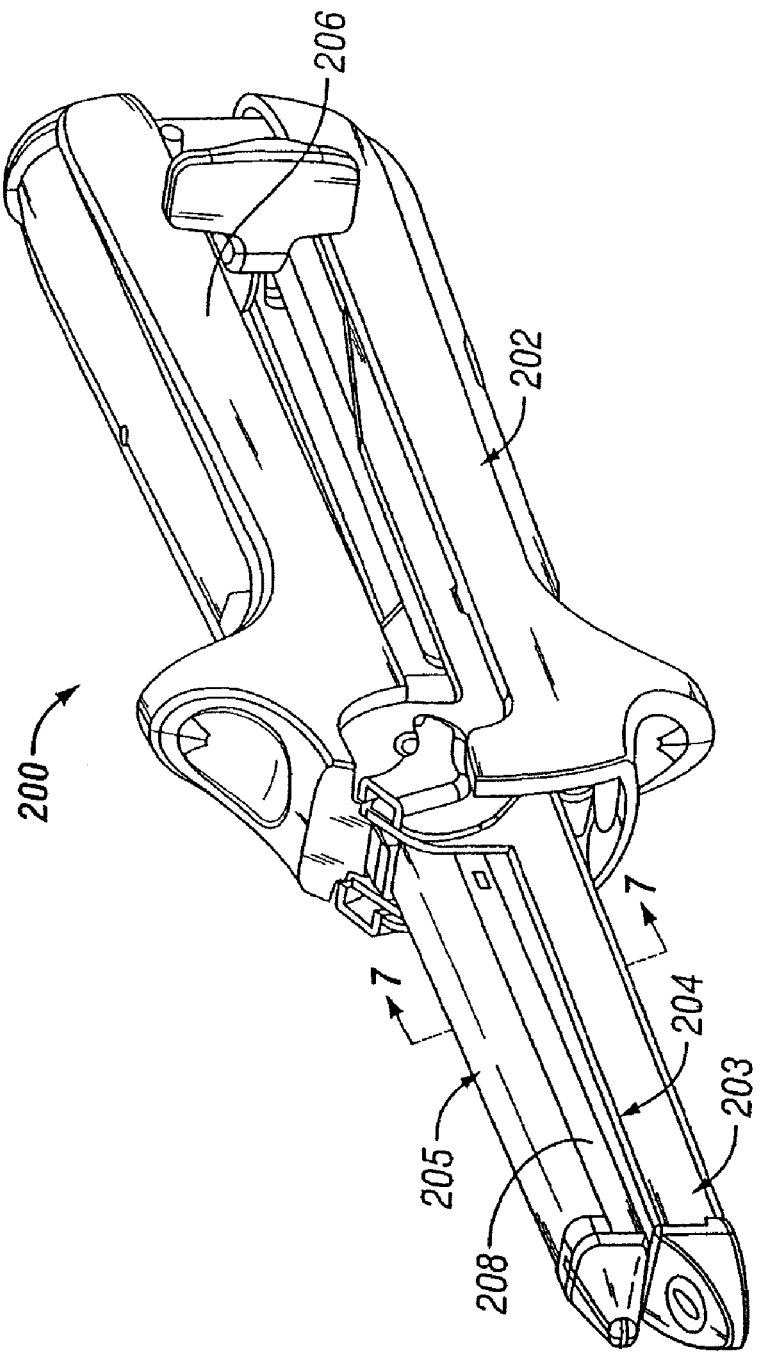

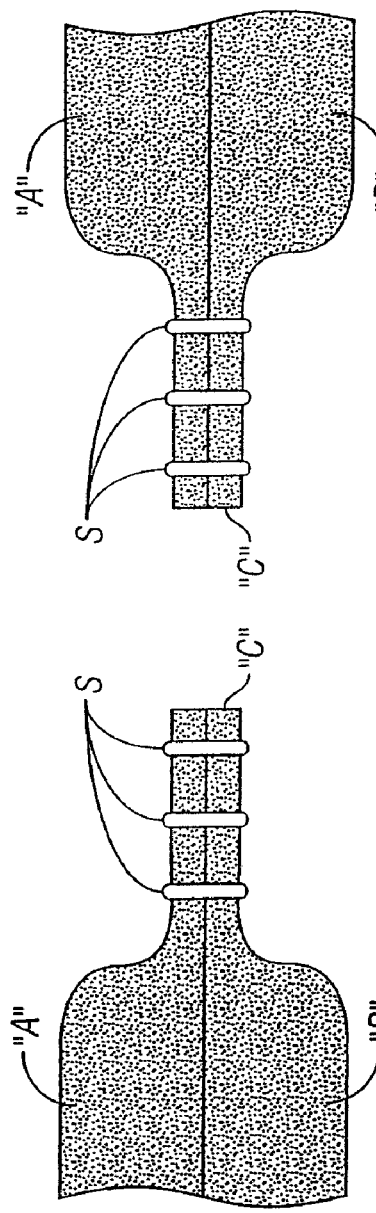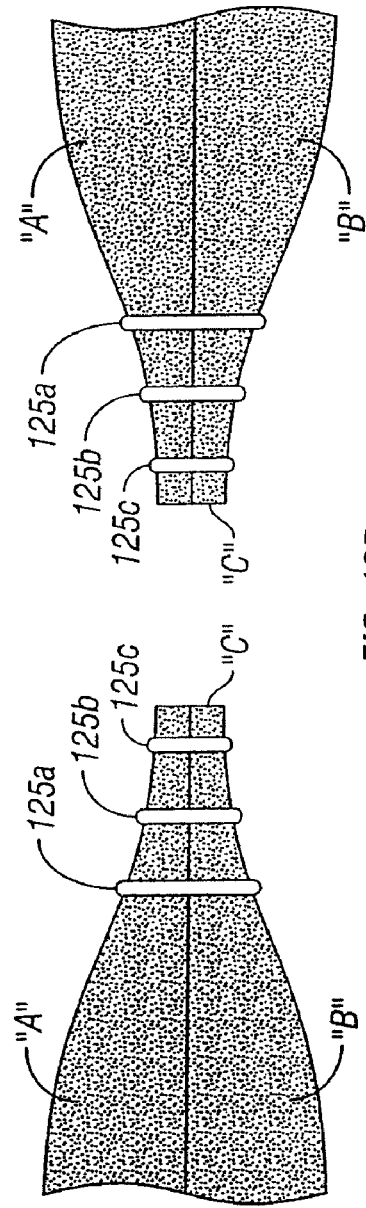
FIG. 16A (Prior Art)
FIG. 16B

SURGICAL STAPLING INSTRUMENTS INCLUDING A CARTRIDGE HAVING MULTIPLE STAPLES SIZES

CROSS REFERENCE TO RELATED APPLICATIONS

This application is a division of U.S. patent application Ser. No. 11/974,637 filed Oct. 15, 2007, now U.S. Pat. No. 7,455,676, which is a continuation of U.S. patent application Ser. No. 11/592,566 filed Nov. 3, 2006, now U.S. Pat. No. 7,398,908, which is a continuation-in-part of application Ser. No. 11/436,222 filed May 18, 2006, now U.S. Pat. No. 7,401,721, which is a continuation-in-part of application Ser. No. 11/204,060 filed Aug. 15, 2005 now U.S. Pat. No. 7,407,075. Each of these applications is incorporated herein in their entirety by this reference.

BACKGROUND

1. Technical Field

The present disclosure relates to surgical stapling instruments and, more particularly, to surgical stapling instruments including a cartridge having multiple staple sizes.

2. Background of Related Art

There are several known types of surgical stapling instruments specifically adapted for use in various procedures such as end-to-end anastomosis, gastrointestinal anastomosis, endoscopic gastrointestinal anastomosis, and transverse anastomosis. Examples of stapling instruments for these various procedures can be found in U.S. Pat. Nos. 5,915,616; 6,202,914; 5,865,361; and 5,964,394.

Each surgical stapling instrument includes an anvil which is approximated relative to a staple cartridge. The staple cartridge typically has one or more laterally spaced rows of staples which, depending on the particular stapling instrument, may be arranged in a linear or non-linear configuration. The anvil includes staple forming depressions which are aligned with and/or in registration with the staple slots of the staples in the cartridge. In use, each of the surgical stapling instruments involves the gripping of tissue to be fastened, the ejecting of individual staples, the forcing of staples through the gripped tissue and the closing and/or forming of the staples against the staple forming depressions of the anvil.

A common issue in transecting tissue and/or in anastomosis procedures, employing any one of the surgical stapling instruments disclosed above, is the balance between anastomotic strength and the degree of hemostasis achievable. It is known to include different size staples in a surgical stapling apparatus having a constant gap (i.e. a uniform distance) between an anvil and a staple cartridge.

SUMMARY

The present disclosure is directed towards surgical stapling instruments configured to effectuate an improved balance between the anastomotic strength and the degree of hemostasis at the tissue interface. In particular, embodiments of the present disclosure include surgical fasteners of different sizes. Further still, the distance between an anvil member and a staple cartridge (i.e. the gap) varies from a centerline of the staple cartridge to an outer edge of the staple cartridge. Preferably, the gap is greater at the outer edge of the cartridge in comparison to the gap at the centerline. This can be achieved by either varying the contour (i.e. profile) of the staple cartridge and/or the anvil member. Combining the different sizes of surgical fasteners with the varying gap between the anvil member and the staple cartridge improves the anastomotic strength and the degree of hemostasis at the tissue interface.

According to one aspect of the disclosure, the surgical stapling instrument includes a first structure defining having an anvil member operatively associated therewith, and a second structure defining a staple cartridge operatively associated therewith. The staple cartridge has a tissue contacting surface with a stepped cross-sectional profile. The tissue contacting surface of the staple cartridge also includes a plurality of retention slots formed therein for retaining a surgical fastener. During operation of the surgical stapling instrument, the anvil member and the staple cartridge can be approximated relative to one another.

The stepped tissue contact surface of the staple cartridge defines a plurality of tissue contacting surfaces each having a different height. In one embodiment, the stepped tissue contacting surface of the cartridge includes an inner tissue contacting surface having a height, an intermediate tissue contacting surface having a height less than the height of the inner tissue contacting surface, and an outer tissue contacting surface having a height less than the height of the intermediate tissue contacting surface.

The inner, intermediate, and outer tissue contacting surfaces each include at least one row of retention slots formed therein. A plurality of surgical fasteners is disposed, one each, in each retention slot. Each surgical fastener includes a backspan and a pair of descending legs.

The surgical fasteners retained in the retention slots formed in the inner tissue contacting surface have a first leg length, the surgical fasteners retained in the retention slots formed in the intermediate tissue contacting surface have a second leg length, and the surgical fasteners retained in the retention slots formed in the outer tissue contacting surface have a third leg length. In one embodiment, the surgical fasteners retained in the retention slots formed in the inner tissue contacting surface have a leg length of about 2.3 mm, while the surgical fasteners retained in the retention slots formed in the intermediate tissue contacting surface have a leg length of about 3.5 mm, and the surgical fasteners retained in the retention slots formed in the outer tissue contacting surface have a leg length of about 4.1 mm.

It is envisioned that the surgical stapling instrument can be a circular-type surgical stapling instrument wherein the anvil member and the staple cartridge can be annular. In one embodiment, the plurality of tissue contacting surfaces decreases in height in a radially outward direction. Accordingly, the inner tissue contacting surface is closest to the center and the outer tissue contacting surface is furthest from the center of the annular staple cartridge. Moreover, surgical fasteners having relatively short leg lengths are retained in the retention slots closest to the center of the annular staple cartridge while surgical fasteners having relatively longer leg lengths are retained in the retention slots furthest from the center of the annular staple cartridge.

It is further envisioned that the surgical stapling instrument can be a linear-type surgical stapling instrument wherein the anvil member and the staple cartridge are linear. In these instruments, the staple cartridge and/or the anvil member may define a knife cut line. Accordingly, the plurality of tissue contacting surfaces decreases in height in a direction orthogonally outward from the knife cut line. In particular, the inner tissue contacting surface is closest to the knife cut line while the outer tissue contacting surface is furthest from the knife cut line. In addition, surgical fasteners having relatively short leg lengths are retained in the retention slots closest to the knife cut line while surgical fasteners having relatively longer leg lengths are retained in the retention slots furthest from the knife cut line.

It is envisioned that the anvil member can have a tissue contacting surface with a stepped cross-sectional profile including a plurality of tissue contacting surfaces, wherein each tissue contacting surface has a different height. In addition, each one of the plurality of tissue contacting surfaces can include at least one annular and/or linear row of surgical fastener forming depressions formed therein.

In one embodiment, the anvil member can have a tissue contacting surface which is shaped (i.e. stepped) to complement the stepped tissue contacting surface of the staple cartridge. In another embodiment, the anvil member can have a tissue contacting surface which is stepped while the tissue contacting surface of the staple cartridge is substantially planar. In yet another embodiment, the anvil member can have a tissue contacting surface which is shaped to substantially complement the stepped tissue contacting surface of the staple cartridge (i.e. the depths of the tissue contacting surfaces of the stepped anvil member are not equal to the heights of the individual tissue contacting surfaces of the tissue contacting surface of the staple cartridge). In still another embodiment, the anvil member can have a tissue contacting surface which is stepped to mirror the tissue contacting surface of the staple cartridge (i.e. the depths of individual tissue contacting surfaces of the tissue contacting surface of the anvil member are substantially equal to the depths of the individual tissue contacting surfaces of the staple cartridge).

In other embodiments of the present disclosure, a surgical stapling instrument includes an operative tool disposed at one end thereof. The operative tool includes an anvil member and a staple cartridge. The staple cartridge may be included in a disposable surgical stapling apparatus or in a reusable surgical stapling apparatus. Further still, a replaceable loading unit may be located in either the disposable or the reusable surgical stapling apparatus. In one embodiment, the replaceable loading unit includes a staple cartridge, while an alternate embodiment of the replaceable loading unit includes a staple cartridge and an anvil member. In particular, the staple cartridge includes a plurality of surgical fasteners disposed in rows of retention slots. The surgical fasteners may have different leg lengths wherein a plurality of surgical fasteners having substantially the same leg length is disposed in a row. A number of fastener ejection members are disposed in the staple cartridge wherein each fastener ejection member includes a plurality of staple pushers for ejecting the surgical fasteners in cooperation with an actuation mechanism. The staple pushers of the fastener ejection member each have a shape that generally corresponds to the shape of the staple pockets of the anvil member and the retention slots of the staple cartridge.

The staple cartridge may include an angled tissue contacting surface that peaks at a centerline of the staple cartridge and tapers towards outer walls of the staple cartridge. Alternatively, the tissue contacting surface of the staple cartridge may have a surface that is parallel with the bottom surface of the staple cartridge or parallel to a plane defined by the backspans of surgical fasteners disposed in a selected row. The parallel surface of the tissue contacting surface has a width dimension that is sufficient to accommodate at least one row of surgical fasteners. The staple cartridge may include a knife channel.

In cooperation with the presently disclosed staple cartridge, the anvil member may include a planar tissue contacting surface that is substantially parallel to the bottom surface of the staple cartridge or parallel to a plane defined by the backspans of surgical fasteners disposed in a selected row. In the alternatives the tissue contacting surface of the anvil member may be angled in an opposed manner to the angle of the tissue contacting surface of the staple cartridge. Further still, the tissue contacting surface of the anvil member may have a planar surface that is substantially parallel to the bottom surface of the staple cartridge or parallel to a plane defined by the backspans of surgical fasteners disposed in a selected row and tapered surfaces that define angles opposite to the angles defined by the tissue contacting surface of the staple cartridge. The parallel surfaces of the anvil member have a width dimension that corresponds to a width dimension of the parallel surface of the staple cartridge.

It is further contemplated that one embodiment of the surgical stapling apparatus includes structures for supplemental sealing of the fastened layers of tissue. In one embodiment, the surgical stapling apparatus includes a wound closure assembly having a reservoir and a supply line. The reservoir is adapted for storing a quantity of a wound closure material and is fluidly coupled to the staple cartridge via the supply line for delivering amounts of the wound closure material to the plurality of retention slots.

In yet another embodiment of the presently disclosed surgical stapling apparatus, the staple cartridge may include a planar surface proximate a centerline of the staple cartridge and an arcuate surface adjacent to the planar surface. The arcuate surface extends outwards from the centerline and downwards towards the base of the staple cartridge defining a concave configuration with respect to the base of the staple cartridge. Each of the surfaces includes at least one row of retention slots and defines a tissue contacting surface. In addition, this embodiment of the staple cartridge includes a plurality fastener ejection members and a plurality of surgical fasteners. Tips of the unfired surgical fasteners may be positioned beneath the arcuate and planar surfaces or may extend into the retention slots wherein the tips are substantially flush with the tissue contacting surface. This embodiment of the staple cartridge may be combined with an anvil member having a planar tissue contacting surface that cooperates with the tissue contacting surface of the staple cartridge to position layers of tissue therebetween and form completed surgical fasteners. Alternatively, an anvil member may have a planar surface corresponding in width to the planar surface of the staple cartridge and curvate surfaces that have the same curvature as the arcuate surfaces of the staple cartridge in an opposed direction. The staple cartridge may include a knife channel that is located along the centerline of the staple cartridge.

In a further embodiment of the presently disclosed surgical stapling apparatus, the staple cartridge may include first and second planar surfaces, wherein each planar surface includes at least one row of retention slots. The first and second planar surfaces are substantially parallel with a bottom surface of the staple cartridge and with each other, but are vertically spaced apart such that there are not coplanar with each other. As in the previous embodiments, the staple cartridge includes a plurality of fastener ejection members and a plurality of surgical fasteners. A first gap is defined between a planar tissue contacting surface of an anvil member and the first planar surface of the staple cartridge and a second gap is defined between the planar tissue contacting surface of the anvil member and the second planar surface. The staple cartridge may include a knife channel that is located along the centerline of the staple cartridge. Alternatively, an anvil member having a complementary surface configuration may be used in combination with the staple cartridge, wherein the spacing between the second planar surface of the staple cartridge and a corresponding surface of the anvil member defines a gap that is greater than the second gap.

In a further embodiment of the presently disclosed surgical stapling apparatus, a staple cartridge is provided having a plurality of fastener ejection members and a plurality of surgical fasteners. The staple cartridge includes a planar surface opposed to a bottom surface. A filler layer is positioned atop the planar surface. The filler layer may be formed from a buttress material. The filler layer is generally triangular in shape and extends downwards and outwards from a centerline of the staple cartridge such that its maximum height is proximate to the centerline. An anvil member having a planar surface may be used in cooperation with the staple cartridge for forming completed surgical fasteners. Alternatively, an anvil member having a tapered (i.e. angled) surface that complements the filler layer may be used. The staple cartridge may include a knife channel.

An alternate embodiment of the presently disclosed surgical stapling apparatus includes a staple cartridge and an anvil member. The staple cartridge includes a plurality of surgical fasteners and a plurality of fastener ejection members. A top plate extends between inner and outer walls of the staple cartridge and is a planar structure that is substantially parallel to a bottom surface of the staple cartridge. A vertical member abuts the inner wall. Vertically spaced from the top plate is a cross member that is flexibly attached to the vertical member. A top surface of the cross member defines a tissue contacting surface in opposition to a tissue contacting surface of the anvil member. During approximation and/or formation of surgical fasteners, the cross member flexes such that the gap between the tissue contacting surfaces is at a minimum near the centerline of the staple cartridge and a maximum near the outer wall of the staple cartridge. The staple cartridge may include a knife channel. Alternatively, the anvil member may include tapered surfaces that define the tissue contacting surface, wherein the tapered surfaces extend outwards and upwards from the centerline of the staple cartridge such that the anvil member has its maximum thickness near the centerline and its minimum thickness near outer edges of the anvil member.

In an additional embodiment of the presently disclosed surgical stapling apparatus, a substantially planar anvil member and a stepped staple cartridge are disclosed. In this embodiment, the staple cartridge includes a plurality of stepped surfaces each of which is substantially a planar structure. Each stepped surface of the staple cartridge is configured for contacting tissue and includes a plurality of retention slots. Each retention slot is adapted for receiving a surgical fastener therein. Similar to the previously disclosed embodiments, the surgical fasteners in one surface may have a leg length that is different from the leg length of the surgical fasteners in an adjacent surface. The tissue contacting (i.e. stepped surfaces) surfaces may be arranged in two linear rows that are separated by a knife channel. The tissue contacting surfaces in each row are parallel to one another, but are not coplanar with each other thereby defining the stepped arrangement of the tissue contacting surfaces. The transition from one tissue contacting surface to the adjacent tissue contacting surface is an angled wall surface.

All of the presently disclosed embodiments of the surgical stapling instrument provide a variable pressure gradient (i.e. load profile) to the layers of tissue that are joined together with the surgical fasteners. Therefore, the layers of tissue that are proximate to the center of the surgical stapling instrument (i.e. center of the staple cartridge) are subjected to higher compressive forces (i.e. loads), thereby forming thinner layers of tissue as compared to layers of tissue that are further away from the center of the surgical stapling instrument. Since the layers of tissue nearest the center of the surgical stapling instrument can be compressed more, a smaller sized surgical staple or fastener can be used to mechanically suture (i.e. fasten) the transected layers of tissue. Further still, providing a gradual compression gradient to the layers of tissue to be joined, may result in a higher degree of hemostasis. Due to the contoured shape of the staple cartridge, the layers of tissue can be compressed more at the center of the surgical stapling instrument, because tissue can translate (i.e. move) from a region of relatively high pressure (i.e. at the center) to a region of relatively low pressure (i.e. at the edges) as the anvil member is moved relative to the staple cartridge, thereby defining the pressure gradient.

In a further aspect of the present disclosure, a staple cartridge for a surgical stapling apparatus comprises a first tissue contacting surface and a second tissue contacting surface. The first tissue contacting surface and the second tissue contacting surface are not co-planar. A third surface generally extends between the first tissue contacting surface and the second tissue contacting surface and an angle is defined between the third surface and at least one of the first or second tissue contacting surfaces. A plurality of first retention slots are defined in the first tissue contacting surface and a plurality of second retention slots are defined in the second tissue contacting surface. Each retention slot is configured for housing a staple therein.

The cartridge may have staples having a first leg length in the first retention slots and staples having a second leg length in the second retention slots, wherein the second leg length is different from the first leg length. The cartridge may be releasably attached to a body of the surgical apparatus, or may be part of a detachable disposable loading unit.

A knife channel desirably extends longitudinally along the cartridge. The first tissue contacting surface is desirably adjacent the knife channel. In certain preferred embodiments, the staples with the first leg length, which have leg lengths smaller than the staples with the second leg length, are disposed adjacent the knife channel.

The first tissue contacting surface may be substantially parallel to the second tissue contacting surface.

In a further aspect of the present disclosure, a surgical stapling apparatus comprises a handle portion, a body portion extending distally from the handle portion and defining a longitudinal axis, and a tool assembly at a distal end of the body portion. The tool assembly includes a cartridge having a first tissue contacting surface and a second tissue contacting surface. The first tissue contacting surface and the second tissue contacting surface are not co-planar. A third surface generally extends between the first tissue contacting surface and the second tissue contacting surface. An angle is defined between the third surface and at least one of the first or second tissue contacting surfaces. A plurality of first retention slots are defined in the first tissue contacting surface and a plurality of second retention slots are defined in the second tissue contacting surface. Each retention slot is configured for housing a staple therein. The tool assembly of the surgical stapling apparatus desirably includes an anvil member having a surface for contacting tissue and a number of staple forming depressions defined in the surface of the anvil member. The surface of the anvil member is disposed in opposition to the first tissue contacting surface and the second tissue contacting surface. The surface of the anvil member and the first tissue contacting surface define a first gap and the surface of the anvil member and the second tissue contacting surface define a second gap. The first gap has a different dimension from the second gap. In certain preferred embodiments, the first gap is less than the second gap. The staples with the smaller length are desirably disposed adjacent a centerline of the staple cartridge.

In another aspect of the present disclosure, a staple cartridge for a surgical stapling apparatus comprises a first tissue contacting surface and a second tissue contacting surface. The first tissue contacting surface and the second tissue contacting surface are not co-planar. A third surface generally extends between the first tissue contacting surface and the second tissue contacting surface. The third surface is a non-planar surface. A plurality of first retention slots are defined in the first tissue contacting surface and a plurality of second retention slots are defined in the second tissue contacting surface. Each retention slot is configured for housing a staple therein.

The cartridge may have staples having a first leg length in the first retention slots and staples having a second leg length in the second retention slots, wherein the second leg length is different from the first leg length. The cartridge may be releasably attached to a body of the surgical apparatus, or may be part of a detachable disposable loading unit.

A knife channel desirably extends longitudinally along the cartridge. The first tissue contacting surface is desirably adjacent the knife channel. In certain preferred embodiments, the staples with the first leg length, which have leg lengths smaller than the staples with the second leg length, are disposed adjacent the knife channel.

The first tissue contacting surface may be substantially parallel to the second tissue contacting surface.

The presently disclosed surgical stapling instruments, together with attendant advantages, will be more clearly illustrated below by the description of the drawings and the detailed description of the embodiments.

Other objects and features of the present disclosure will become apparent from consideration of the following description taken in conjunction with the accompanying drawings.

BRIEF DESCRIPTION OF THE DRAWINGS

Embodiments of the presently disclosed surgical stapling apparatus are described herein with reference to the accompanying drawings, wherein:

FIG. 4 is a perspective view of an alternative surgical stapling instrument constructed in accordance with the present disclosure;

FIG. 16A is a cross-sectional side elevation view of a tissue interface following the firing of a conventional surgical stapling instrument;

FIG. 16B is a cross-sectional side elevational view of the resulting tissue interface following the firing of surgical stapling instrument of FIGS. 7 and 10-15;

DETAILED DESCRIPTION OF EMBODIMENTS

Figure 1:
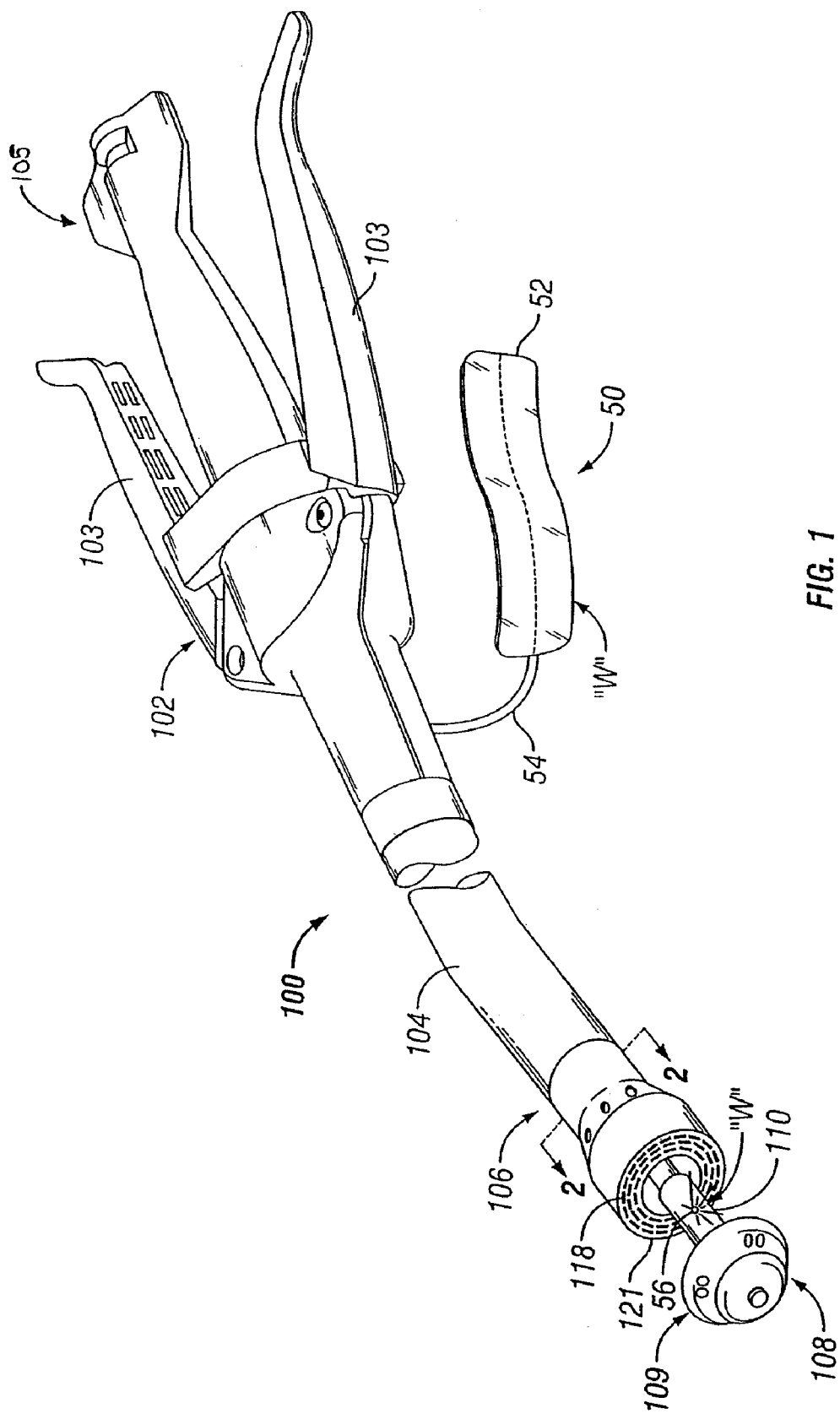
FIG. 1 is a perspective view of a surgical stapling instrument constructed in accordance with the present disclosure.

Embodiments of the presently disclosed surgical stapling instruments will now be described in detail with reference to the drawing figures wherein like reference numerals identify similar or identical elements. In the drawings and in the description which follows, the term "proximal", as is traditional, will refer to the end of the surgical stapling instrument which is closest to the operator while the term "distal" will refer to the end of the device which is furthest from the operator.

The present disclosure relates to a staple cartridge and an anvil member for use in a disposable or re-usable surgical stapling apparatus. The presently disclosed staple cartridge and anvil member, as will be discussed in detail hereinbelow, may be used with any of the surgical stapling apparatus shown in FIG. 1, 4, 5, or 6. In addition, a replaceable loading unit may be located in either the disposable or the reusable surgical stapling apparatus. In one embodiment, the replaceable loading unit includes a staple cartridge, including any of the staple cartridges disclosed herein. Alternatively, the replaceable loading unit includes the staple cartridge and an anvil member, including any of the anvil members disclosed herein. In combination with the disposable or the reusable surgical stapling apparatus, the replaceable loading unit provides improved flexibility of the respective surgical stapling apparatus in that the respective surgical stapling apparatus is readily adaptable for different stapling procedures. In each of the embodiments that are hereinafter disclosed, staples or surgical fasteners disposed in the staple cartridge are arranged such that tips of the surgical fasteners may be substantially flush with a tissue contacting surface of the staple cartridge. Alternately, the tips of the surgical fasteners may be located above or below the tissue contacting surface.

Figure 2:
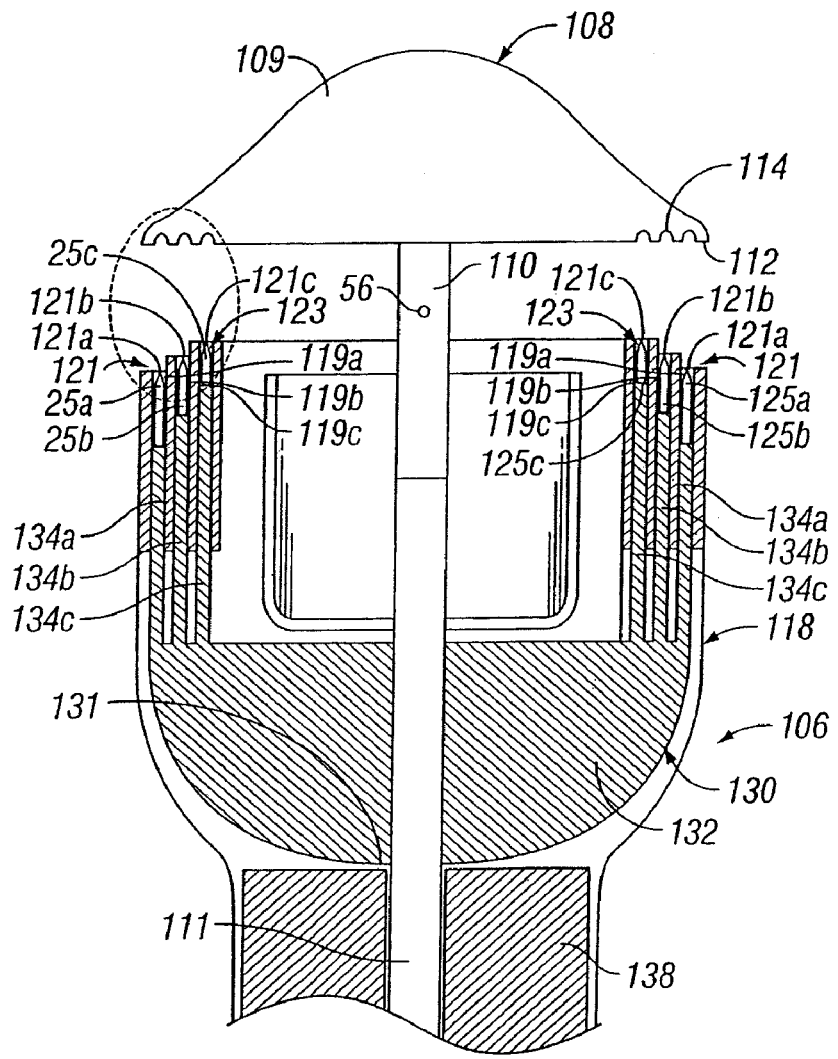
FIG. 2 is a schematic cross-sectional side elevational view of the distal end portion of the surgical stapling instrument of FIG. 1, as taken through 2-2 of FIG. 1.

Referring now in detail to FIGS. 1-2, in which like reference numerals identify similar or identical elements, a surgical stapling instrument, in accordance with a first embodiment of the disclosure, is generally designated as 100.

As seen in FIG. 1, surgical stapling instrument 100 includes a handle assembly 102 having at least one pivotable actuating handle member 103, and further includes advancing means 105. Extending from handle assembly 102, there is provided a tubular body portion 104 which may be constructed so as to have a curved shape along its length. Tubular body portion 104 terminates in a fastener ejection assembly 106 having a circular staple cartridge 118 including a tissue contacting surface 121 disposed at a distal end thereof. An anvil shaft 110 operatively couples an anvil assembly 108 to handle assembly 102. Anvil assembly 108 is repositionable from a location where it is in close cooperative alignment with staple cartridge 118 to a location where it is spaced apart from staple cartridge 118. Anvil assembly 108 includes an anvil head 109. Further still, surgical stapling instrument 100 may include a wound closure assembly 50. Wound closure assembly 50 includes at least one storage device or reservoir 52 and at least one supply line 54. Supply line 54 fluidly couples reservoir 52 to anvil shaft 110, wherein anvil shaft includes at least one opening 56 for dispensing wound closure material "W". By providing wound closure material "W" in combination with surgical fasteners, the bond formed between the layers of tissue has improved strength.

As seen in FIG. 2, tissue contacting surface 121 is stepped including an outer tissue contacting surface 121a, an intermediate tissue contacting surface 121b, and an inner tissue contacting surface 121c. Each tissue contacting surface 121a-121c has a different height from one another as measured from a point 131 on a bottom surface of a staple pusher or fastener ejection member 130. Point 131 is proximal to a shaft 111 in a region where the bottom surface of fastener ejection member 130 is substantially planar. Specifically, tissue contacting surfaces 121a-121c are planar structures that are substantially parallel to one another, but are not co-planar (i.e. stepped) with one another. In addition, each tissue contacting surface 121a-c defines a planar axis that extends through the respective tissue contacting surface 121a-c. A first wall surface interconnects tissue contacting surfaces 121a and 121b, while a second wall surface interconnects tissue contacting surfaces 121b and 121c. The first and second wall surfaces are planar structures wherein each wall surface defines a planar axis. In one embodiment, the planar axes of the wall surfaces are orthogonal to the planar axes of tissue contacting surfaces 121a-c.

Inner tissue contacting surface 121c has the greatest height, outer tissue contacting surface 121a has the least height, and intermediate tissue contacting surface 121b has a height between the heights of outer and inner tissue contacting surfaces 121a, 121c. While tissue contacting surfaces 121a-121c are shown as increasing in height from outer tissue contacting surface 121a to inner tissue contacting surface 121c (i.e. radially inward), it is within the scope of the present disclosure that the heights of each tissue contacting surface can vary depending on the particular surgical procedure. For example, tissue contacting surfaces 121a-121c can increase in height in a radially outward direction, the intermediate tissue contacting surface 121b can be the highest or the lowest tissue contacting surface, or at least two of tissue contacting surfaces 121a-121c can have the same height.

Figure 2A:
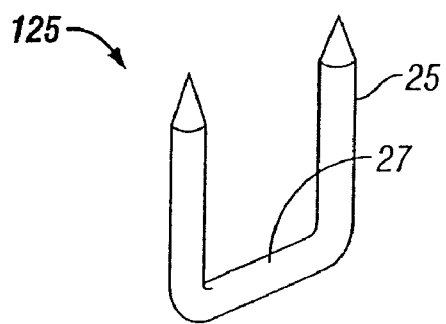
FIG. 2A is a perspective view of a surgical fastener in accordance with an embodiment of the present disclosure.

In one embodiment, each tissue contacting surface 121a-121c includes a respective annular row 119a-119c of retention slots 123 formed therein. Each retention slot 123 of annular rows 119a-119c is configured and dimensioned to retain a staple or surgical fastener 125 therein. As shown in FIG. 2A, each surgical fastener 125 includes a backspan 27 and a pair of depending legs 25. Each leg 25 forms a right angle in relation to backspan 27. In one embodiment, each annular row 119a-119c of slots 123 includes a respective surgical fastener 125a-125c having its own characteristic features.

As seen in FIG. 2, legs 25a of surgical fasteners 125a have a first leg length, legs 25b of surgical fasteners 125b have a second leg length, and legs 25c of surgical fasteners 125c have a third leg length. In particular, surgical fasteners 125a-125c increase in height in a radially outward direction. In one embodiment, legs 25c of surgical fasteners 125c have a leg length of about 2.3 mm, legs 25b of surgical fasteners 125b have a leg length of about 3.5 mm, and legs 25a of surgical fasteners 125a have a leg length of about 4.1 mm. As such, inner tissue contacting surface 121c has the greatest height and retains surgical fasteners 125c having the shortest leg lengths, and outer tissue contacting surface 121a has the least height and retains surgical fasteners 125a having the longest leg lengths. Having tissue contacting surface 121 step progressively downward at intermediate tissue contacting surface 121b and then again at outer tissue contacting surface 121a results in the formation of surgical fasteners 125b and 125c, respectively. It is envisioned and within the scope of the present disclosure that any number of arrangements are possible.

While a single annular row 119a-119c of retention slots 123 is shown for each tissue contacting surface 121a-121c, it is envisioned and within the scope of the present disclosure that each tissue contacting surface 121a-121c can include multiple annular rows of retention slots.

As seen in FIG. 2, a fastener ejection assembly 106 of surgical stapling instrument 100 includes fastener ejection member 130 disposed within staple cartridge 118. Fastener ejection member 130 includes a proximal portion 132 having a generally frusto-conical shape and a distal portion defining concentric rings of peripherally spaced staple pushers 134a-c, each one of which is received within a respective staple retention slot 123 and is cooperative with its respective surgical fastener 125a-c disposed in annular rows 119a-c. In one embodiment, it is envisioned that proximal portion 132 of fastener ejection member 130 is configured and dimensioned to be contacted by a distal end of a driver tube 138. Hence, upon advancing fastener ejection member 130 by advancing driver tube 138, staple pushers 134a-c will pass further into retention slots 123 thereby pushing surgical fasteners 125 contained therein axially outward.

In an alternate embodiment, staple pushers 134a-c of fastener ejection member 130 have different heights for cooperating with different sized surgical fasteners. In particular, staple pushers 134a-c are sized such that when surgical fasteners 125a-c are disposed in their respective annular rows 119a-c, tips of surgical fasteners 125a-c are located substantially in the same plane despite the difference in leg lengths between each row of surgical fasteners.

Surgical stapling instrument 100 (FIG. 1) includes circular anvil assembly 108 having anvil head 109 and anvil shaft 110 extending from a proximal end thereof and adapted to engage shaft 111 extending distally from staple cartridge 118. Anvil head 109 includes an annular anvil member 112 disposed at a proximal end thereof, wherein anvil member 112 includes at least one, row of fastener forming depressions 114 formed circumferentially thereabout. In one embodiment, surgical stapling instrument 100 includes three laterally spaced rows of fastener forming depressions 114 formed circumferentially thereabout. Each fastener forming depression 114 is in registration with a corresponding retention slot 123.

Figure 3A:
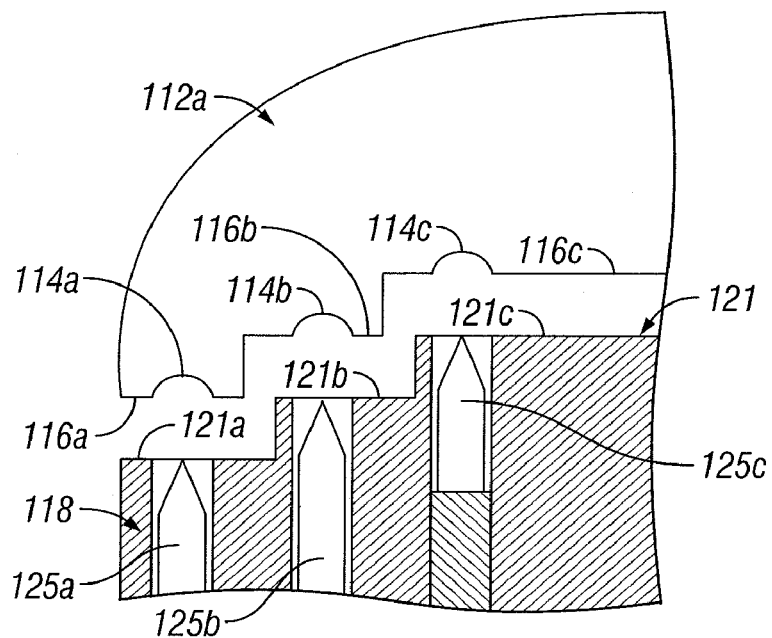
FIG. 3A is an enlarged schematic representation of the indicated area of FIG. 2, illustrating tissue contacting surfaces in accordance with an alternate embodiment of the present disclosure.
Figure 3B:
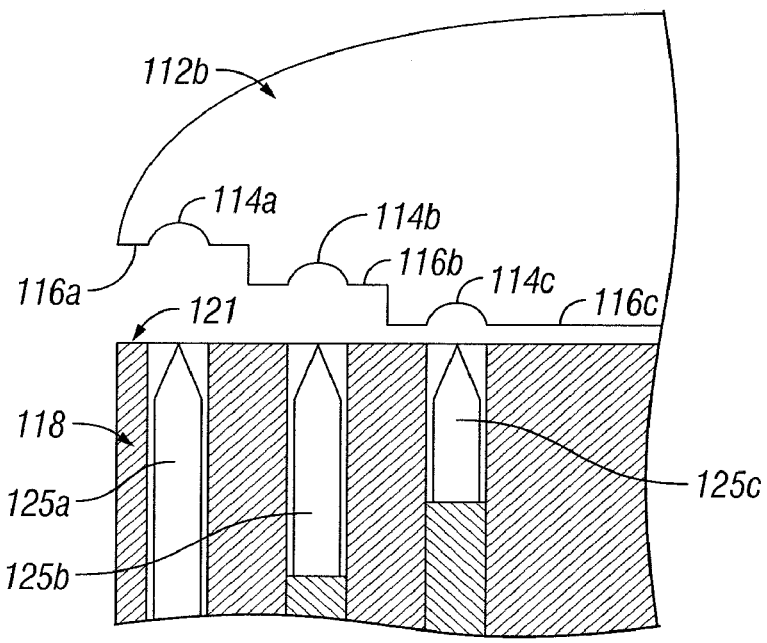
FIG. 3B is an enlarged schematic representation of the indicated area of FIG. 2, illustrating tissue contacting surfaces in accordance with another embodiment of the present disclosure.
Figure 3C:
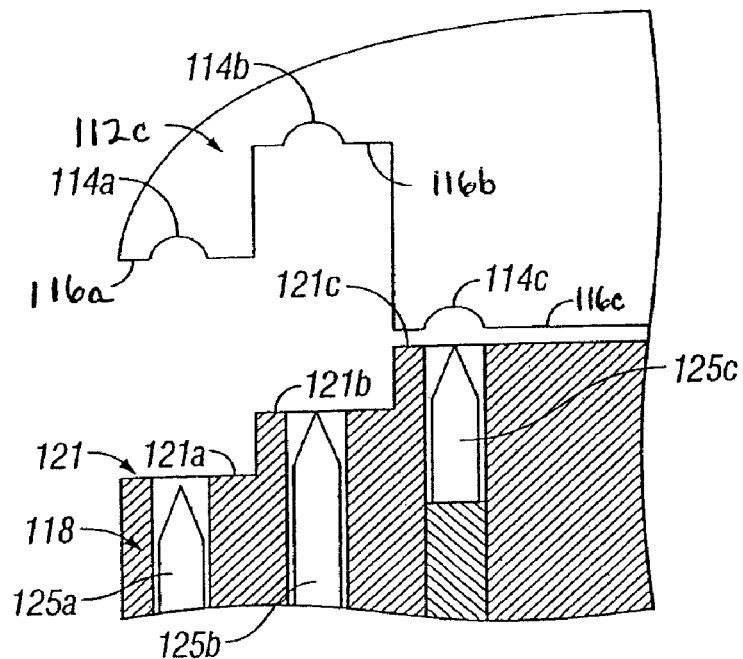
FIG. 3C is an enlarged schematic representation of the indicated area of FIG. 2, illustrating tissue contacting surfaces in accordance with still another embodiment of the present disclosure.
Figure 3D:
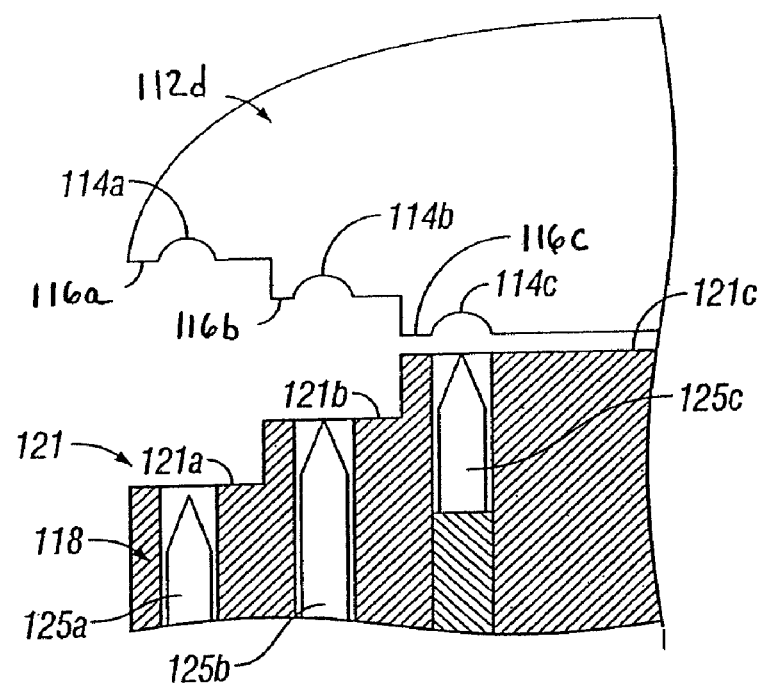
FIG. 3D is an enlarged schematic representation of the indicated area of FIG. 2, illustrating tissue contacting surfaces in accordance with a further embodiment of the present disclosure.

While anvil member 112 is shown in FIG. 2 as having a substantially planar tissue contacting surface, it is envisioned and within the scope of the present disclosure for surgical stapling instrument 100 to have a number of alternate configurations. For example, as seen in FIG. 3A, anvil member 112a can have a tissue contacting surface, including surfaces 116a-116c, which is shaped (i.e. stepped) to complement stepped tissue contacting surface 121 of staple cartridge 118 or, as seen in FIG. 3B, anvil member 112b can have a tissue contacting surface, including surfaces 116a-c, which is stepped while tissue contacting surface 121 of staple cartridge 118 is substantially planar. In addition, for example, as seen in FIG. 3C, anvil member 112c can have one row of staple pockets 114b that extends a greater distance than staple pockets 114a or 114c into anvil member 112c for accommodating surgical fasteners having a longer leg length or, as seen in FIG. 3D, anvil member 112d can have a tissue contacting surface, including surfaces 116a-c, which is stepped to mirror tissue contacting surface 121 of staple cartridge 118 (i.e. the depths of individual tissue contacting surfaces of the tissue contacting surface of anvil member 112d are substantially equal to the depths of the individual tissue contacting surfaces 121a-121c of staple cartridge 118).

The sizes of surgical fasteners 125a-125c are selected and intended for use in gastric firings typically required in bariatric procedures. However, it is envisioned and within the scope of the present disclosure that the sizes of surgical fasteners 125a-125c selected can be chosen for performance in different types of tissue, such as, for example, the colon, bowels, lungs, the bronchus, pulmonary vessels, the liver, and the like.

In operation, surgical stapling instrument 100 is positioned within a tubular organ in the body of the patient and the ends of the organ to be joined are positioned in a gap between staple cartridge 118 and anvil assembly 108. As is conventional, the ends of the organ may be secured around anvil shaft 110 by a purse string suture prior to approximation of anvil assembly 108 to staple cartridge 118. Surgical stapling instrument 100 is then approximated and fired. An example of a surgical stapling apparatus and methods for its use are disclosed in U.S. Pat. No. 5,915,616, currently assigned to Tyco Healthcare Group LP, the entire contents of which is incorporated herein by reference.

Figure 7:
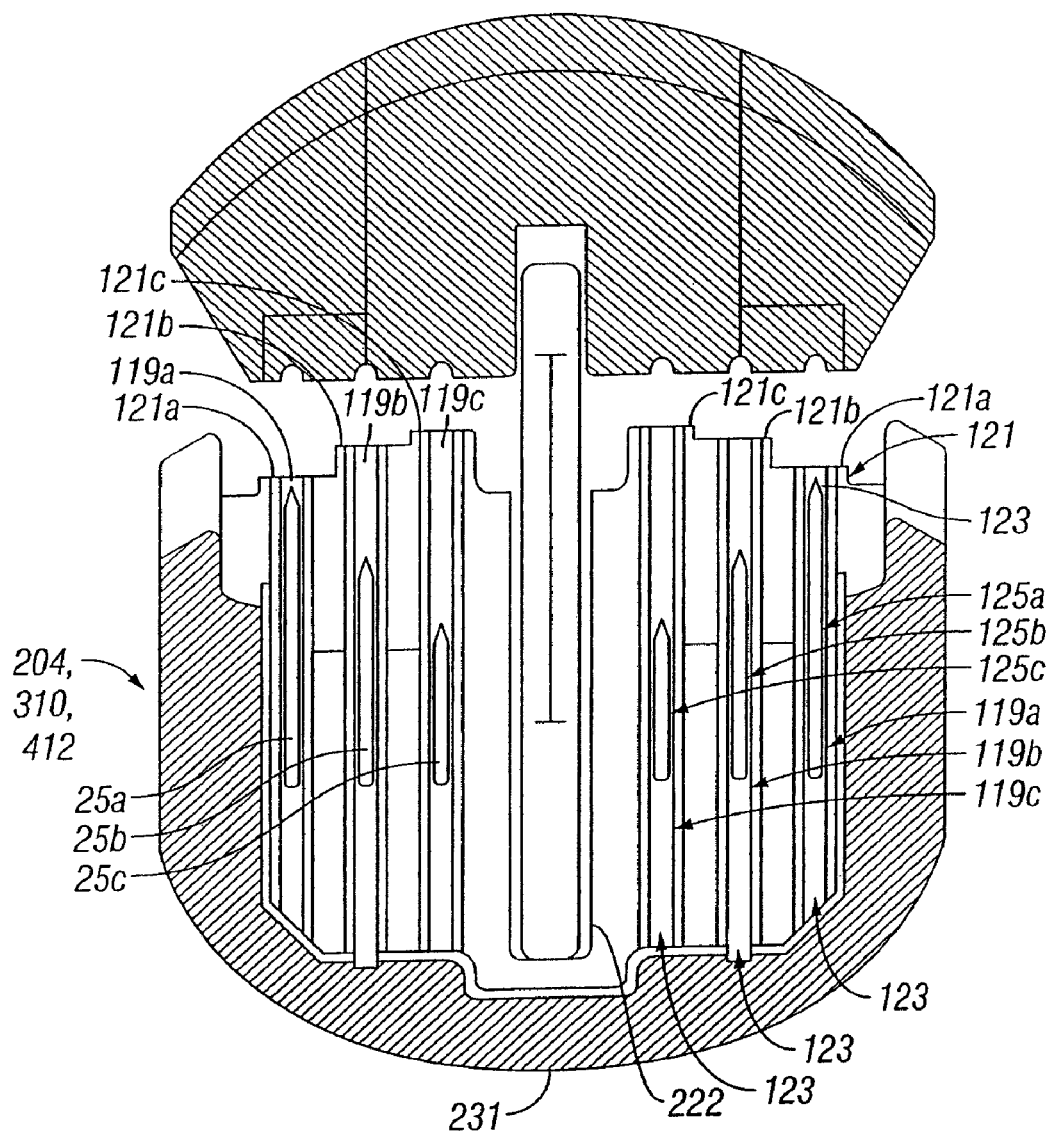
FIG. 7 is a schematic cross-sectional side elevational view of the distal end portion of the surgical stapling instruments of FIGS. 4-6, as taken through 7-7 of each of FIGS. 4-6.

Turning now to FIGS. 4 and 7, a surgical stapling instrument, of the gastro-intestinal anastomosis type for performing surgical anastomotic stapling, in accordance with another embodiment of the disclosure, is generally designated as 200. Surgical stapling instrument 200 includes a first handle 202 having a jaw 203 defining a staple cartridge receiving section extending from a distal end thereof, a staple cartridge 204 receivable in jaw 203, a second handle 206 having a jaw 205 defining an anvil member receiving section extending from a distal end thereof, and an anvil member 208 operatively associated with jaw 205. First and second handles 202, 206 are configured such that staple cartridge 204 is substantially aligned with anvil member 208.

As seen in FIG. 7, staple cartridge 204 includes a stepped tissue contacting surface 121 including an outer tissue contacting surface 121a, an intermediate tissue contacting surface 121b, and an inner tissue contacting surface 121c, each of which has a different height from one another as measured from a point 231 that is located on a bottom surface of staple cartridge 204, wherein point 231 exists along a centerline of staple cartridge 204. Tissue contacting surfaces 121a-121c are planar structures that are substantially parallel to one another, but are not co-planar with one another. For example, tissue contacting surfaces 121a-121c, as shown in FIG. 7, can decrease in height in a direction orthogonally outward from knife track 222. In embodiments that do not include knife track 222, tissue contacting surfaces 121a-c decrease in height in a direction orthogonally outward from a centerline of staple cartridge 204.

Each tissue contacting surface 121a-121c includes a respective linear row 119a-119c of retention slots 123 formed therein. Each retention slot 123 of linear rows 119a-119c is configured and dimensioned to retain a surgical fastener 125 therein. Each linear row 119a-119c of slots 123 includes a respective surgical fastener 125a-125c having its own characteristic features.

As seen in FIG. 7, legs 25a of surgical fasteners 125a have a first leg length of about 4.1 mm, legs 25b of surgical fasteners 125b have a second leg length of about 3.5 mm, and legs 25c of surgical fasteners 125c have a third leg length of about 2.3 mm. In particular, surgical fasteners 125a-125c increase in height in an orthogonally outward direction relative towards optional knife track 222. Knife track 222 is disposed along a centerline of staple cartridge 204, 310, or 412 and is adapted for slidably receiving an optional knife (not shown). Having tissue contacting surface 121 step progressively downward at intermediate tissue contacting surface 121b and then again at outer tissue contacting surface 121a results in the formation of surgical fasteners 125b and 125c, respectively. It is envisioned and within the scope of the present disclosure that any number of arrangements are possible.

In operation, surgical stapling instrument 200 is fired similarly to and in accordance with other known surgical stapling instruments. An example of a surgical stapling apparatus and methods for its use are is disclosed in U.S. Pat. No. 6,202,914, currently assigned to Tyco Healthcare Group LP, the entire contents of which is incorporated herein by reference.

Referring additionally to FIG. 16B, following the firing of surgical stapling instrument 200, the resulting tissue interface is seen in cross-section. Accordingly, some or all of surgical fasteners 125a-125c serve to hold tissues "A" and "B" to one another while surgical fasteners 125c also provide the hemostasis.

While surgical stapling instrument 200 is a linear-type surgical stapler, it is envisioned and within the scope of the present disclosure, that surgical stapling instrument 200 can include a tissue contacting surface having a cross-sectional profile for at least one of the anvil member and the staple cartridge which is substantially similar to the tissue contacting surfaces of the anvil member and the staple cartridge of surgical stapling instrument 100, as shown in FIGS. 3A-3D.

Figure 5:
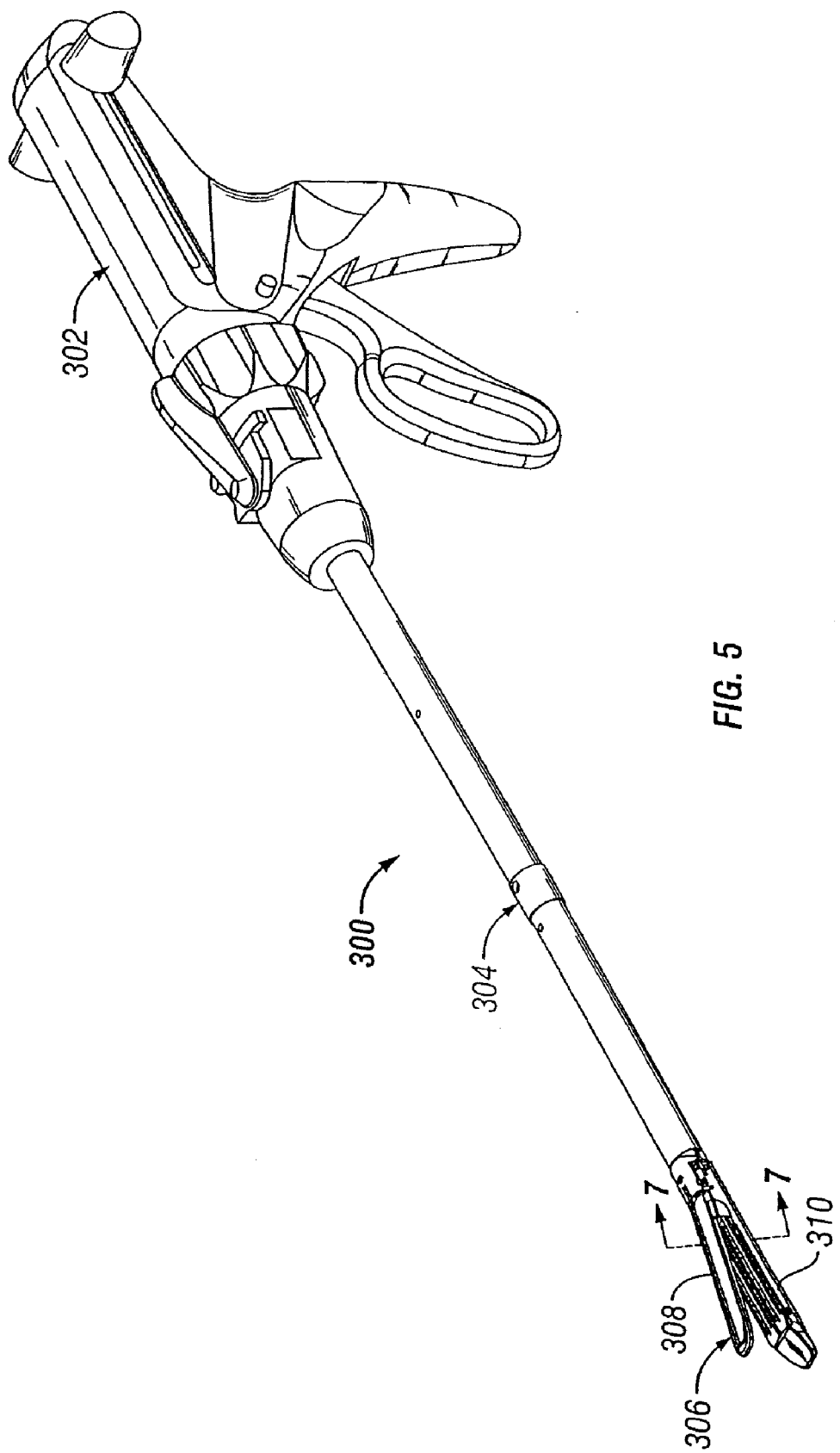
FIG. 5 is a perspective view of yet another surgical stapling instrument constructed in accordance with the present disclosure.
Figure 6:
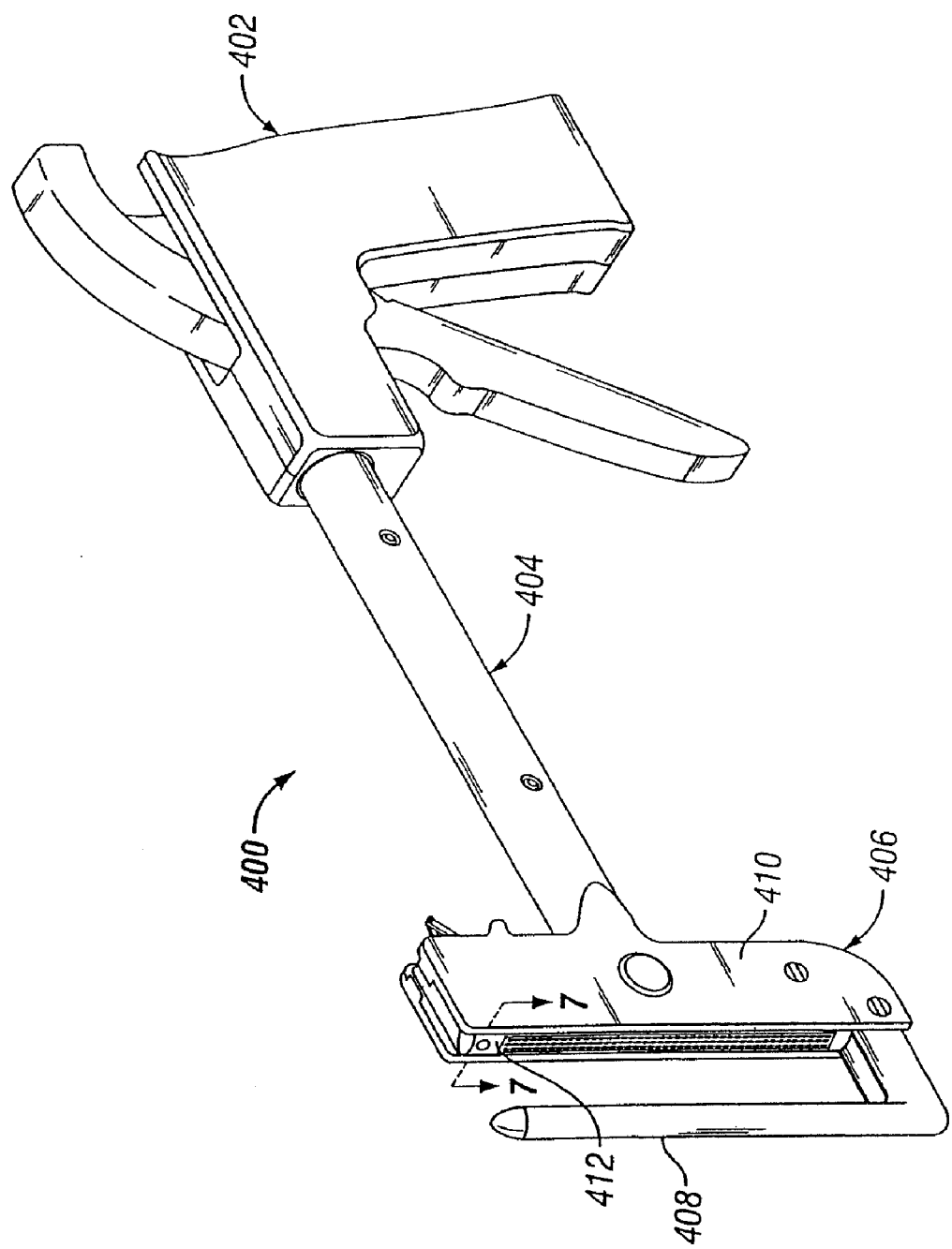
FIG. 6 is a perspective view of still another surgical stapling instrument constructed in accordance with the present disclosure.
Figure 6A:
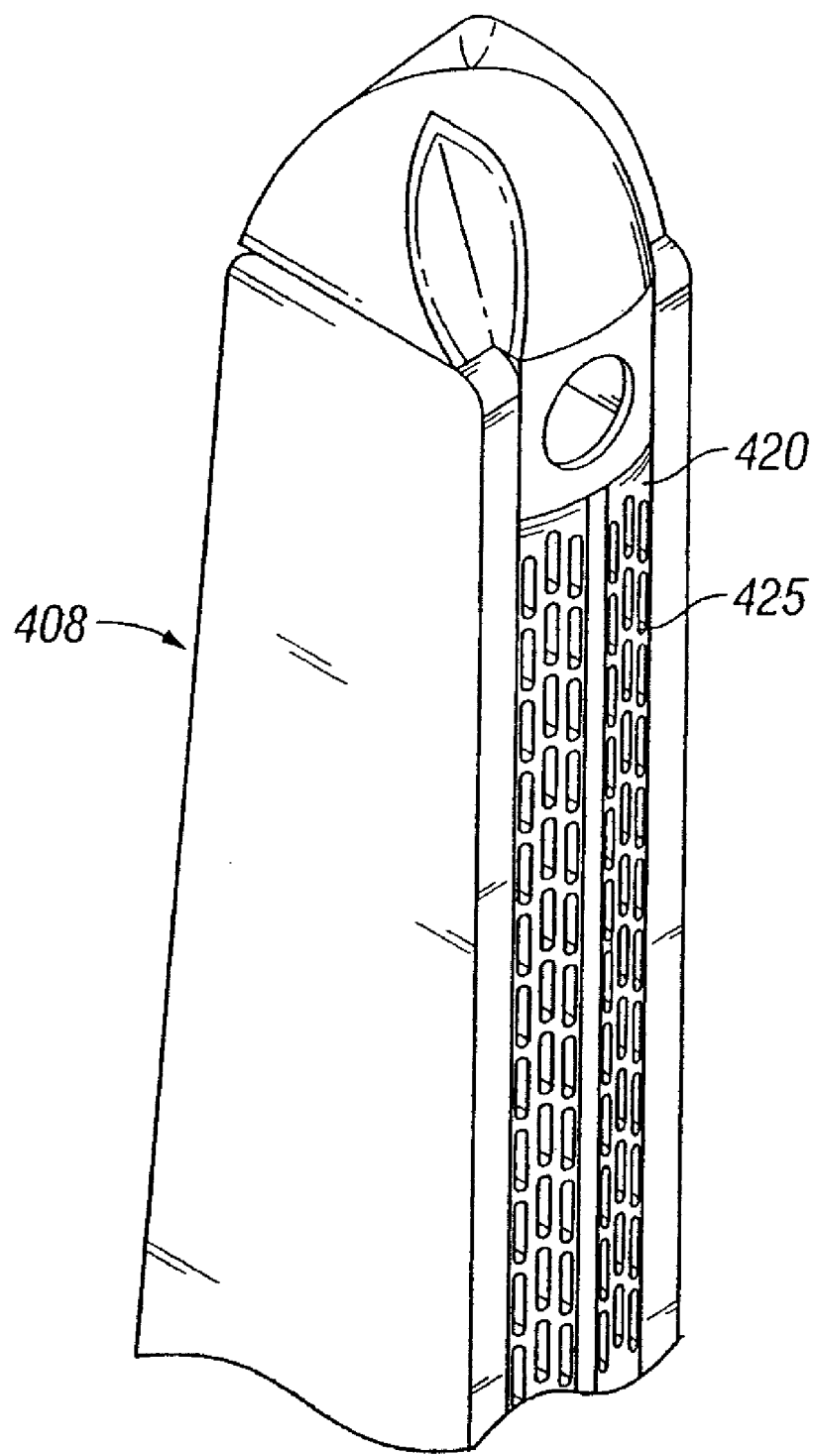
FIG. 6A is a perspective view of a portion of an anvil member of FIG. 6.

Turning now to FIGS. 5 and 7, a surgical stapling instrument, of the laparoscopic type for performing surgical anastomotic stapling, in accordance with another embodiment of the disclosure, is generally designated as 300. Surgical stapling instrument 300 includes a handle 302, an operative tool 306, and an elongated shaft 304 for interconnecting operative tool 306 to handle 302. In general, operative tool 306 is designed to clamp over and then to staple and divide tissue held therein. Accordingly, as seen in FIG. 5, operative tool 306 is a pair of opposed jaws including an anvil member 308 and a staple cartridge 310 pivotally coupled to one another.

Staple cartridge 310 of surgical stapling instrument 300 includes a stepped tissue contacting surface 121 similar to tissue contacting surface 121 of staple cartridge 204 of surgical stapling instrument 200. Accordingly, reference is made to FIG. 7 and the above detailed discussion of tissue contacting surface 121 of staple cartridge 204 for an illustration and a discussion of tissue contacting surface 121 of staple cartridge 310 of surgical stapling instrument 300.

In operation, surgical stapling instrument 300 is fired similarly to and in accordance with other known surgical stapling instruments. For a detailed discussion of the approximation and firing of surgical stapling instrument 300, reference is made to commonly assigned U.S. Pat. No. 5,865,361, currently assigned to Tyco Healthcare Group LP, the entire contents of which is incorporated herein by reference.

Following the firing of surgical stapling instrument 300 the resulting tissue interface, as seen in cross-section, is substantially similar to the resulting tissue interface, as seen in cross-section, following the firing of surgical stapling instruments 100 and 200. Accordingly, as seen in FIG. 16B, some or all of surgical fasteners 125a-125c serve to hold tissues "A" and "B" to one another while surgical fasteners 125c also provide the hemostasis.

While surgical stapling instrument 300 is a linear-type surgical stapler as compared to surgical stapling instrument 100, it is envisioned and within the scope of the present disclosure, that surgical stapling instrument 300 can include a tissue contacting surface having a cross-sectional profile for at least one of the anvil and the staple cartridge which is substantially similar to the tissue contacting surfaces of the anvil and the staple cartridge of surgical stapling instrument 100, as shown in FIGS. 3A-3D.

Turning now to FIGS. 6, 6A, 7, and 7A, a surgical stapling instrument, of the transverse anastomosis type for performing surgical anastomotic stapling, in accordance with yet another embodiment of the disclosure, is generally designated as 400. Surgical stapling instrument 400 includes a handle 402, a barrel 404 extending from handle 402, and an arm 406 extending from the distal end of barrel 404. Surgical stapling instrument 400 further includes an anvil member 408 orthogonally affixed to a distal end of arm 406 and a staple cartridge receiver 410 operatively coupled to the distal end of barrel 404 for holding a disposable staple cartridge 412 thereon. Anvil member 408 is illustrated in further detail in FIG. 6A and includes a tissue contacting surface 420 wherein tissue contacting surface 420 has a plurality of pockets 425 that substantially align with retention slots 123 (FIG. 7). Cooperative alignment between pockets 425 and retention slots 123 form completed surgical fasteners 125 upon actuation of the actuation mechanism in surgical stapling instrument 400.

Staple cartridge 412 of surgical stapling instrument 400 includes a stepped tissue contacting surface 121 similar to tissue contacting surface 121 of staple cartridge 204 of surgical stapling instrument 200. Accordingly, reference is made to FIG. 7 and the above detailed discussion of tissue contacting surface 121 of staple cartridge 204 for an illustration and a discussion of tissue contacting surface 121 of staple cartridge 412 of surgical stapling instrument 400. Further still, staple cartridge 412 may include knife track 222 for slidably receiving a knife (not shown) therein.

Figure 7A:
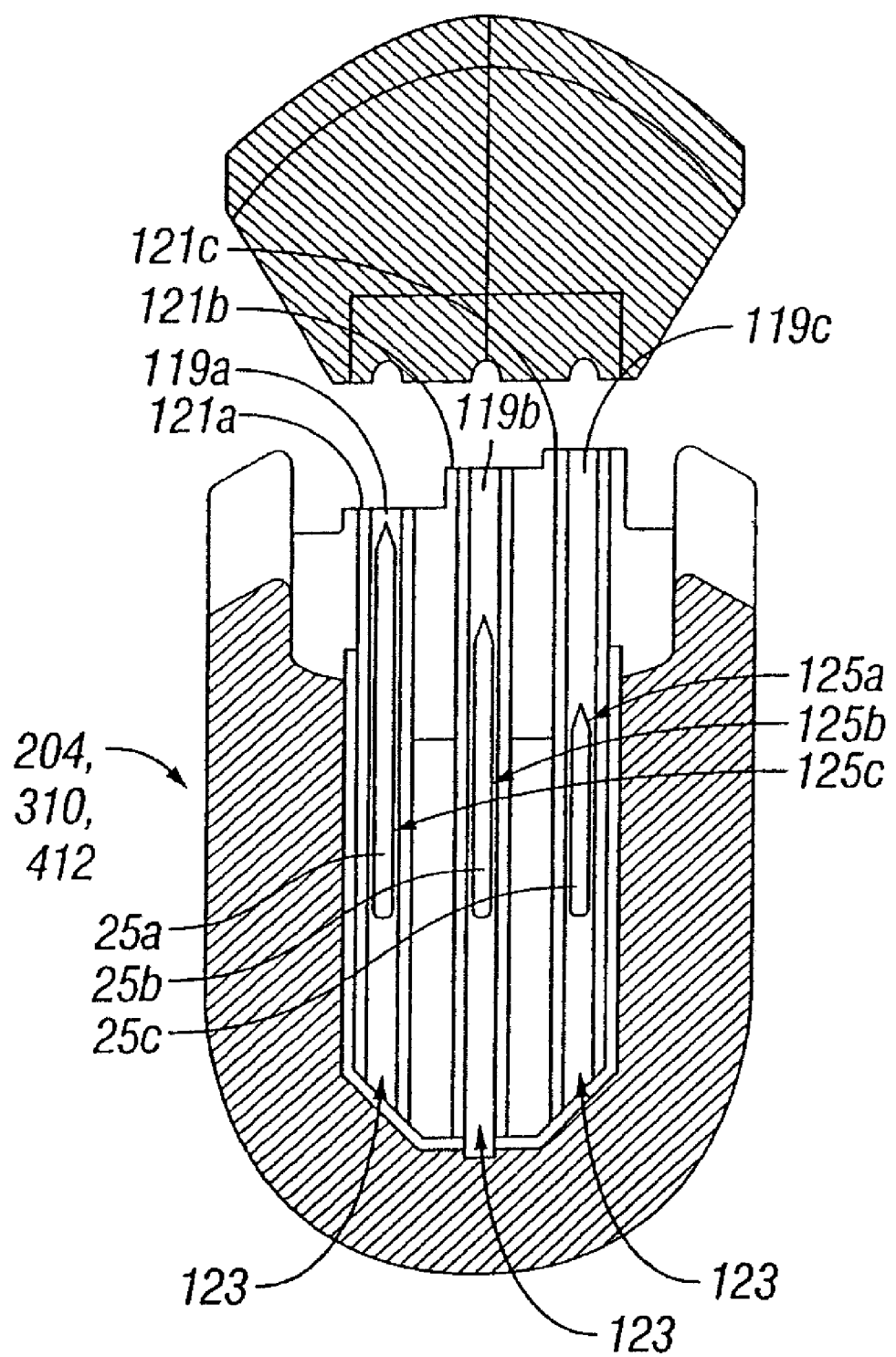
FIG. 7A is a schematic cross-sectional side elevational view of an alternate embodiment of the distal portion of the surgical stapling instrument of FIG. 6

In a further embodiment of the present disclosure, staple cartridge 412' is illustrated in FIG. 7A and discussed in detail hereinafter. Staple cartridge 412' is similar to staple cartridge 412, but only includes three rows 119a-c of retention slots 123 disposed between outer walls of staple cartridge 412'. As in the previously discussed embodiment, each row 119a-c includes a plurality of surgical fasteners wherein surgical fasteners in row 119a have a different leg length from surgical fasteners disposed in row 119b, while surgical fasteners disposed in row 119c have a leg length that is different from at least one of rows 119a or 119b. This embodiment of the staple cartridge does not include a knife track. The arrangement and interrelationship of tissue contacting surfaces 121a-c is similar to that previously disclosed with reference to FIG. 7.

In operation, surgical stapling instrument 400 is fired similarly to and in accordance with other known surgical stapling instruments. For a detailed discussion of the approximation and firing of surgical stapling instrument 400, reference is made to commonly assigned U.S. Pat. No. 5,964,394, currently assigned to Tyco Healthcare Group LP, the entire contents of which is incorporated herein by reference.

Following the firing of surgical stapling instrument 400 the resulting tissue interface, as seen in cross-section, is substantially similar to the resulting tissue interface, as seen in cross-section, following the firing of surgical stapling instruments 100-300. Accordingly, as seen in FIG. 16B, some or all of surgical fasteners 125a-125c serve to hold tissues "A" and "B" to one another while surgical fasteners 125c also provide the hemostasis.

While surgical stapling instrument 400 is a linear-type surgical stapler as compared to surgical stapling instrument 100, it is envisioned and within the scope of the present disclosure, that surgical stapling instrument 400 can include a tissue contacting surface having a cross-sectional profile for at least one of the anvil and the staple cartridge which is substantially similar to the tissue contacting surfaces of the anvil and the staple cartridge of surgical stapling instrument 100, as shown in FIGS. 3A-3D.

While each of the surgical stapling instruments described above and shown herein are configured and adapted to fire surgical fasteners 125, it is envisioned and within the scope of the present disclosure, that tissue contacting surfaces of surgical instruments used in connection with applying two-part fasteners can also have stepped configurations as shown and described herein. A typical two-part surgical fastener applying instrument is shown and described in commonly assigned U.S. Pat. No. 5,573,169, currently assigned to Tyco Healthcare Group LP, the entire contents of which is incorporated herein by reference.

Figure 8:
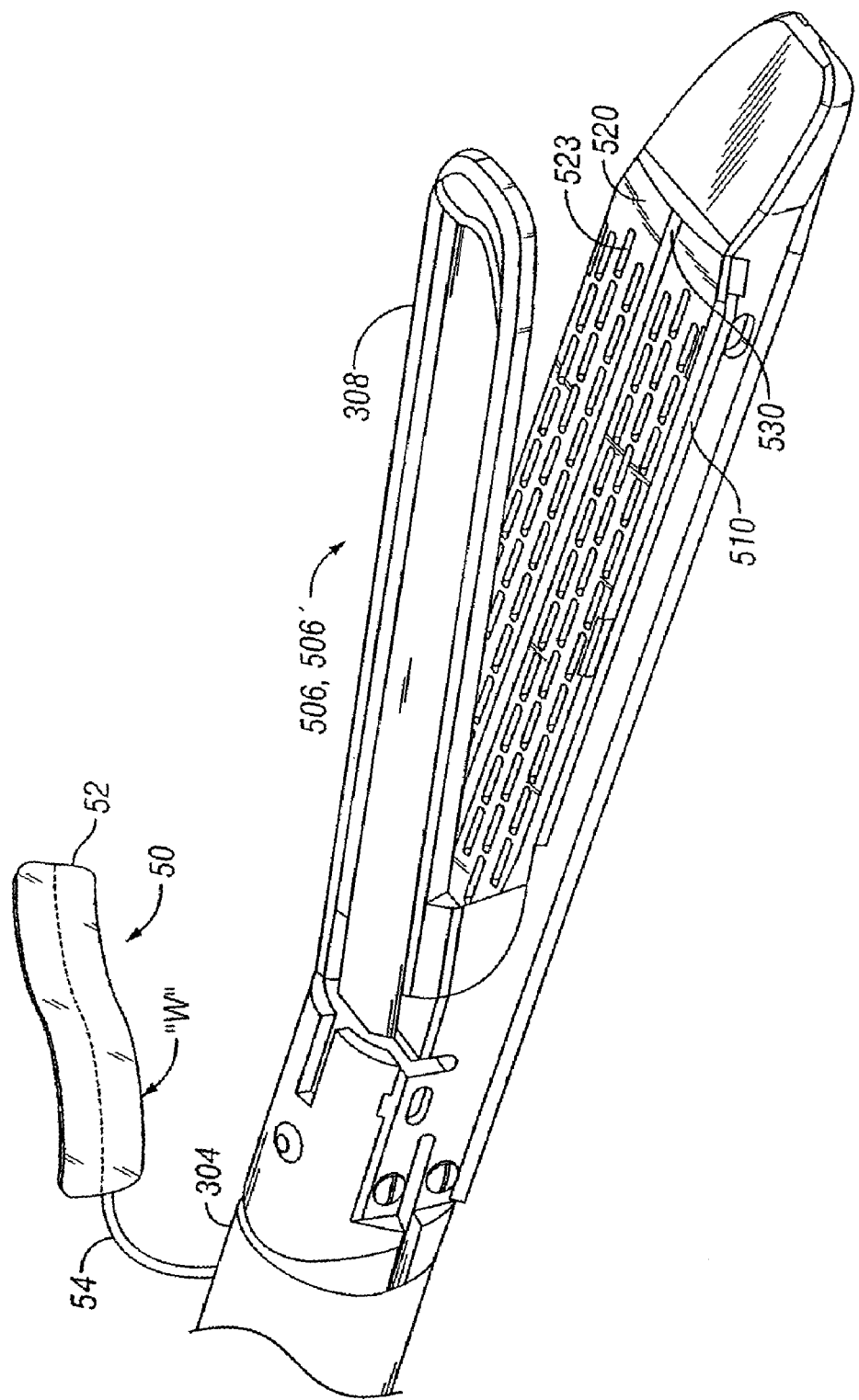
FIG. 8 is a perspective view of a staple cartridge according to another embodiment of the present disclosure.
Figure 9A:
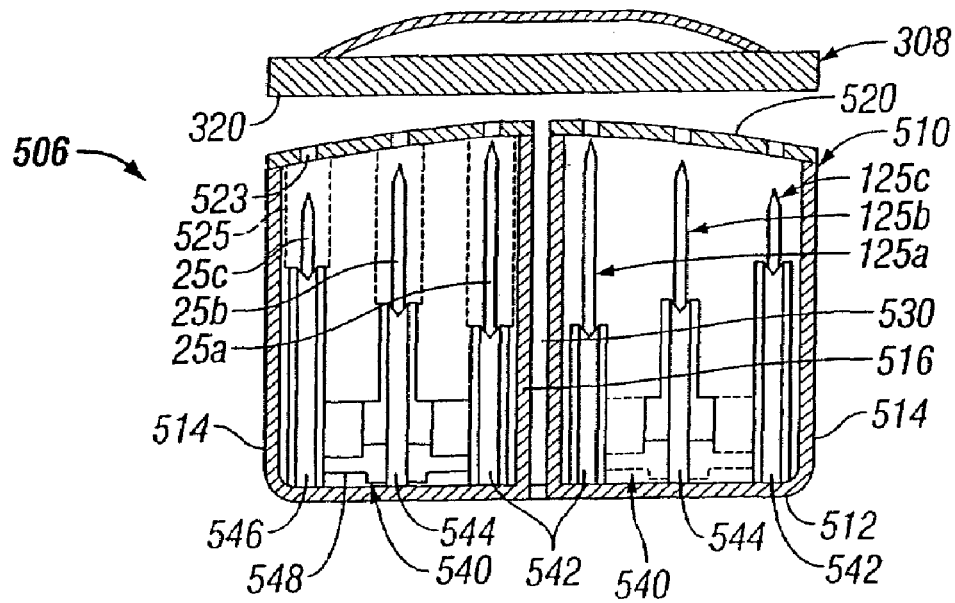
FIG. 9A is a cross-sectional end view of the staple cartridge of FIG. 8 showing a first arrangement of surgical fasteners.
Figure 9B:
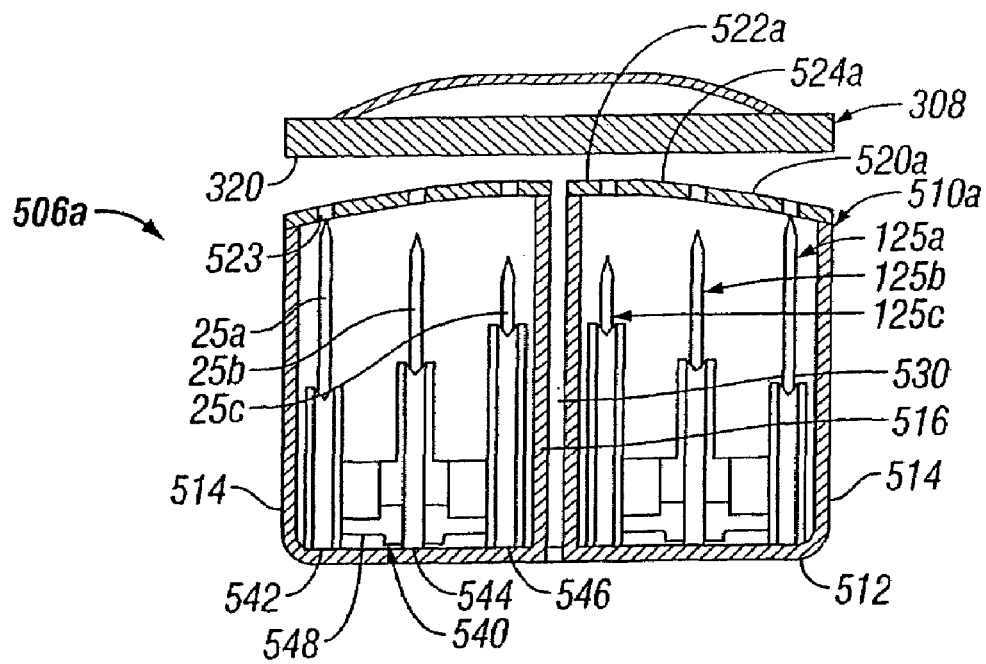
FIG. 9B is a cross-sectional end view of the staple cartridge of FIG. 8 showing a second arrangement of surgical fasteners.
Figure 9C:
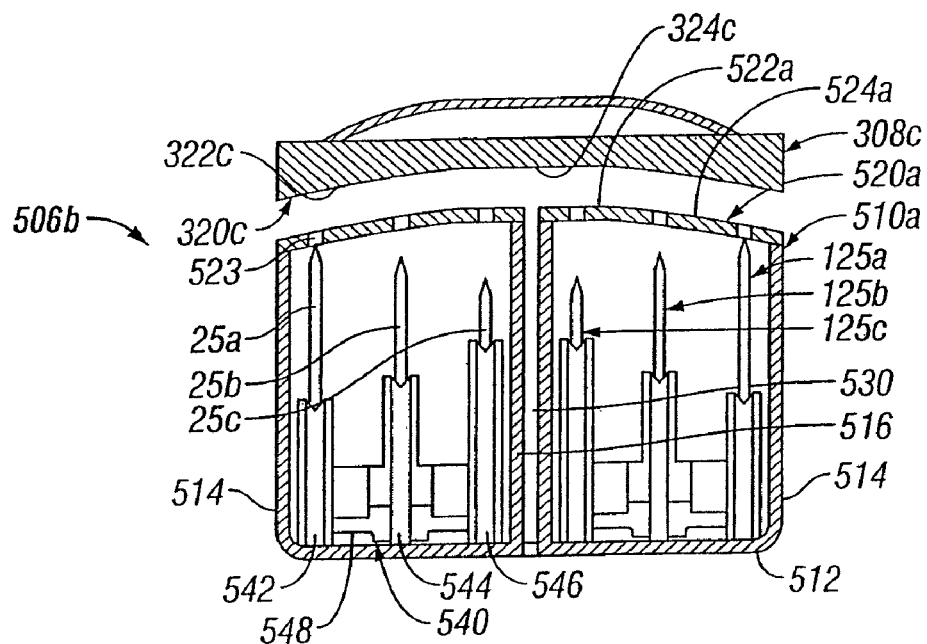
FIG. 9C is an alternate embodiment of the staple cartridge of FIG. 8 showing a second arrangement of surgical fasteners and an alternate embodiment of an anvil member.
Figure 10:
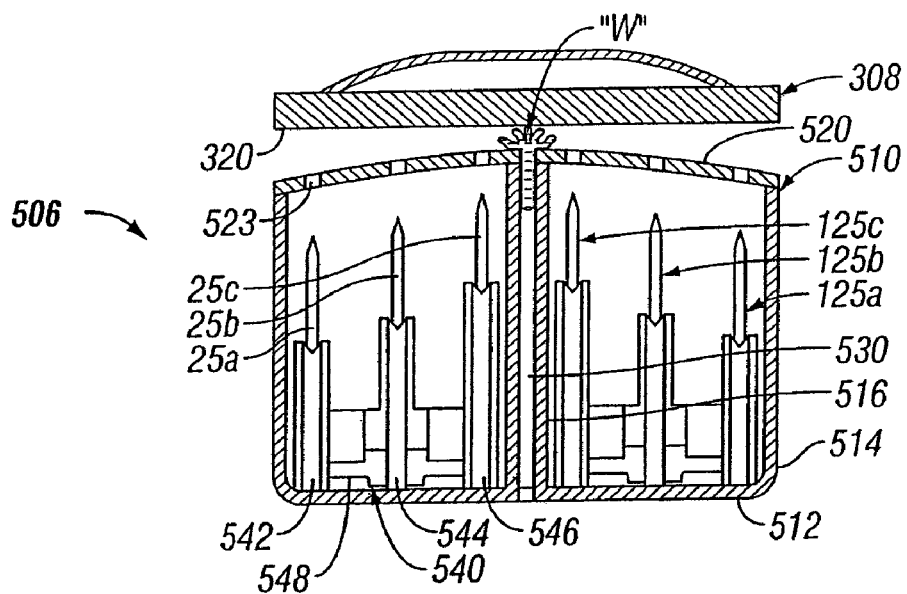
FIG. 10 is an alternate embodiment of the staple cartridge of FIG. 9A illustrating a second embodiment of the surgical fasteners.

In one further embodiment of the present disclosure, as illustrated in FIGS. 8-10, surgical stapling apparatus 300 includes an operative tool 506 disposed at one end of elongated shaft 304. Operative tool 506 includes anvil member 308 and a staple cartridge 510. Staple cartridge 510 may be included in a disposable surgical stapling apparatus or in a reusable surgical stapling apparatus. In particular, staple cartridge 510 includes a tissue contacting surface 520 having a plurality of retention slots 523 disposed therein and arranged in rows that are substantially aligned with a longitudinal axis of staple cartridge 510. As seen in FIG. 8, each row of retention slots 523 is longitudinally offset from an adjacent row of retention slots. In particular, an optional knife channel 530 is disposed along the longitudinal axis of staple cartridge 510 that is adapted for slidably receiving a knife (not shown).

Referring now to FIG. 9A, operative tool 506 is shown in cross-section and illustrates the several components included in staple cartridge 510. Anvil member 308 includes a substantially planar tissue contacting surface 320 that is substantially parallel to a bottom surface 512 or parallel to a plane defined by the backspans of surgical fasteners 125a, 125b, or 125c. Staple cartridge 510 includes outer walls 514 having a first height and inner walls 516 having a second height wherein the second height is greater than the first height. Tissue contacting surface 520 is attached to inner walls 516 and to outer walls 514 and defines an angle with respect to a plane that is orthogonal to inner walls 516. Tissue contacting surface 520 defines a generally curved path between outer walls 514 (i.e. generally convex or elliptical as viewed in cross-section). Additionally, a plurality of surgical fasteners 125a-c are disposed in staple cartridge 510 wherein each row of retention pockets 523 includes a number of substantially identical surgical fasteners (i.e. 125a, 125b, or 125c). Similar to previous embodiments, legs 25a-c of surgical fasteners 125a-c have different lengths. In this embodiment, surgical fasteners 25a have a leg length of about 3.8 mm, surgical fasteners 25b have a leg length of about 3.5 mm, and surgical fasteners 25c have a leg length of about 2.5 mm.

As seen in FIG. 9A, surgical fasteners 125a-c are disposed in staple cartridge 510 such that surgical fasteners 125c are proximate to outer walls 514, surgical fasteners 125a are disposed proximate to inner walls 516, and surgical fasteners 125b are disposed therebetween. In cooperation with the surgical fasteners of varying height, staple cartridge 510 includes fastener ejection members 540 that include staple pushers 542, 544, and 546 of differing heights. Staple pusher 542 has the greatest height dimension, staple pusher 546 has the least height dimension, and staple pusher 544 has a height dimension therebetween. In this embodiment, surgical fasteners 125a-c are arranged to cooperate with staple pushers 546, 544, and 542 respectively. Fastener ejection member 540 is adapted for substantially vertical movement when it cooperatively engages with an actuation mechanism (not shown). An example of a suitable actuation mechanism is disclosed in U.S. Pat. No. 5,865,361 as discussed with reference to previously disclosed surgical stapling instrument 300.

As illustrated in FIG. 9A, fastener ejection member 540 includes staple pushers 542, 544, and 546 that are connected to each other by a connecting member 548, such that all of the pusher plates translate substantially simultaneously through staple cartridge 510. In an alternate embodiment, fastener ejection member 540' includes pusher plates 542, 544, and 546 that are individually set within staple cartridge 510. In this embodiment, each row of staple pushers is individually actuatable and independent of the other rows of staple pushers. Either embodiment of the fastener ejection member 540, 540' may be used in any of the disclosed staple cartridges. Fastener ejection member 540' is illustrated in FIG. 9A and, for the sake of clarity, will not be illustrated in other embodiments of the disclosed surgical stapling apparatus.

In addition, staple cartridge 510 may include a plurality of staple guides or channels 525, shown in phantom, that extend from an inside surface of tissue contacting surface 520 towards fastener ejection member 540 or 540'. In particular, staple channels 525 extend towards staple pushers 542, 544, and 546, and may also vary in height according to their placement within staple cartridge 510. Each staple channel 525 is substantially equal in width to a width of its corresponding staple pusher 542, 544, or 546. Staple channels 525, in cooperation with retention slots 523 form staple pockets and improve the stability of surgical fasteners 125a-c, thereby minimizing lateral or rotational movement of surgical fasteners 125a-c and consequently improving the formation of completed fasteners. Further still, staple channels 525 typically have a shape that corresponds to the shape of staple pushers 542, 544, and 546. For the sake of clarity, staple channels 525 are only illustrated in FIG. 9A, although staple channels 525 may be included in any of the disclosed embodiments of the staple cartridge.

Alternate embodiments of operative tool 506 are illustrated in FIGS. 9B and 9C. These alternate embodiments are identified as operative tool 506a and 506b respectively. Referring initially to FIG. 9B, operative tool 506a includes substantially the same or similar components discussed hereinabove for operative tool 506 with the differences discussed hereinbelow. In contrast to operative tool 506 (FIG. 9A), surgical fasteners 125a-c of operative tool 506a are arranged in staple cartridge 510a such that surgical fasteners 125a are proximate to outer walls 514, surgical fasteners 125c are proximate to inner walls 516, and surgical fasteners 125b are disposed therebetween. In addition, operative tool 506a includes tissue contacting surface 520a that includes first and second surfaces 522a and 524a. Each of first and second surfaces 522a, 524a has a width dimension sufficient to include at least one row of surgical fasteners. First surface 522a is substantially parallel to bottom surface 512, while second surface 524a defines a substantially uniform angle. In particular, second surface 524a extends outwards and downwards from an outer edge of first surface 522a and defines the substantially uniform angle with respect to bottom surface 512.

Turning now to FIG. 9C, operative tool 506b includes staple cartridge 510a that was discussed in reference to FIG. 9B and anvil member 308c. Anvil member 308c includes tissue contacting surface 320c. In particular, tissue contacting surface 320c includes surfaces 322c and 324c. Surface 324c is substantially parallel to bottom surface 512 has a width dimension that is substantially equal to the width dimensions of the first surfaces 522a and knife channel 530, while each surface 322c substantial complements corresponding second surface 524a. This arrangement between the surfaces of anvil member 308c and tissue contacting surface 520a maintains a substantially uniform gap between the surfaces from the centerline of operative tool 506b to its outer walls 514.

Alternatively, as shown in FIG. 10, surgical fasteners 125a-c are disposed in staple cartridge 510' such that surgical fasteners 125a are proximate to outer walls 514, surgical fasteners 125c are disposed proximate to inner walls 516, and surgical fasteners 125b are disposed therebetween. Contrary to the previous embodiment, surgical fasteners 125a-c are arranged to cooperate with staple pushers 542, 544, and 546 respectively. After a number of layers of body tissue are positioned between tissue contacting surfaces 320 and 520, the actuation mechanism is actuated for sequentially ejecting surgical fasteners 125a-c through retention slots 523 whereby interaction between surgical fasteners 125a-c and anvil member 308 forms completed surgical fasteners for joining the layers of body tissue.

When tissue contacting surface 320 of anvil member 308 is repositioned proximate to tissue contacting surface 520 of staple cartridge 510', the amount of pressure applied to the layers of tissue disposed therebetween varies along a plane that is transverse to the longitudinal axis of staple cartridge 510'. Since the distance between tissue contacting surfaces 320 and 520 is at a minimum in the region nearest inner walls 516 (i.e. the centerline of staple cartridge 510'), a maximum pressure is applied to the layers of tissue disposed in this region. Conversely, the distance between tissue contacting surfaces 320 and 520 is at a maximum in the region near outer walls 514, a minimum pressure is applied to the layers disposed in this region. In addition, the proximal relationship between anvil member 308 and staple cartridge 510' defines a plurality of gaps therebetween. A first gap is defined between tissue contacting surfaces 320 and 520 (i.e. along the centerline of staple cartridge 510'), while a second gap is defined between tissue contacting surfaces 320 and 520 along outer walls 514. As seen in FIG. 10, the first gap is not equal to the second gap. Further still, a number of other gaps may be defined between tissue contacting surfaces 320 and 520 at other points of reference existing between the centerline and outer walls 514 in staple cartridge 510'. Since tissue contacting surface 520 slopes toward outer walls 514 to define a substantially uniform angle, the pressure applied to the layers of tissue disposed between tissue contacting surfaces 320 and 520 uniformly decreases from inner wall 516 to outer wall 514.

By angling tissue contacting surface 520 downwards from the centerline of staple cartridge 510', reduced compressive forces are applied to the layers of tissue disposed between tissue contacting surfaces 320 and 520 thereby minimizing trauma to the layers of tissue disposed therebetween. Therefore, layers of tissue disposed between tissue contacting surfaces 320 and 520 will have a minimum thickness nearest knife channel 530 (i.e. nearest the centerline of staple cartridge 510') and a maximum thickness nearest outer walls 514. In addition, anvil member 308 and staple cartridge 510' are dimensioned and arranged such that compressive forces applied to the layers of tissue are minimal thereby further reducing trauma to the layers of tissue. This configuration defines a gap between tissue contacting surfaces 320 and 520 that is a maximum along knife channel 530 (i.e. the centerline of staple cartridge 510 or 510') and a minimum along outer walls of staple cartridge 510 (FIG. 9A) or 510' (FIG. 10).

Further still, this configuration is applicable to similar staple cartridges and anvil members as will be discussed in detail hereinafter with respect to FIGS. 11-15. When anvil member 308' is repositioned into proximity with staple cartridge 510' (i.e. in a pre-fire position) to retain layers of body tissue therebetween, the layers of tissue are compressed. The maximum compression occurs along the centerline (i.e. first or minimum gap) and urges fluid stored in the layers of tissue towards the outer edges of the tissue (i.e. away from the centerline of staple cartridge 510'). By reducing the amount of fluid retained in the layers of tissue proximal to the centerline, the overall thickness of the tissue layers decreases. The decrease in overall tissue thickness is such that a staple having a shorter leg length (i.e. surgical fastener 125c) is capable of fastening both layers of tissue while minimizing trauma to the fastened layers of tissue. The gap increases towards the outer walls of staple cartridge 510' (i.e. the amount of compression decreases) and surgical fasteners having a longer leg length (i.e. surgical fasteners 125a and 125b) are capable of fastening both layers of tissue.

Leg lengths of surgical fasteners 125c, 125b, and 125a increase in a direction moving from inner walls 516 towards outer walls 514. By providing surgical fasteners having increasing leg lengths along a plane that is orthogonal to inner walls 516, the completed (i.e. formed) surgical fasteners join increasing thicknesses of tissue without unduly traumatizing the joined layers of tissue.

Figure 11:
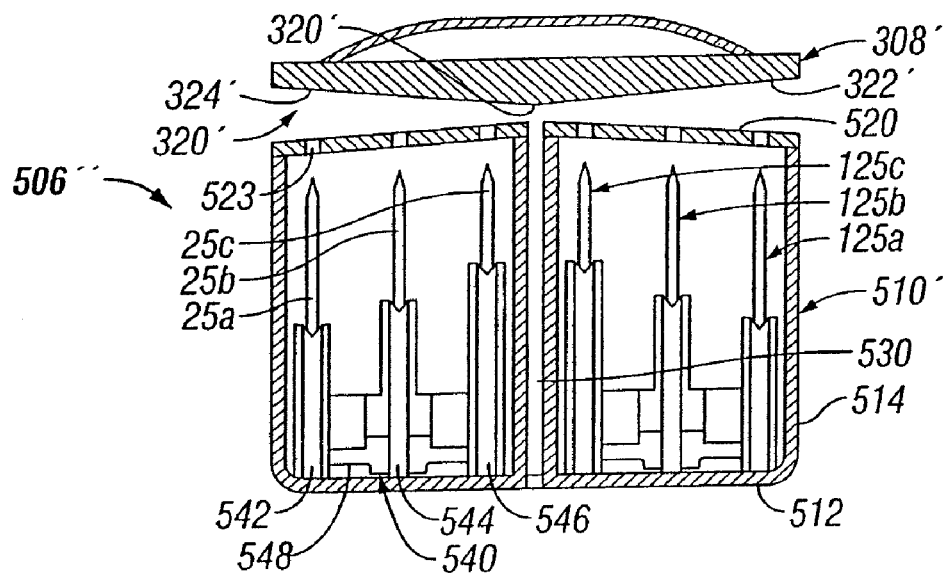
FIG. 11 is an alternate embodiment of an anvil member and the staple cartridge of FIG. 10.

In a further embodiment, as illustrated in FIG. 11, operative tool 506" includes staple cartridge 510' and anvil member 308'. Staple cartridge 510' was previously discussed in detail hereinabove with reference to FIG. 10. Tissue contacting surface 520 may define a more uniform angle (FIG. 11) than in the embodiments of FIGS. 9A and 10 wherein the angle or pitch of tissue contacting surface is substantially constant between inner walls 516 and outer walls 514. Anvil member 308' includes tissue contacting surface 320' having tapered surfaces 322' and 324'. Surfaces 322' and 324' are connected to outer walls of anvil member 308' while extending inwards (i.e. towards the centerline of staple cartridge 510') and downwards (i.e. towards tissue contacting surface 520) thereby defining an angle. It is envisioned that the angle defined by tapered surfaces 322' and 324' will be substantially similar to the angle defined by tissue contacting surface 520, but in an opposed direction forming a generally V-shaped configuration. Thus, compressive forces applied to the layers of tissue will be further reduced thereby further reducing the trauma to layers of tissue disposed between tissue contacting surfaces 520 and 320'. As in the embodiment of FIG. 10, the maximum pressure applied to the layers of tissue will exist in the region near knife channel 530 while pressures applied to the layers of tissue will decrease uniformly towards outer walls 514. Formation and location of surgical fasteners 125a-c is substantially similar to that of the embodiment of FIG. 10 along with the attendant advantages.

Figure 12:
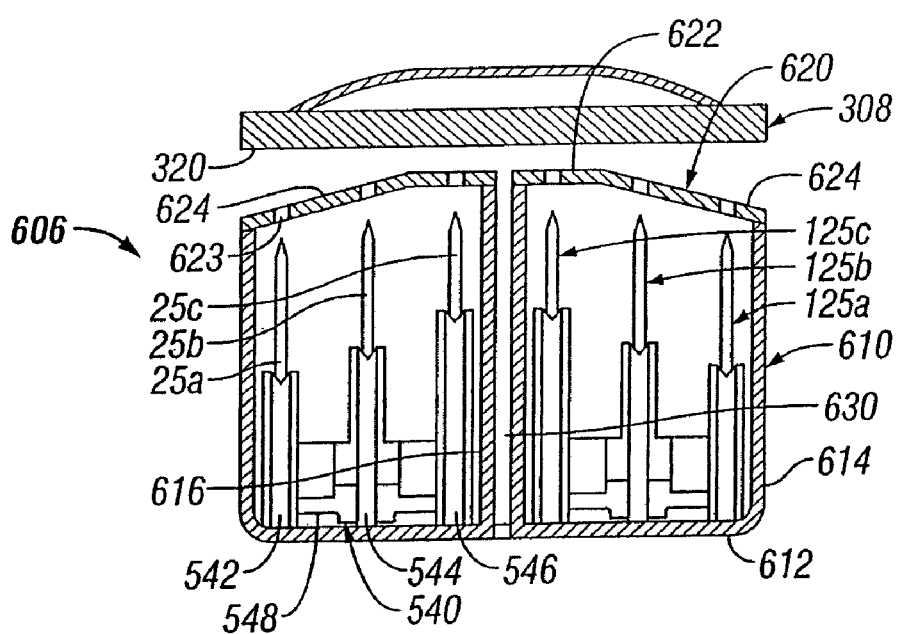
FIG. 12 is a further embodiment of the staple cartridge of FIG. 8.

Referring now to FIG. 12, a further embodiment of the present disclosure is shown as part of operative tool 606. Operative tool 606 includes a staple cartridge 610 and anvil member 308. In this embodiment, tissue contacting surface 620 includes surfaces 622 and 624. Surface 622 is bisected along its longitudinal axis by knife channel 630 and substantially parallel to a bottom surface 612 or parallel to a plane defined by the backspans of surgical fasteners 125a, 125b, or 125c. In addition, surface 622 has a width dimension sufficient to accommodate at least one row of retention slots 623 on each side of knife channel 630. Surface 624 connects outer edges of surface 622 to outer walls 614 defining an angle on either side of knife channel 630 with respect to a plane that is substantially orthogonal to inner walls 616 (i.e. substantially parallel to surface 622) and has a width dimension sufficient to accommodate at least one row of retention slots on each side of knife channel 630. Staple cartridge 610 includes a plurality of surgical fasteners 125a-c and fastener ejection members 540 that were previously discussed in detail with respect to FIGS. 9A and 10. In particular, staple cartridge 610 includes the arrangement of surgical fasteners 125a-c and fastener ejection members 540 as described with respect to staple cartridge 510' (FIGS. 10 and 11).

Similar to operative tool 506, tissue contacting surface 320 is repositioned proximate to tissue contacting surface 620 of staple cartridge 610. In this arrangement, the amount of pressure applied to the layers of tissue disposed therebetween varies along a plane that is transverse to the longitudinal axis of staple cartridge 610. Specifically, the distance between tissue contacting surface 320 and surface 622 is a minimum, a maximum pressure is applied to the layers of tissue disposed in this region. Conversely, the distance between tissue contacting surface 320 and surfaces 624 is at a maximum in the region near outer walls 614, a minimum pressure is applied to the layers disposed in this region. Since surface 624 slopes toward outer walls 614 to define a substantially uniform angle, the pressure applied to the layers of tissue disposed between tissue contacting surface 320 and surfaces 624 uniformly decreases from an outer edge of surface 622 towards outer wall 614.

By angling surface 624 downwards from the edge of surface 622, reduced compressive forces are applied to the layers of tissue disposed between tissue contacting surface 320 and surfaces 624 thereby minimizing trauma to the layers of tissue disposed therebetween. Layers of tissue disposed between tissue contacting surfaces 320 and 620 will have a minimum thickness nearest knife channel 630 and a maximum thickness nearest outer walls 614. In addition, anvil member 308 and staple cartridge 610 are dimensioned and arranged such that compressive forces applied to the layers of tissue are minimal thereby further reducing trauma to the layers of tissue.

Leg lengths of surgical fasteners 125c, 125b, and 125a increase in a direction moving from inner walls 616 towards outer walls 614. By providing surgical fasteners having increasing leg lengths along a plane that is orthogonal to inner walls 616, the completed (i.e. formed) surgical fasteners join increasing thicknesses of tissue without unduly traumatizing the joined layers of tissue.

Figure 13:
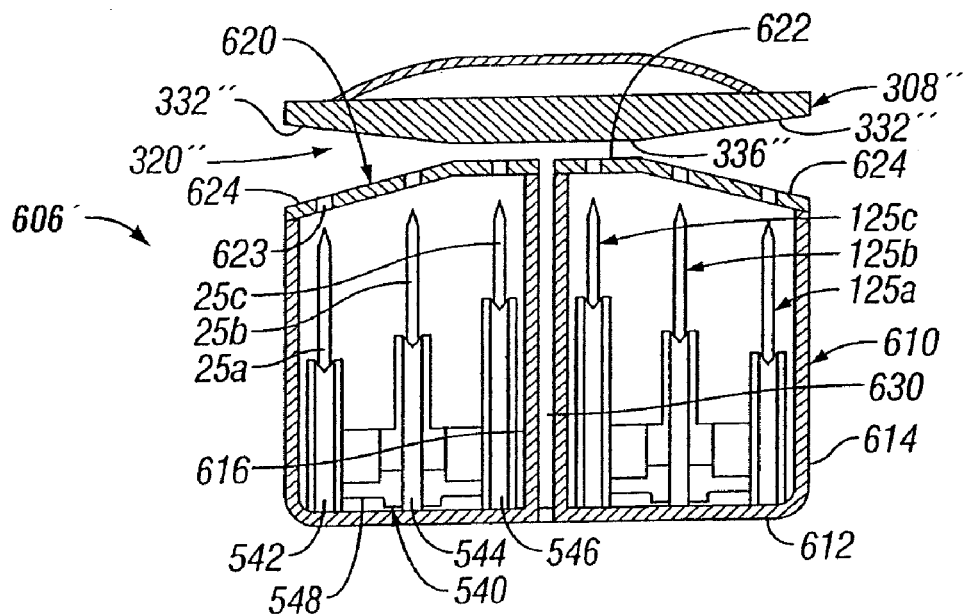
FIG. 13 is another embodiment of the anvil member and the staple cartridge of FIG. 12.

In a further embodiment, operative tool 606' is illustrated in FIG. 13. Operative tool 606' includes staple cartridge 610, that was described in detail hereinabove with respect to FIG. 12, and anvil member 308". Anvil member 308" includes a tissue contacting surface 320" formed from surfaces 332" and 336". Surface 336" is substantially parallel to surface 622 and has a width dimension that is substantially similar to the width dimension of surface 622. Surfaces 332" are tapered and connected to outer walls of anvil member 308" and extend inwards (i.e. towards the centerline of staple cartridge 610) and downwards (i.e. towards tissue contacting surface 620) thereby defining an angle. It is envisioned that the angle defined by tapered surfaces 332" will be substantially similar to the angle defined by surfaces 624, but in an opposed direction. Thus, compressive forces applied to the layers of tissue will be further reduced thereby further reducing the trauma to layers of tissue disposed between surfaces 624 and 332". As in the embodiment of FIG. 10, the maximum pressure applied to the layers of tissue will exist in the region along surface 622 while pressures applied to the layers of tissue will decrease uniformly along surfaces 624 towards outer walls 614. Formation and location of surgical fasteners 125a-c is substantially similar to that of the embodiment of FIG. 12 along with the attendant advantages.

Figure 14:
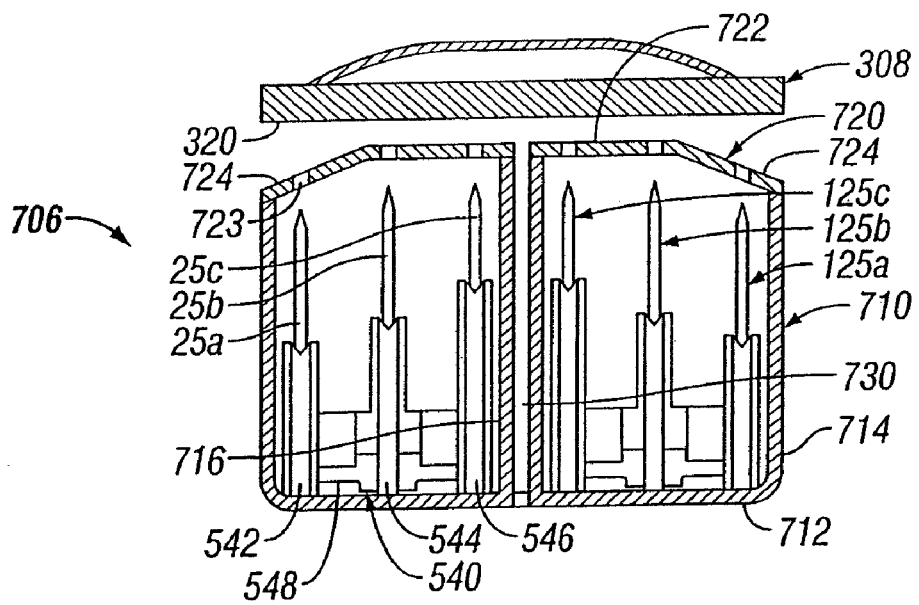
FIG. 14 is another embodiment of the staple cartridge and anvil member of FIG. 8.

In yet another embodiment, operative tool 706 is illustrated in FIG. 14. Staple cartridge 710 is similar to staple cartridge 610. The differences between staple cartridges 610 and 710 will be discussed hereinafter. As in staple cartridge 610 (FIG. 12), staple cartridge 710 includes tissue contacting surface 720 formed from surfaces 722 and 724. Surface 722 differs from surface 622 in that it has a width dimension sufficient to accommodate at least two rows of surgical fasteners. As in staple cartridge 610, surfaces 724 are attached to outer edges of surface 722 and outer walls 714 to define angles. The interaction between staple cartridge 710 and anvil member 308 for capturing tissue and forming surgical fasteners is substantially similar to the interaction between staple cartridge 610 and anvil member 308 and, for the sake of brevity, will not be repeated herein.

Figure 15:
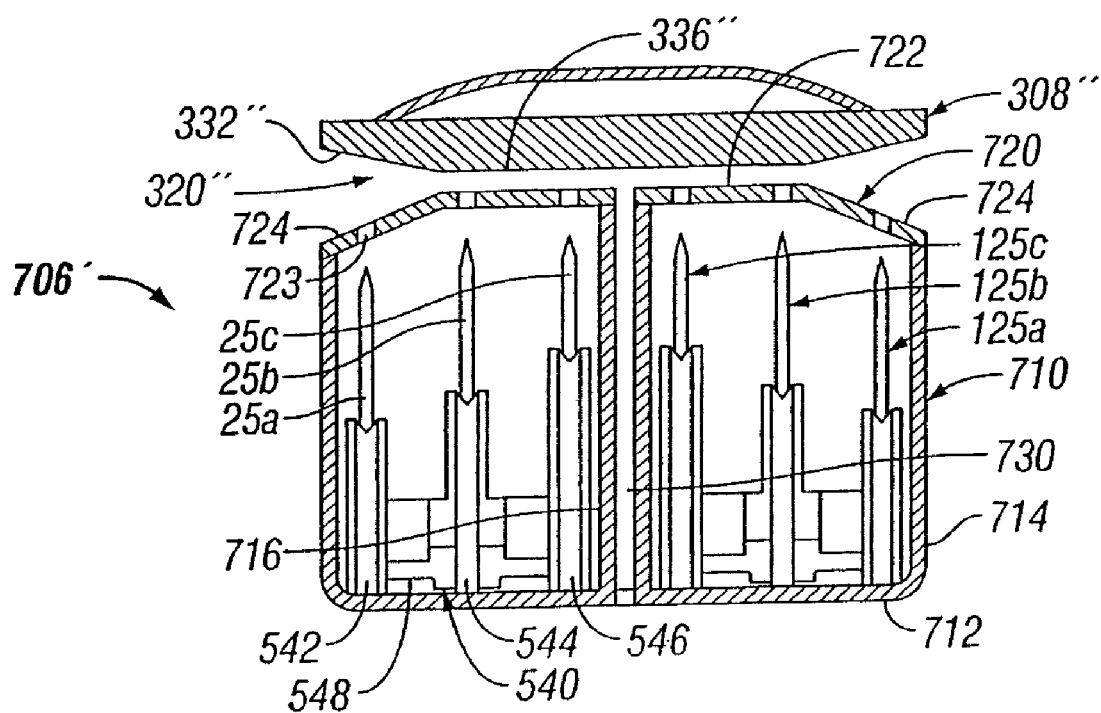
FIG. 15 is alternate embodiment of an anvil member with the staple cartridge of FIG. 14.

In FIG. 15, an alternate embodiment of operative tool 706' is illustrated. Operative tool 706' includes staple cartridge 710, as discussed in detail hereinabove, and anvil member 308". Anvil member 308" includes a tissue contacting surface 320" formed from surfaces 332" and 336". Surface 336" is substantially parallel to surface 722 and has a width dimension that is substantially similar to a width dimension of surface 722. Surfaces 332" are tapered and connected to outer walls of anvil member 308" and extend inwards (i.e. towards centerline of staple cartridge 710) and downwards (i.e. towards tissue contacting surface 720) thereby defining an angle. It is envisioned that the angle defined by tapered surfaces 332" will be substantially similar to the angle defined by surfaces 724, but in an opposed direction. Thus, compressive forces applied to the layers of tissue will be further reduced, thereby further reducing the trauma to the layers of tissue disposed between surfaces 724 and 332". As in the embodiment of FIG. 14, the maximum pressure applied to the layers of tissue will exist in the region along surface 722 while pressures applied to the layers of tissue will decrease uniformly along surfaces 724 towards outer walls 714. Formation and location of surgical fasteners 125a-c is substantially similar to that of the embodiment of FIG. 14 along with the attendant advantages.

Turning now to FIG. 16B, a cross-section of the resulting tissue interface, following the firing of staple cartridge 510', is shown. As seen in FIG. 16B, the tissue interface has a substantially tapered profile. In particular, some or all of surgical fasteners 125a-125c serve to hold tissues "A" and "B" to one another while surgical fasteners 125c also provide the hemostasis. This resulting cross-section is also applicable to the firing of staple cartridges 610 and 710. When staple cartridge 510 is fired, some or all of surgical fasteners 125a-5c serve to hold tissues "A" and "B" to one another while surgical fasteners 125a also provide the hemostasis. When layers of tissue "A" and "B" are fastened using a conventional surgical stapling device and conventional staples "S", there exists a sharp transition from the un-fastened layers of tissue to the fastened layers of tissue that is illustrated in FIG. 16A. This may result in a greater load being placed on the layers of tissue and may produce an undesirable effect on the layers of tissue. In comparison, as shown in FIG. 16B, the tissue interface has a gradual transition from the un-fastened layers of tissue to the fastened layers of tissue and also within the fastened layers of tissue. This arrangement provides gradual tissue loading or compression due to the varying sizes of the formed surgical fasteners 125a-c, thereby minimizing tissue trauma while maintaining a relatively high degree of hemostasis and anastomotic strength.

In a further embodiment of the present disclosure, as shown in FIGS. 8 and 10, operative tool 506' includes a wound closure assembly 50. Wound closure assembly 50 includes at least one storage device or reservoir 52 and at least one supply line 54. Supply line 54 fluidly couples reservoir 52 to staple cartridge 510' for delivering an amount of a wound closure material "W". In particular, supply line 54 delivers wound closure material "W" into knife channel 530 such that when surgical fasteners 125a-c are formed, wound closure material "W" migrates along the layers of tissue adjacent to tissue contacting surface 520 (i.e. the target site). By providing wound closure material "W" in combination with surgical fasteners 125a-c, the bond formed between the layers of tissue has improved strength.

Compression of reservoir 52 causes wound closure material "W" contained therein to be urged through supply line 54 and dispensed via knife channel 530. Preferably, wound closure material "W" is dispensed during the staple firing procedure so that wound closure material "W" is dispensed along the length of the staple line and/or a knife cut line. Although wound closure assembly is discussed and illustrated with respect to FIG. 10, it is contemplated that wound closure assembly 50 is adaptable for use with other disclosed embodiments of staple cartridge 510' (i.e. 510, 610, or 710). It is further contemplated that an additional reservoir may be included for wound closure materials formed by combining two substances or that reservoir 52 may include a plurality of internal chambers (shown in phantom) for storing quantities of substances to be combined to form wound closure material "W".

It is envisioned that wound closure material "W" can include one or a combination of adhesives, hemostats, sealants. Surgical biocompatible wound closure materials which can be employed in or applied the surgical instruments, especially surgical staplers, include adhesives whose function is to attach or hold organs, tissues or structures, sealants to prevent fluid leakage, and hemostats to halt or prevent bleeding. Examples of adhesives which can be employed include protein derived, aldehyde-based adhesive materials, for example, the commercially available albumin/glutaraldehyde materials sold under the trade designation BIOGLUE™ by Cryolife, Inc., and cyanoacrylate-based materials sold under the trade designations INDERMIL™ and DERMA BOND™ by Tyco Healthcare Group, LP and Ethicon Endosurgery, Inc., respectively. Examples of sealants, which can be employed, include fibrin sealants and collagen-based and synthetic polymer-based tissue sealants. Examples of commercially available sealants are synthetic polyethylene glycol-based, hydrogel materials sold under the trade designation COSEAL™ by Cohesion Technologies and Baxter International, Inc. Examples of hemostat materials, which can be employed, include fibrin-based, collagen-based, oxidized regenerated cellulose-based and gelatin-based topical hemostats. Examples of commercially available hemostat materials are fibrinogen-thrombin combination materials under sold the trade designations COSTASIS™ by Tyco Healthcare Group, LP, and TISSEEL™ sold by Baxter International, Inc. Hemostats herein include astringents, e.g., aluminum sulfate, and coagulants.

It is to be understood that the dispensing of wound closure material "W" can be as a fluid spray of any suitable volume, including a mist, applied temporarily, continuously, or continually. Particulate material, e.g. a fine powder is contemplated to be a fluid within the scope of this disclosure.

It is provided that a number of different wound closure materials "W" can be dispensed by wound closure assembly 50 or a combination of the number of different wound closure materials "W". The wound closure material dispensed by wound closure assembly 50 can, for example, be an astringent, such as a sulfate of aluminum, which causes small blood vessels to close and helps the blood to coagulate. It is provided that wound closure material "W" can be an astringent provided in the material commercially available under the trade designation NO NIX® Styptic Pencils from Requa, Inc.

Figure 17A:
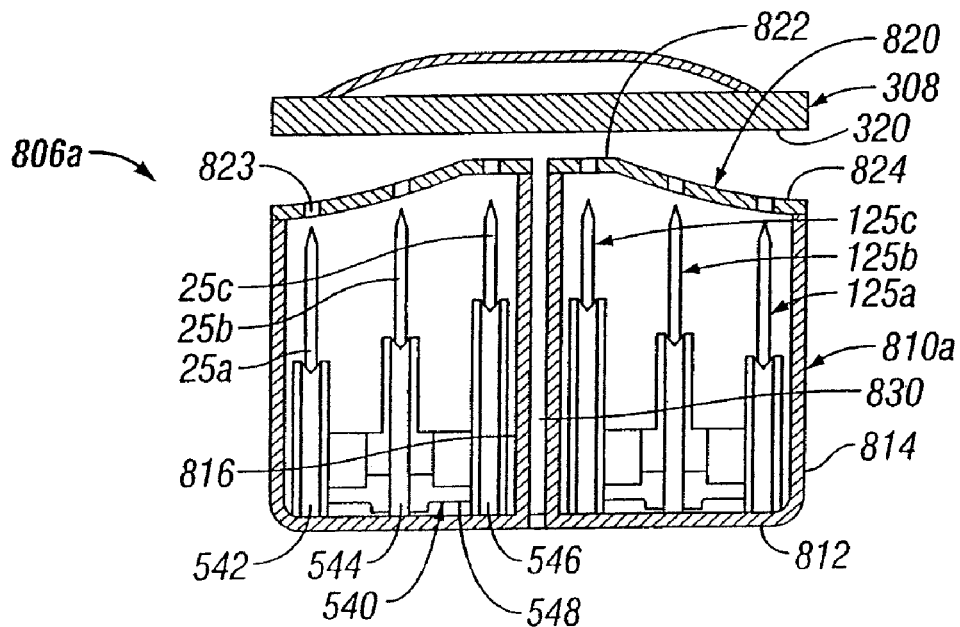
FIG. 17A is a cross-sectional end view of another embodiment of the staple cartridge of FIG. 8 showing a first arrangement of surgical fasteners.

Referring now to FIGS. 17A-F, further embodiments of the presently disclosed operative tool are illustrated. As shown in FIG. 17A, operative tool 806a includes anvil member 308 and staple cartridge 810a. Anvil member 308 was previously described hereinabove with reference to FIG. 9A and, for the sake of brevity, will not be discussed again. In addition, staple cartridge 810a is similar to staple cartridge 710 (FIG. 14) with the differences being discussed in detail hereinbelow. Similar to staple cartridge 710, staple cartridge 810a includes a tissue contacting surface 820, outer and inner walls 814, 816, a knife channel 830, and a bottom surface 812. Located within staple cartridge 810a is a plurality of surgical fasteners 125a, 125b, and 125c that were previously discussed with respect to staple cartridge 710. In addition, staple cartridge 810a includes a plurality of fastener ejection members 540 that were previously described with respect to FIG. 9.

In this embodiment, surfaces 822 and 824 define tissue contacting surface 820. As with previous embodiments of the presently disclosed staple cartridge, tissue contacting surface 820 includes a plurality of retention slots 823. Surface 822 is a planar surface that is substantially parallel to bottom surface 812, while surface 824 is a generally arcuate surface. Each surface 822, 824 includes at least one row of retention slots 823. Additionally, inner wall 816 has a first height and outer wall 814 has a second height, wherein the first height is greater than the second height. One edge of surface 824 is attached to outer wall 814 while the opposing edge is attached to an edge of surface 822, thereby defining a generally concave surface with respect to surface 822.

Similar to previous embodiments of the presently disclosed operative tool, tissue contacting surface 320 of anvil member 308 is repositioned proximate to tissue contacting surface 820 of staple cartridge 810*a*. In this arrangement, the amount of pressure applied to the layers of tissue disposed therebetween varies along a plane that is transverse to the longitudinal axis of staple cartridge 810*a*. Specifically, the distance between tissue contacting surface 320 and surface 822 is a minimum, such that a maximum pressure is applied to the layers of tissue disposed in this region. Conversely, the distance between tissue contacting surface 320 and surfaces 824 is at a maximum in the region near outer walls 814, such that a minimum pressure is applied to the layers disposed in this region. Since surface 824 curves downward as it approaches outer walls 814, the pressure applied to the layers of tissue disposed between tissue contacting surface 320 and surfaces 824 decreases from an outer edge of surface 822 towards outer wall 814. The amount of pressure decrease is a function of curvature of surface 824.

By curving surface 824 downwards from the edge of surface 822, reduced compressive forces are applied to the layers of tissue disposed between tissue contacting surface 320 and surfaces 824 thereby minimizing trauma to the layers of tissue disposed therebetween. Layers of tissue disposed between tissue contacting surfaces 320 and 820 will have a minimum thickness nearest knife channel 830 and a maximum thickness nearest outer walls 814. In addition, anvil member 308 and staple cartridge 810*a* are dimensioned and arranged such that compressive forces applied to the layers of tissue are minimal thereby further reducing trauma to the layers of tissue.

Leg lengths of surgical fasteners 125*c*, 125*b*, and 125*a* increase in a direction moving from inner walls 816 towards outer walls 814. By providing surgical fasteners having increasing leg lengths along a plane that is orthogonal to inner walls 816, the completed (i.e. formed) surgical fasteners join increasing thicknesses of tissue without unduly traumatizing the joined layers of tissue. A more detailed description of surgical fasteners 125*a-c* and fastener ejection members 540 is discussed hereinabove with reference to FIG. 9.

In the embodiment illustrated in FIG. 17B, operative tool 806*b* includes staple cartridge 810*b* that is substantially similar to staple cartridge 810*a* with the differences between them being discussed below. In staple cartridge 810*b*, outer walls 814' and inner walls 816' have a lower height than outer walls 814 and inner walls 816 of staple cartridge 810*a*. In this configuration, tissue contacting surface 820 is closer to bottom surface 812 such that tips of surgical fasteners 125*a*, 125*b*, and 125*c* extend into retention slots 823 and are substantially flush with tissue contacting surface 820.

Figure 17B:
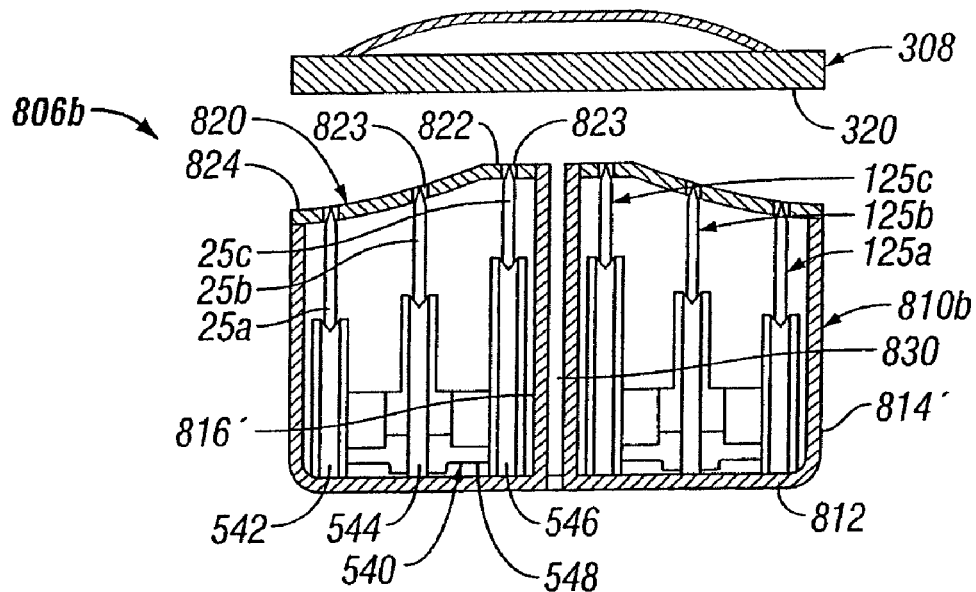
FIG. 17B is an alternate embodiment of the staple cartridge of FIG. 17A showing a second arrangement of surgical fasteners.
Figure 17C:
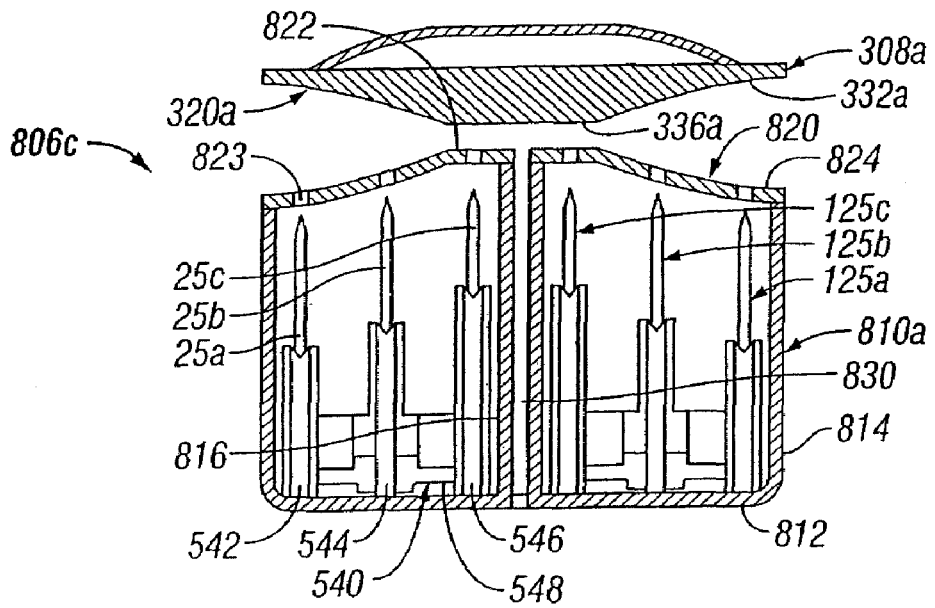
FIG. 17C is an alternate embodiment of an anvil member and the staple cartridge of FIG. 17A.
Figure 17D:
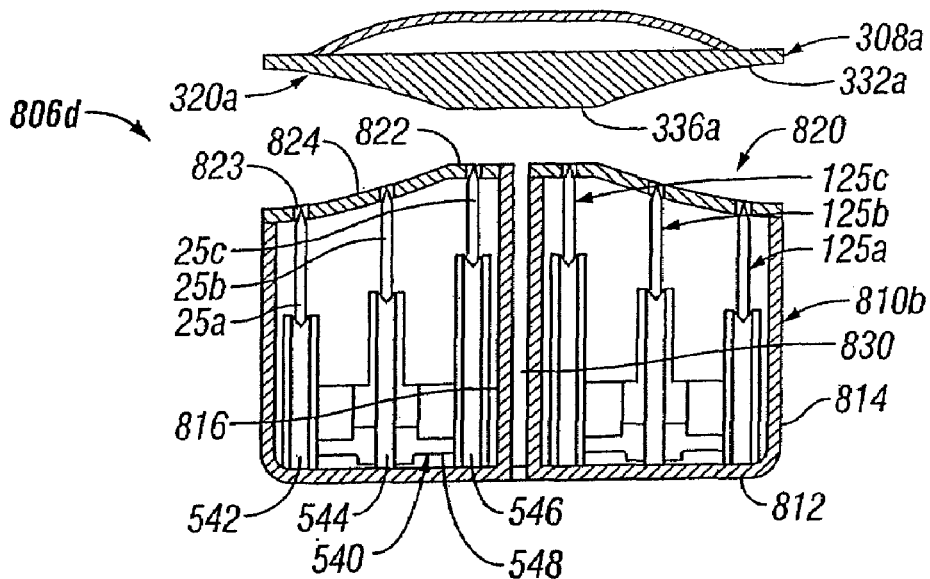
FIG. 17D is an alternate embodiment of an anvil member and the staple cartridge of FIG. 17B.

Referring now to FIGS. 17C and 17D, operative tools 806*c* and 806*d* are illustrated. Operative tools 806*c* and 806*d* include staple cartridges 810*a* and 810*b* (as discussed hereinabove) respectively. In these embodiments, anvil member 308*a* replaces anvil member 308. In this embodiment, anvil member 308*a* includes a tissue contacting surface 320*a* formed from surfaces 332*a* and 336*a*. Surface 336*a* is substantially parallel to surface 822 and has a width dimension that is substantially similar to the width dimension of surface 822. Surfaces 332*a* are generally arcuate such that a thickness of anvil member 308*a* is at a minimum in the region near its outer edge and a maximum along surface 336*a*. It is envisioned that the curve defined by surfaces 332*a* will be substantially similar to the curve defined by surfaces 824, but in an opposed direction (i.e. defining a convex relationship with respect to surface 822). Thus, compressive forces applied to the layers of tissue will be further reduced, thereby further reducing trauma to the layers of tissue positioned between surfaces 824 and 332*a*.

As in the embodiment of FIGS. 17A and 17B, the maximum pressure applied to the layers of tissue will exist in the region along surface 822 while pressures applied to the layers of tissue will decrease along surfaces 824 towards outer walls 814, 814'. The decrease in pressure along the gradient defined by surfaces 824 and 332*a* is proportional to the curvature of each surface. Formation and location of surgical fasteners 125*a-c* is substantially similar to that of the embodiment of FIGS. 17A and 17B along with the attendant advantages.

Figure 18A:
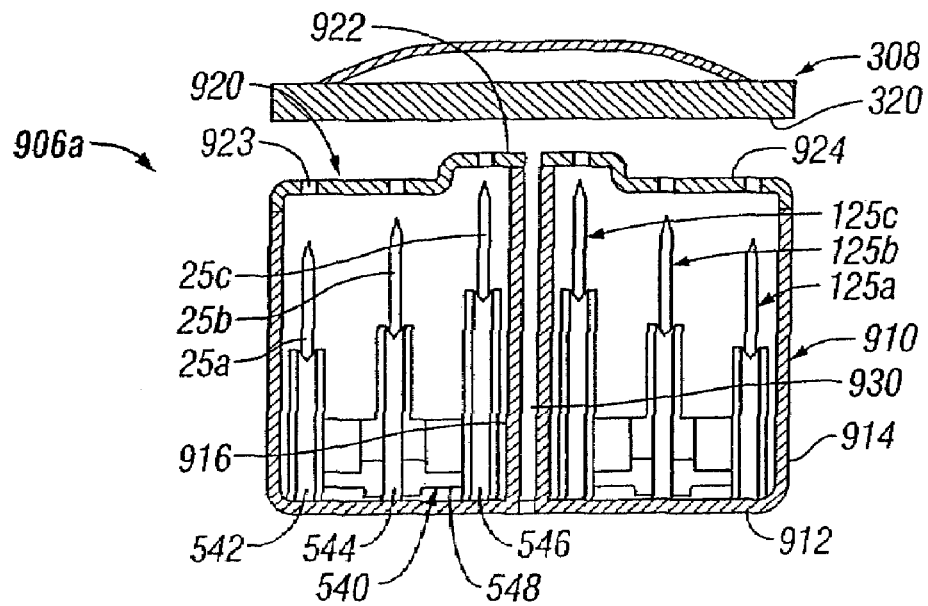
FIG. 18A is a cross-sectional end view of a further embodiment of the staple cartridge of FIG. 8.

In a further embodiment, operative tool 906 is illustrated in FIG. 18A. Operative tool 906 includes anvil member 308 and staple cartridge 910. Staple cartridge 910 is substantially similar to staple cartridge 810 wherein the same or similar components are renumbered accordingly and the differences discussed in detail hereinafter. Tissue contacting surface 920 includes surfaces 922 and 924 wherein each surface includes a plurality of retention slots 923. Similar to the embodiment shown in FIGS. 17A-D, surface 922 is a generally planar surface that is substantially parallel to a bottom surface 912 and defines a right angle at its junction with inner wall 916. Surface 924 is also a generally planar surface that substantially parallel with bottom surface 912 and surface 922, wherein surfaces 922 and 924 are vertically spaced apart such that they are not coplanar with one another. Additionally, inner wall 916 has a first height and outer wall 914 has a second height, wherein the first height is greater than the second height.

As in the previous embodiments of the presently disclosed operative tool, tissue contacting surface 320 of anvil member 308 is repositioned proximate to tissue contacting surface 920 of staple cartridge 910. In this arrangement, the amount of pressure applied to the layers of tissue disposed therebetween varies along a plane that is transverse to the longitudinal axis of staple cartridge 910. Specifically, the distance between tissue contacting surface 320 and surface 922 is a minimum, such that a maximum pressure is applied to the layers of tissue disposed in this region. Conversely, the distance between tissue contacting surface 320 and surfaces 824 is at a maximum, such that a minimum pressure is applied to the layers disposed in this region. Since surface 924 is generally planar, the pressure applied to the layers of tissue disposed between tissue contacting surface 320 and surfaces 924 is substantially uniform and less than the pressure applied to the layers of tissue positioned between tissue contacting surface 320 and surface 922.

Leg lengths of surgical fasteners 125*c*, 125*b*, and 125*a* increase in a direction moving from inner walls 916 towards outer walls 914. By providing surgical fasteners having increasing leg lengths along a plane that is orthogonal to inner walls 916, the completed (i.e. formed) surgical fasteners join increasing thicknesses of tissue without unduly traumatizing the joined layers of tissue. A more detailed description of surgical fasteners 125*a-c* and fastener ejection members 540 is discussed hereinabove with reference to FIG. 9.

Figure 17E:
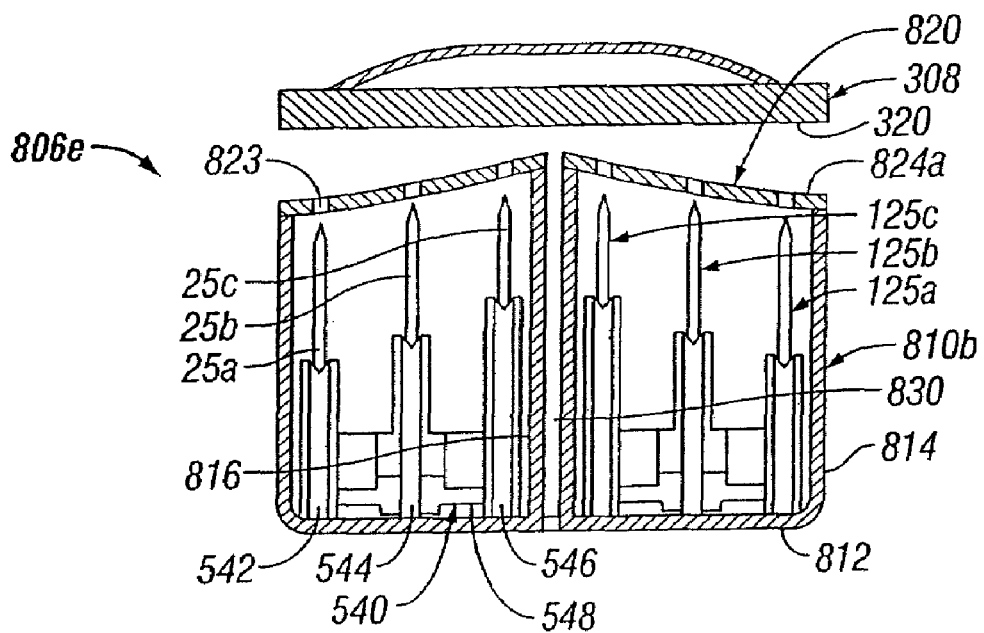
FIG. 17E is a further embodiment of the staple cartridge of FIG. 17A.

Referring now to FIG. 17E, a further embodiment of operative tool 806 is illustrated and referenced as operative tool 806*e*. Operative tool 806*e* includes substantially the same or similar components as operative tool 806*a* (FIG. 17A) with the differences being discussed hereinafter. In particular, operative tool 806*e* includes anvil member 308 and staple cartridge 810*b*. Staple cartridge differs from staple cartridge 810*a* in that tissue contacting surface 824*a* is an arcuate structure extending from the centerline to outer walls 514 of staple cartridge 810*b*. The arrangement between tissue contacting surface 824a and tissue contacting surface 320 provides the same advantages and benefits as does the arrangements provided in the embodiments illustrated in FIGS. 17A-D.

Figure 17F:
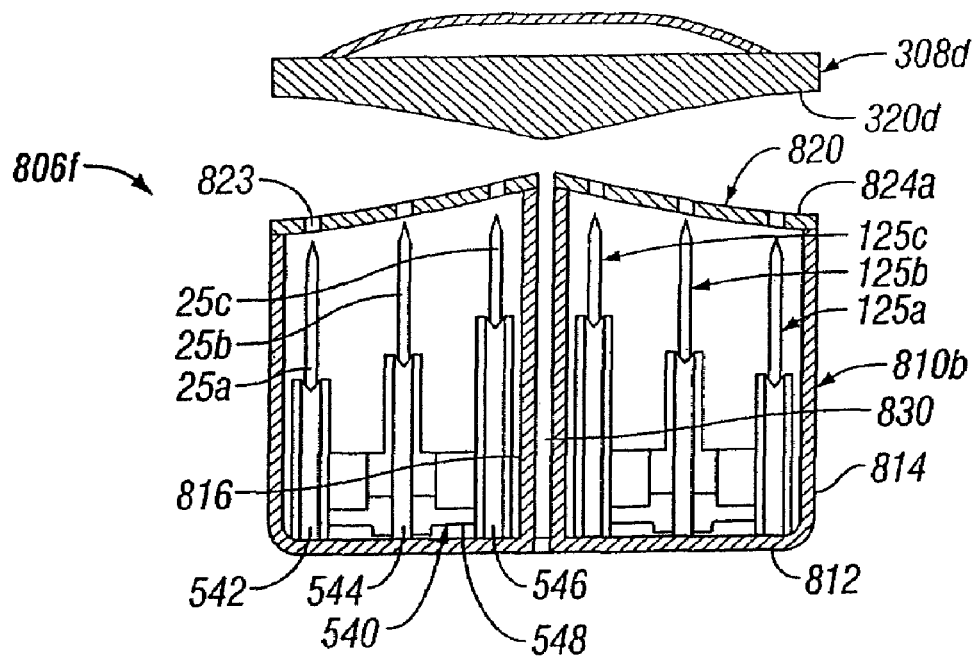
FIG. 17F is an alternate embodiment of an anvil member and the staple cartridge of FIG. 17E.

Alternatively, staple cartridge 810b may be used with anvil member 308d to form operative tool 806f that is illustrated in FIG. 17F. Anvil member 308d includes tissue contacting surface 320d that is substantially complementary to tissue contacting surface 824a. In this configuration, a substantially uniform gap is maintained between the surfaces from the centerline of operative tool 806f to its outer walls 814.

Figure 18B:
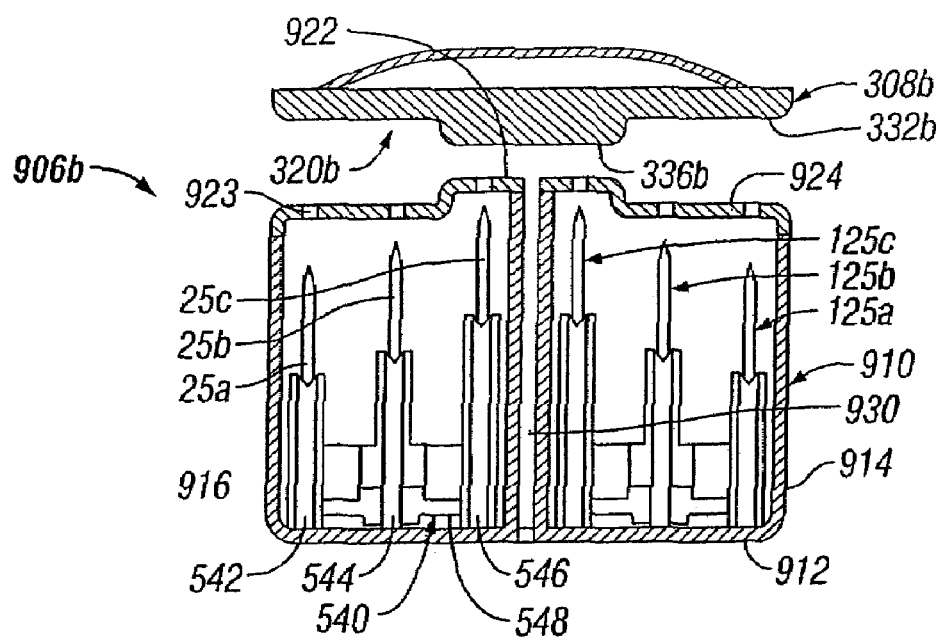
FIG. 18B is an alternate embodiment of an anvil member and the staple cartridge of FIG. 18A.

A further embodiment of the presently disclosed operative tool is illustrated in FIG. 18B wherein anvil member 308 is replaced by anvil member 308b. Operative tool 906a includes staple cartridge 910 and anvil member 308b. In particular, anvil member 308b includes a tissue contacting surface 320b that is defined by surfaces 332b and 336b. Similar to the embodiment shown in FIG. 17D, tissue contacting surface 320b of anvil member 308b is complementary to tissue contacting surface 920 of staple cartridge 910 such that a greater gap is defined between surfaces 924 and 332b than between surfaces 924 and tissue contacting surface 320 (FIG. 18A). In this configuration, a reduced amount of pressure is applied to the layers of tissue captured therebetween.

Figure 19A:
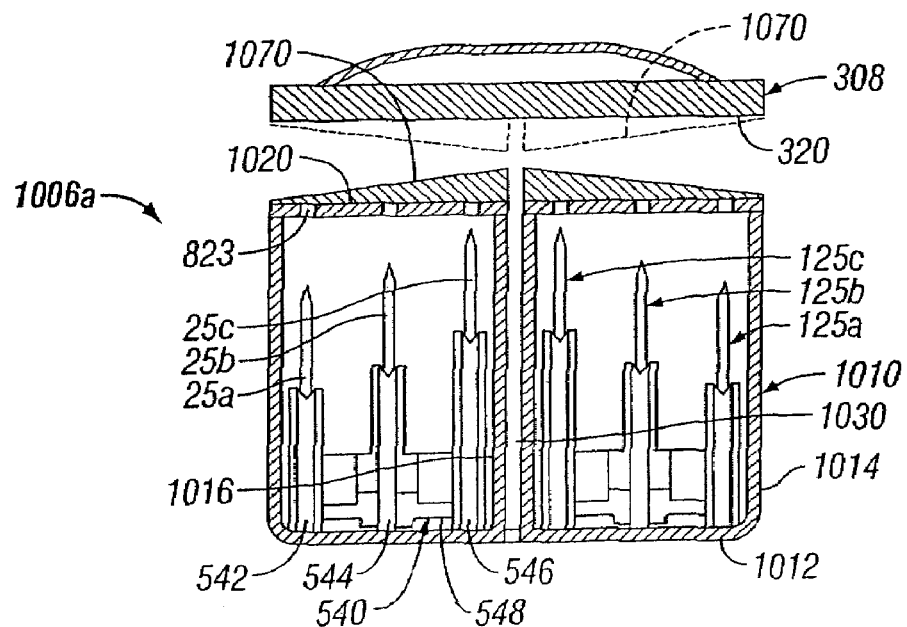
FIG. 19A is a cross-sectional end view of a further embodiment of the staple cartridge of FIG. 8 illustrating a shaped support member disposed on a tissue contacting surface of the staple cartridge and a shaped support member, in phantom, disposed on a tissue contacting surface of the anvil member.
Figure 19B:
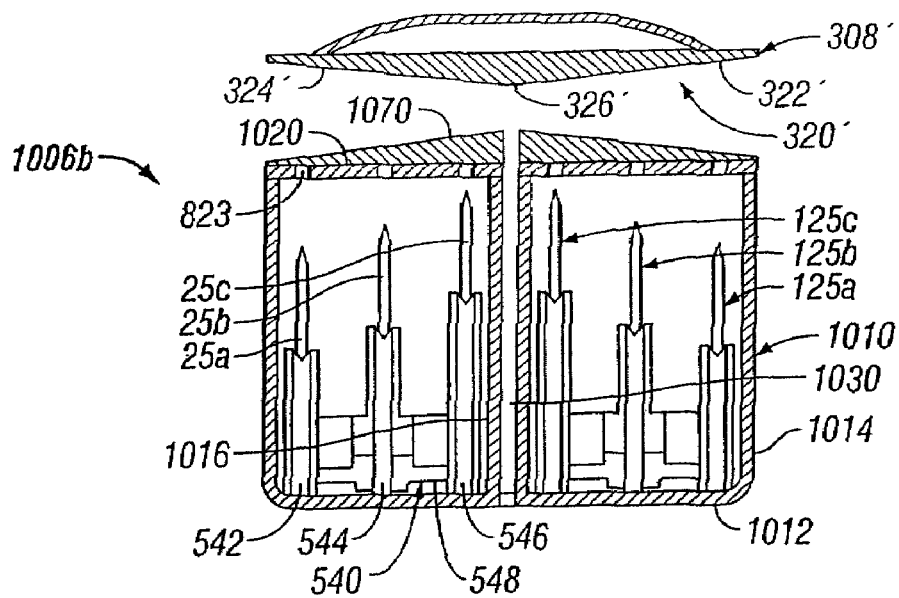
FIG. 19B is an alternate embodiment of an anvil member and the staple cartridge of FIG. 19A.

Referring now to FIGS. 19A and 19B, operative tools 1006a and 1006b are illustrated. Operative tool 1006a includes anvil member 308 and a staple cartridge 1010. Staple cartridge 1010 is substantially similar to staple cartridge 510 wherein the same or similar components are renumbered accordingly and the differences discussed in detail hereinafter. Surface 1020 is substantially planar and substantially parallel to bottom surface 1012. In this embodiment, a filler layer 1070 is positioned on surface 1020. Filler layer 1070 is formed from a material that has sufficient resiliency to support layers of tissue while permitting surgical fasteners 125a-c to pass through during the formation of completed surgical fasteners. Filler layer 1070 may be a buttress material that is an organic or synthetic tissue used to reinforce tissue at a staple line. An example of a suitable material includes SEAMGUARD® from W.L. Gore & Associates, Inc.

Filler layer 1070 is a generally triangular structure that tapers from a maximum height near knife channel 1030 towards a minimum height near outer walls 1014. Thus, the gap defined between tissue contacting surface 320 and filler layer 1070 is at a minimum near knife channel 1030 and at a maximum near outer walls 1014. As such, the amount of pressure applied to layers of tissue captured between tissue contacting surface 320 and filler layer 1070 is at a minimum near knife channel 1030 and at a maximum near outer walls 1014, thereby providing the attendant advantages as in previous embodiments with respect to forming the surgical fasteners and minimizing trauma to the layers of tissue. In addition, filler layer 1070 may be formed from a resilient or semi-resilient material, thereby further minimizing trauma to the layers of tissue that are captured between tissue contacting surface 320 and surface 1020.

Alternatively, a second filler layer 1070, shown in phantom, may be positioned on tissue contacting surface 320. Staple cartridge 1010 may include filler layer 1070 disposed on tissue contacting surface 1020, on tissue contacting surface 320, or on both tissue contacting surfaces 320, 1020 according to the surgical procedure to be performed.

In FIG. 19B, operative tool 1006b includes previously described staple cartridge 1010 in cooperation with anvil member 308'. Anvil member 308' includes tissue contacting surface 320' having tapered surfaces 322' and 324'. Surfaces 322' and 324' are connected to outer walls of anvil member 308' while extending inwards (i.e. towards the centerline of staple cartridge 1010) and downwards (i.e. towards tissue contacting surface 1020) thereby defining an angle. It is envisioned that the angle defined by tapered surfaces 322' and 324' will be substantially similar to the angle defined by filler layer 1070, but in an opposed direction forming a generally V-shaped configuration. Thus, compressive forces applied to the layers of tissue will be further reduced thereby further reducing the trauma to layers of tissue disposed between tissue contacting surface 320' and filler layer 1070. The maximum pressure applied to the layers of tissue will exist in the region near knife channel 1030 while pressures applied to the layers of tissue will decrease uniformly towards outer walls 1014. Formation and location of surgical fasteners 125a-c is substantially similar to that of the embodiment of FIG. 19A along with the attendant advantages.

Figure 20A:
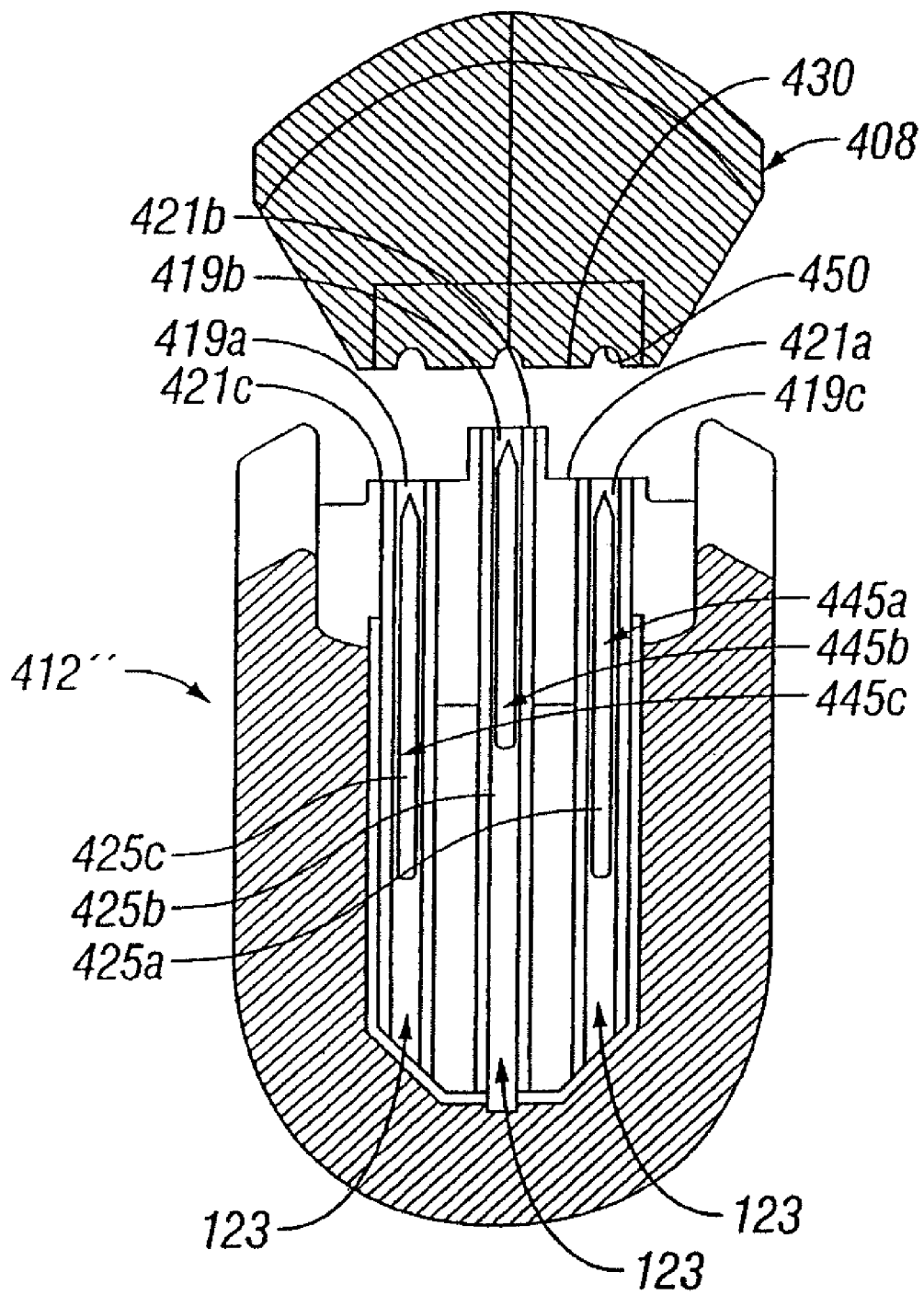
FIG. 20A is a cross-sectional end view of another embodiment of the staple cartridge of FIG. 7A.

Turning now to FIG. 20A, an alternate embodiment of staple cartridge 412' (FIG. 7A) is illustrated and described hereinafter. Staple cartridge 412" is similar to staple cartridge 412' wherein the same or similar components are renumbered accordingly and the differences discussed in detail hereinafter. Staple cartridge 412" includes a plurality of tissue contacting surfaces 421a-c, wherein each tissue contacting surface is a generally planar structure. Of the three surfaces, tissue contacting surface 421b has the greatest height and is vertically spaced apart from tissue contacting surfaces 421a and 421c. Tissue contacting surfaces 421a-c are substantially parallel with one another, wherein tissue contacting surface 421b does not lie in the same plane as either of tissue contacting surfaces 421a or 421c.

Anvil member 408 includes pockets 450 and tissue contacting surface 430. Pockets 450 substantially align with retention slots 123 for forming completed surgical fasteners. In this configuration, a minimum gap is defined between tissue contacting surface 430 and tissue contacting surface 421b while a maximum gap is defined between tissue contacting surface 430 and tissue contacting surfaces 421a and 421c. Surgical fasteners 425a-c are associated with tissue contacting surfaces 421a-c respectively. Surgical fasteners 425a-c are substantially similar to surgical fasteners 125a-c and the differences between them are discussed in detail hereinafter. In one embodiment, surgical fasteners 425a and 425c are substantially identical and have a greater leg length than surgical fastener 425b. By providing this arrangement of tissue contacting surfaces and surgical fasteners, reduced compressive forces are applied to the layers of tissue disposed between tissue contacting surface 430 and tissue contacting surfaces 421a, 421c as was discussed previously with respect to other embodiments of the presently disclosed staple cartridge.

Figure 20B:
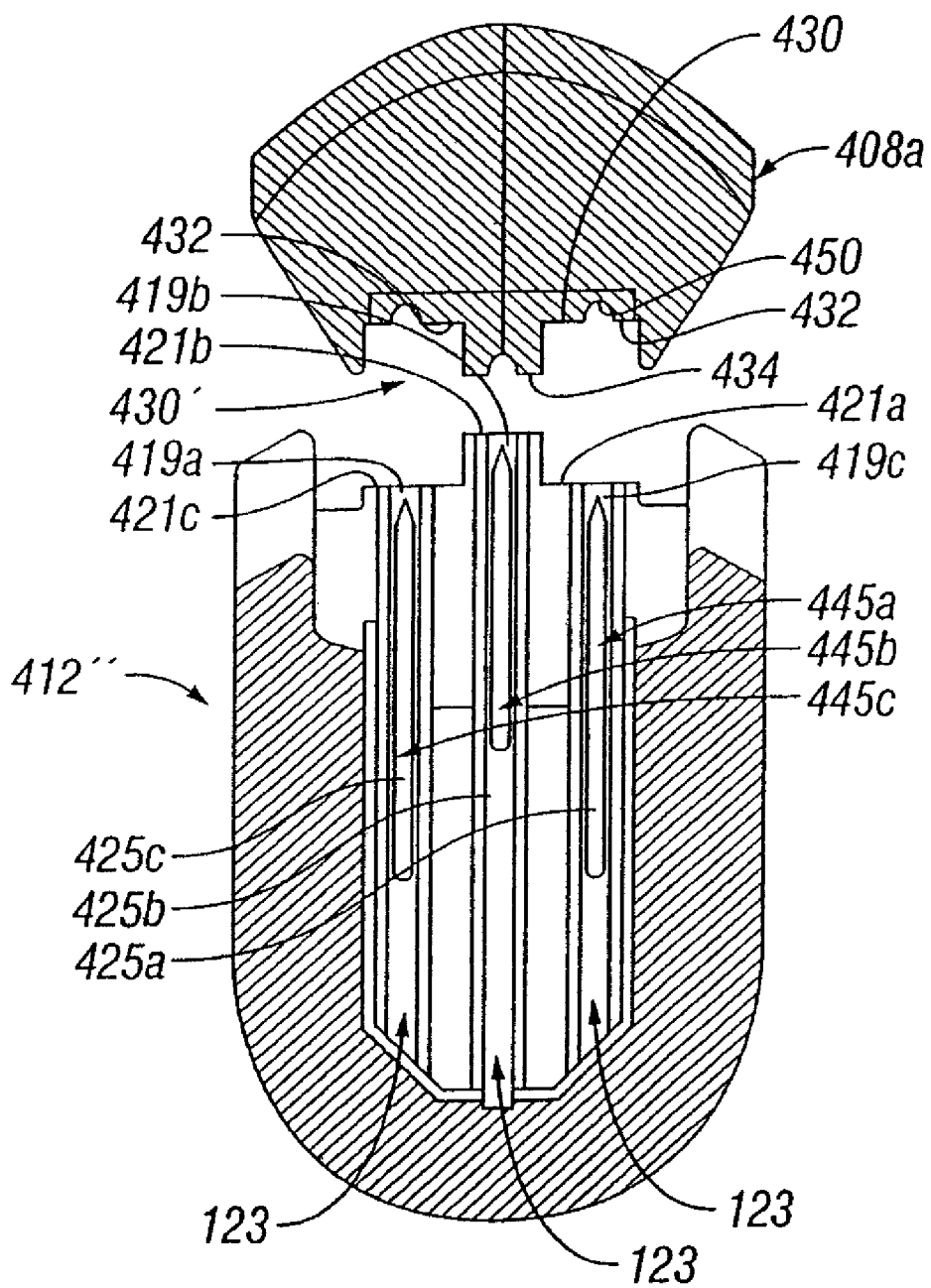
FIG. 20B is a cross-sectional end view of an alternate embodiment of an anvil member and the staple cartridge of FIG. 20A.

In the alternative, staple cartridge 412" may be used in cooperation with anvil member 408a as illustrated in FIG. 20B. Anvil member 408a includes pockets 450 and tissue contacting surface 430'. Further still, tissue contacting surface 430' includes surfaces 432 and 434. Each of surfaces 432, 434 are generally planar surfaces that are substantially parallel to tissue contacting surfaces 421a-c of staple cartridge 412". Surfaces 432 are vertically spaced apart from surface 434 such that the gap defined between surface 434 and tissue contacting surface 421b is a minimum while the gap defined between surfaces 432 and tissue contacting surfaces 421a, 421c is a maximum. Thus, reduced compressive forces are applied to the layers of tissue disposed between tissue contacting surfaces 421a, 421c and surfaces 432 of anvil member 408a.

Figure 20C:
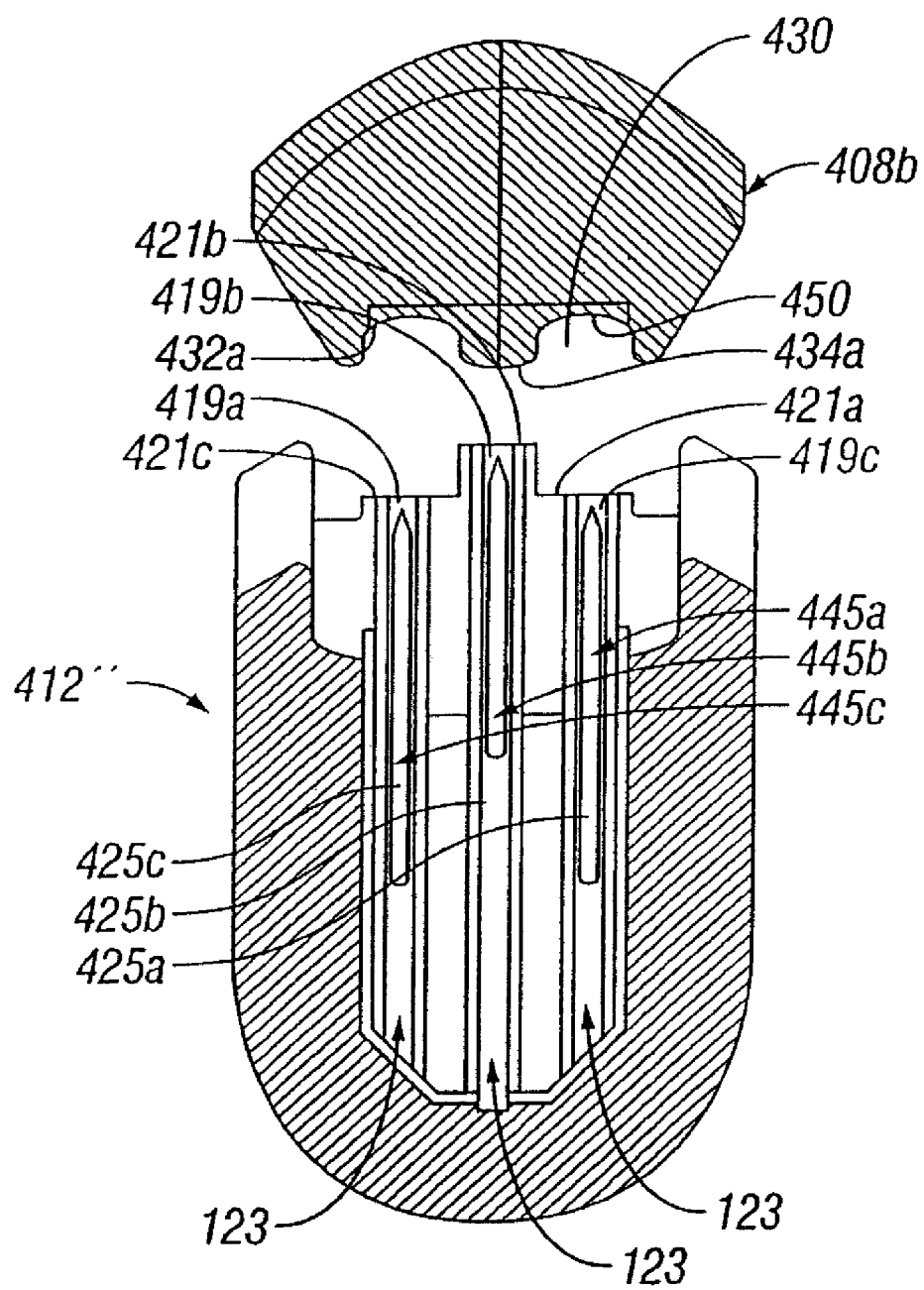
FIG. 20C is a further embodiment of an anvil member and the staple cartridge of FIG. 20B.

Alternatively, staple cartridge 412" may be used in cooperation with anvil member 408b as illustrated in FIG. 20C.

Anvil member 408*b* includes surfaces 432*a* and 434*a*. In contrast to surfaces 432 and 434 of anvil member 408*a* (FIG. 20B), surfaces 432*a* and 434*a* are generally arcuate. In this configuration, any potential trauma to tissue positioned between anvil member 408*b* and staple cartridge 412" is reduced while maintaining the advantages and benefits of an increased gap between tissue contacting surfaces of anvil member 408*b* and staple cartridge 412".

Figure 21A:
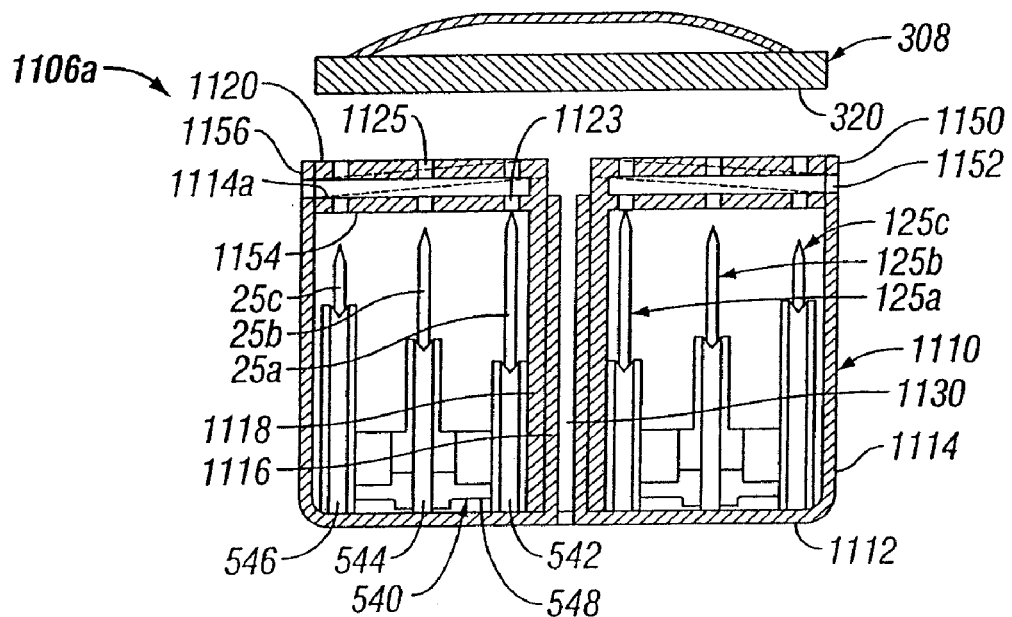
FIG. 21A is a cross-sectional end view of another embodiment of the staple cartridge of FIG. 8.

A further embodiment of the presently disclosed operative tool is illustrated in FIG. 21A and generally designated as 1106. Operative tool 1106 includes staple cartridge 1110 and anvil member 308. Anvil member 308 was previously described in detail with reference to FIG. 9. Staple cartridge 1110 includes the same or substantially similar components to staple cartridge 510 (FIG. 9), wherein the same or similar components are renumbered accordingly and the differences discussed in detail hereinafter.

In particular, staple cartridge 1110 includes surgical fasteners 125*a-c* and corresponding pushers 1140. In addition, staple cartridge 1110 includes outer walls 1114, inner walls 1116, and vertical members 1118. Inner walls 1116 may be spaced apart for defining a knife channel 1130 therebetween. In addition, vertical members 1118 are generally planar structures that abut inner walls 1116 and generally have a height at least equal to that of inner walls 1116. A top plate 1154 is a generally planar structure that connects inner wall 1116 and outer wall 1114. In one embodiment, top plate 1154 is substantially parallel to bottom surface 1112. In addition, top plate 1154 includes a plurality of retention slots 1123. Vertically spaced above top plate 1154 is cross member 1150.

Cross member 1150 includes a plurality of openings 1125 that are aligned with retention slots 1123 of top plate 1154. In addition, cross member 1150 defines a tissue contacting surface 1120 that is substantially parallel to bottom surface 1112 in a first position. Specifically, an inner edge of cross member 1150 is flexibly attached to an edge of vertical member 1118 while an outer edge 1156 is spaced apart from a top edge 1114*a* of outer wall 1114 defining a gap 1152 therebetween. Cross member 1150 has sufficient rigidity such that when layers of tissue are positioned between tissue contacting surfaces 320 and 1120, cross member 1150 maintains its substantially parallel relationship to bottom surface 1112. Gap 1152 may include an elastomeric compression member that controls the amount of deflection by tissue contacting surface 1120.

As anvil member 308 and staple cartridge 1110 are brought into a closer cooperative arrangement (i.e. during approximation and/or formation of the surgical fasteners), compressive forces generated by the relative movement between anvil member 308 and staple cartridge 1110 urge outer edge 1156 towards top edge 1114*a*, thereby reducing gap 1152. In addition, cross member 1154 (shown in phantom) flexes towards bottom wall 1112, thereby providing an increased distance between tissue contacting surfaces 320 and 1120 at outer wall 1114 while maintaining a fixed (i.e. unflexed) distance between tissue contacting surfaces 320 and 1120 at vertical member 1118. As cross member 1154 flexes, the distance between tissue contacting surfaces 320 and 1120 increases along an axis that is transverse to a longitudinal axis of staple cartridge 1110. The distance between tissue contacting surfaces 320 and 1120 at any selected position along the transverse axis is related to the amount of flexion provided by cross member 1154. Cross member 1150 is positionable throughout a plurality of positions including at least a first position that is substantially parallel to bottom surface 1112 and a second position wherein outer edge 1156 is in contact with top edge 1114*a*.

When tissue contacting surface 320 of anvil member 308 is repositioned proximate to tissue contacting surface 1120 of staple cartridge 1110, the amount of pressure applied to the layers of tissue disposed therebetween varies along a plane that is transverse to the longitudinal axis of staple cartridge 1110. Since tissue contacting surface 1120 slopes toward outer walls 1114, the pressure applied to the layers of tissue disposed between tissue contacting surfaces 320 and 1120 decreases from inner wall 1116 to outer wall 1114. Further still, when cross member 1150 flexes towards top plate 1154, it defines a curvate surface similar to tissue contacting surface 520 (FIG. 9). Openings 1125 have a greater width dimension such that when cross member 1150 is urged towards top plate 1154, the alignment of openings 1125 and retention slots 1123 is such that an unobstructed path is defined for surgical fasteners 125*a-c*, thereby allowing surgical fasteners 125*a-c* to engage layers of tissue and contact anvil member 308.

By flexing tissue contacting surface 1120 downwards from the centerline of staple cartridge 1110, reduced compressive forces are applied to the layers of tissue disposed between tissue contacting surfaces 320 and 1120 thereby minimizing trauma to the layers of tissue disposed therebetween. Therefore, layers of tissue disposed between tissue contacting surfaces 320 and 1120 will have a minimum thickness nearest knife channel 1130 (i.e. nearest the centerline of staple cartridge 1110) and gradually increasing to a maximum thickness nearest outer walls 1114.

Leg lengths of surgical fasteners 125*c*, 125*b*, and 125*a* increase in a direction moving from inner walls 1116 towards outer walls 1114. By providing surgical fasteners having increasing leg lengths along a plane that is orthogonal to inner walls 1116, the completed (i.e. formed) surgical fasteners join increasing thicknesses of tissue without unduly traumatizing the joined layers of tissue.

Figure 21B:
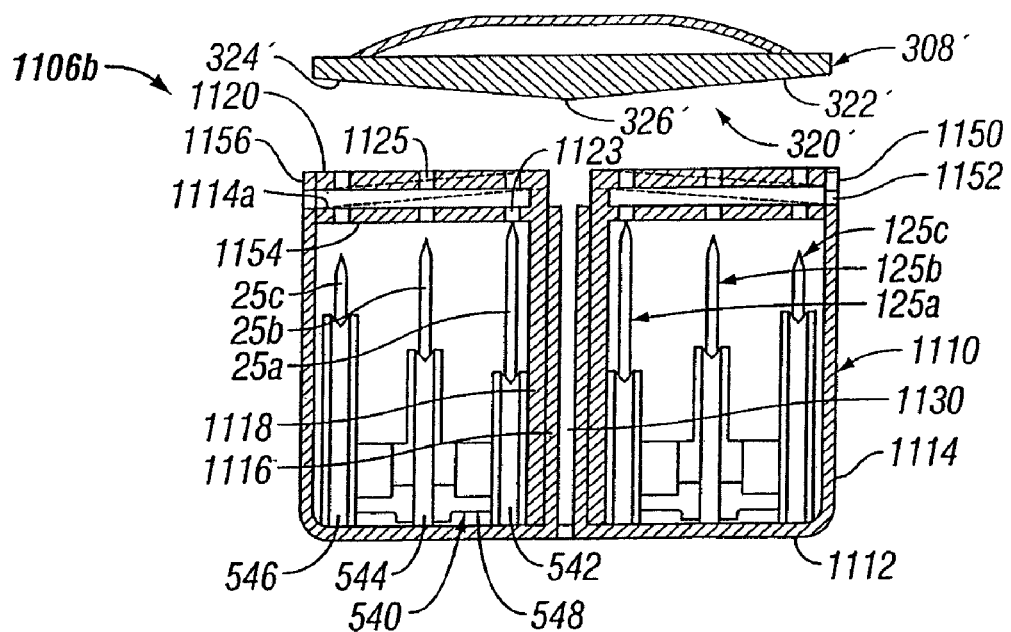
FIG. 21B is another embodiment of an anvil member and the staple cartridge of FIG. 21B.

Referring now to FIG. 21B, an alternate embodiment of the presently disclosed operative tool is illustrated and referenced as 1106*a*. Operative tool 1106*a* includes staple cartridge 1110, as discussed above, in cooperation with anvil member 308' that was discussed in detail with reference to FIG. 11. Anvil member 308' includes tissue contacting surface 320' having tapered surfaces 322' and 324'. It is envisioned that the angle defined by tapered surfaces 322' and 324' will be substantially similar to the angle defined by tissue contacting surface 1120, but in an opposed direction forming a generally V-shaped configuration. Thus, compressive forces applied to the layers of tissue will be further reduced thereby further reducing the trauma to layers of tissue disposed between tissue contacting surfaces 1120 and 320'. As in the previous embodiments, the maximum pressure applied to the layers of tissue will exist in the region near knife channel 1130 while pressures applied to the layers of tissue will decrease uniformly towards outer walls 1114. Formation and location of surgical fasteners 125*a-c* is substantially similar to that of the embodiment of FIG. 21A along with the attendant advantages.

Figure 22A:
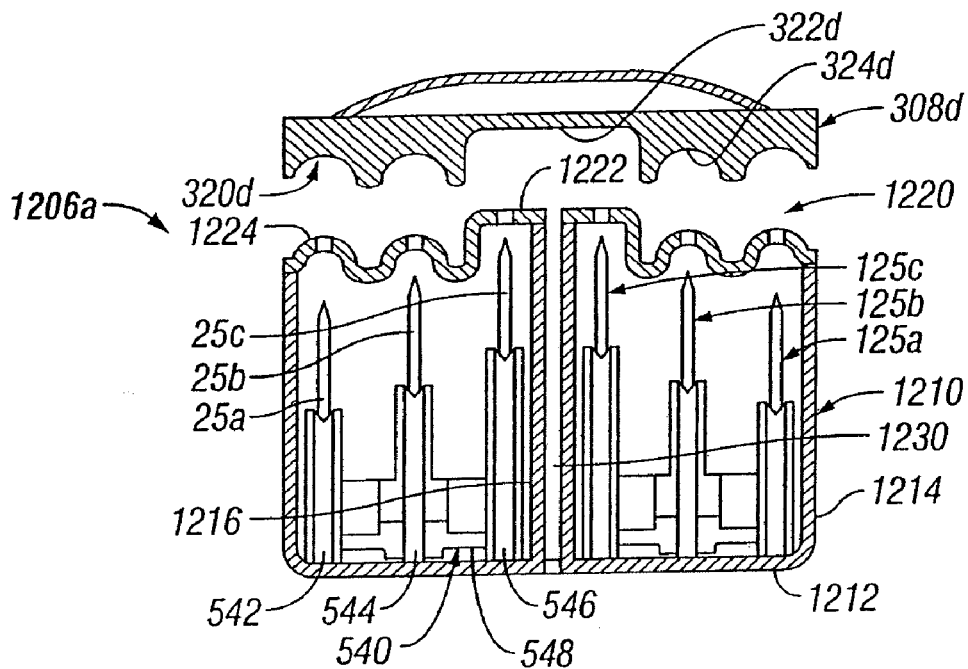
FIG. 22A is a cross-sectional end view of a further embodiment of the staple cartridge of FIG. 8 and a further embodiment of an anvil member.
Figure 22B:
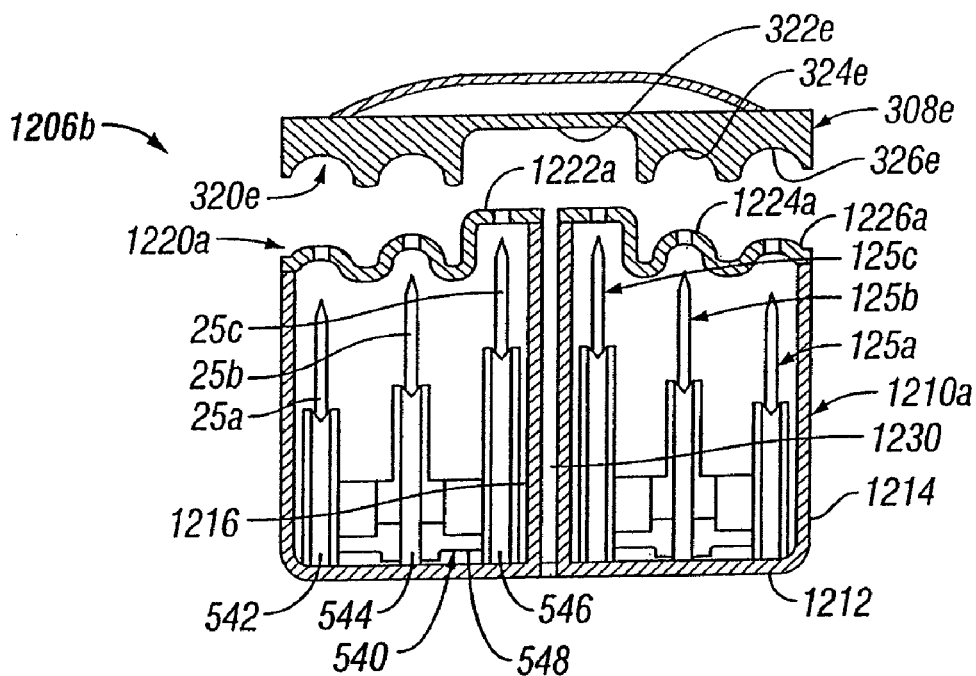
FIG. 22B is an alternate embodiment of the staple cartridge and the anvil member of FIG. 22A.
Figure 22C:
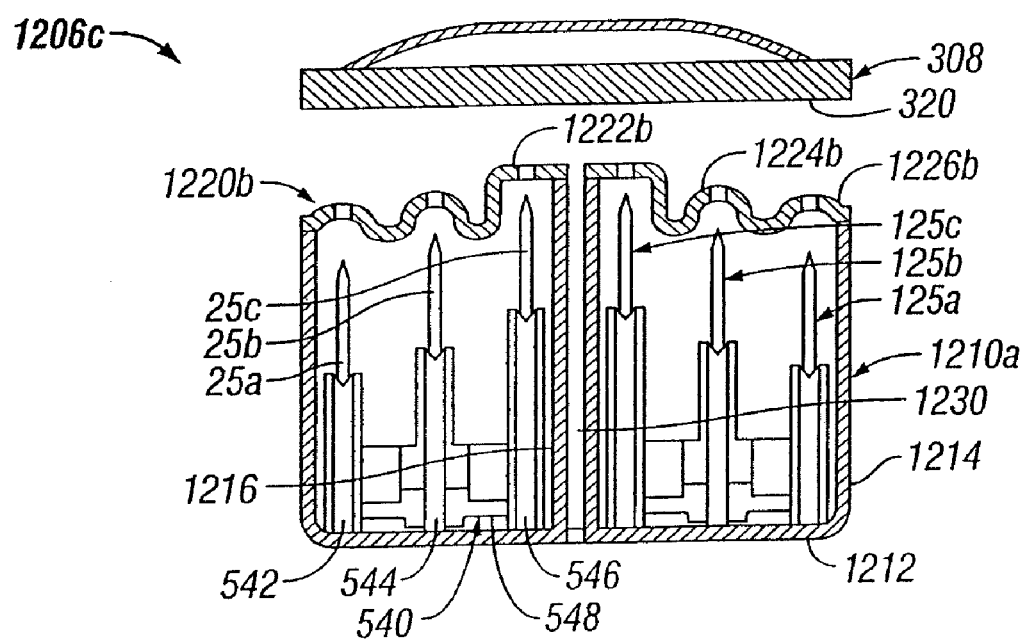
FIG. 22C is a further embodiment of an anvil member with the staple cartridge of FIG. 22B.
Figure 23:
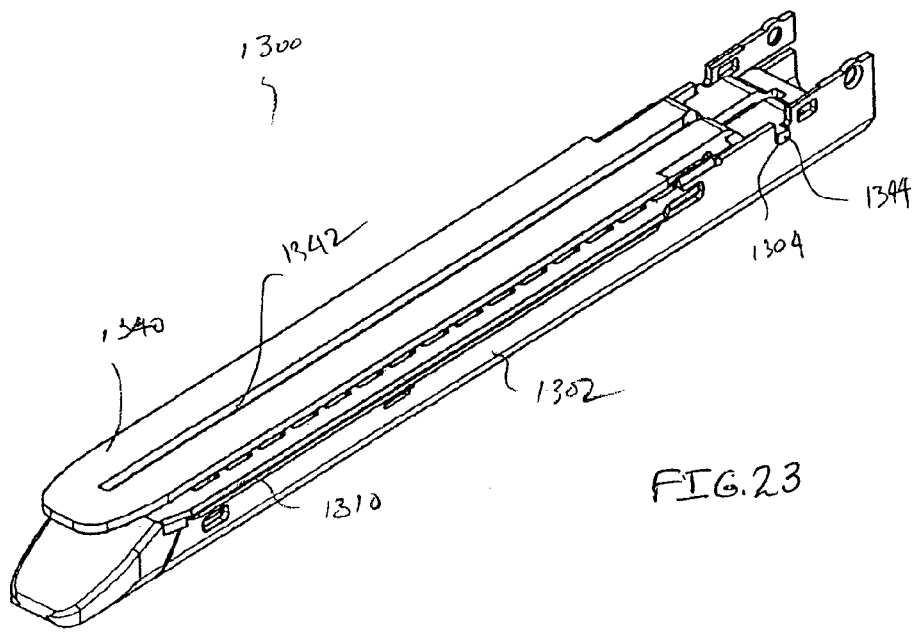
FIG. 23 is a perspective view of another embodiment of the presently disclosed operative tool illustrating a staple cartridge and an anvil member in an approximated position.

Further embodiments are illustrated in FIGS. 22A-C and discussed hereinbelow. Referring initially to FIG. 22A, operative tool 1206*a* is illustrated and includes anvil member 308*d* and staple cartridge 1210. In particular, staple cartridge 1210 includes surgical fasteners 125*a-c* and fastener ejection members 540 that were previously discussed in detail with respect to FIG. 9A. Similar to previous embodiments, staple cartridge 1210 includes a bottom surface 1212, outer walls 1214, inner walls 1216, and a knife channel 1230. In addition, staple cartridge 1210 includes a tissue contacting surface 1220 formed from surfaces 1222 and 1224. Each of surfaces 1222 and 1224 has a width dimension that is sufficient to accommodate at least one row of surgical fasteners. As shown in FIG. 22A, surface 1222 is substantially parallel to bottom surface 1212, while surface 1224 is a generally arcuate structure. Further still, the topmost portions of surfaces 1224 have substantially the same height dimension as measured from bottom surface 1212. A complementary anvil member 308d is provided in operative tool 1206a wherein anvil member 308d includes a substantially planar surface 322d that corresponds to surfaces 1222 and knife channel 1230. Additionally, anvil member 308d includes surfaces 324d that are generally arcuate so as to correspond to surfaces 1224 of staple cartridge 1210. By providing this arrangement between staple cartridge 1210 and anvil member 308d, a substantially uniform tissue gap is defined between the surfaces of anvil member 308d and staple cartridge 1210.

Alternatively, operative tool 1206b, as shown in FIG. 22B, includes anvil member 308e in cooperation with staple cartridge 1210a. Staple cartridge 1210a is substantially similar to staple cartridge 1210 (FIG. 22A) with the differences therebetween discussed below. Most notably, tissue contacting surface 1220a includes surfaces 1222a, 1224a, and 1226a. Surfaces 1222a and 1224a are substantially similar to surfaces 1222 and 1224 of FIG. 22A, while surface 1226 is a generally arcuate structure having a lower height dimension that surface 1224 (i.e. with respect to bottom surface 1212). Thus, surfaces 1222, 1224, and 1226 "step down" from the centerline towards outer walls 1214 of staple cartridge 1210a. Anvil member 308e has a tissue contacting surface 320e that substantially complements tissue contacting surface 1220a. As such, tissue contacting surface 320e includes a substantially planar surface 322e that corresponds to surfaces 1222a and knife channel 1230. Additionally, anvil member 308d includes surfaces 324e and 326e that are generally arcuate so as to correspond to surfaces 1224a and 1226a of staple cartridge 1210a. By providing this arrangement between staple cartridge 1210a and anvil member 308e, a substantially uniform tissue gap is defined between the surfaces of anvil member 308e and staple cartridge 1210a.

Alternatively, staple cartridge 1210a may be used in cooperation with anvil member 308 as shown in FIG. 22C. In this configuration, the gap defined between tissue contacting surfaces 320 and 1220b increases from a first gap at knife channel 1230 to a second gap at outer walls 1214, wherein the second gap is greater than the first gap.

In a further embodiment of the present disclosure, an operative tool assembly is illustrated in FIGS. 23-30 and generally referenced as 1300. As in the previously disclosed embodiments, operative tool assembly 1300 includes a staple cartridge 1310 and an anvil member 1340. Tool assembly 1300 includes a body 1302 for receiving staple cartridge 1310.

Anvil member 1340 optionally includes a slot 1342 in tissue contacting surface 1306. Tissue contacting surface 1306 includes staple forming depressions. A pair of tabs 1344 is located in a proximal portion of anvil member 1340 and cooperates with recesses 1304 of body 1302. As such, anvil member 1340 is pivotably coupled to body 1302 and is repositionable between an open position and an approximate position. In the open position, anvil member 1340 is spaced apart from staple cartridge 1310 and allows tissue to be positioned therebetween. In the approximated position, anvil member 1340 cooperates with staple cartridge 1310 and captures tissue therebetween. Slot 1342 is configured for allowing the passage of a knife blade (not shown) as the knife blade passes longitudinally through anvil member 1340 and staple cartridge 1310. In certain embodiments, the knife blade is carried on, or integrally formed with, a drive beam (not shown) that is advanced distally through anvil member 1340 and staple cartridge 1310 for approximating anvil cartridge 1340 and staple cartridge 1310 with respect to one another, and to deploy staples from staple cartridge 1310 against anvil member 1340. Operative tool assembly 1300 may be arranged as described in U.S. Pat. No. 5,865,361, the disclosure of which is hereby incorporated by reference herein in its entirety. In other embodiments, anvil member 1340 and staple cartridge 1310 are approximated with respect to one another by the advancement distally of a clamp tube, such as disclosed in U.S. Pat. No. 5,318,221, the disclosure of which is hereby incorporated by reference herein in its entirety.

Figure 24:
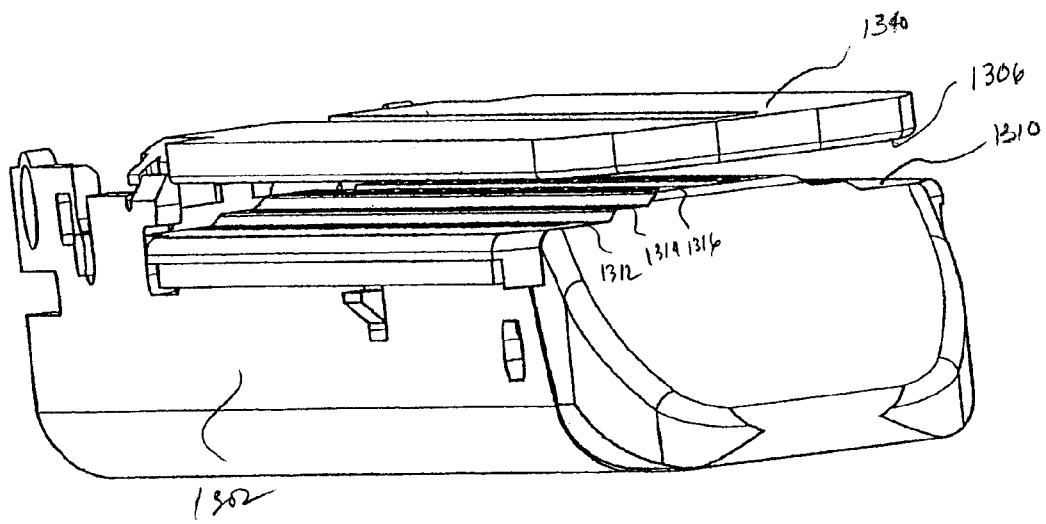
FIG. 24 is an enlarged perspective view of the operative tool of FIG. 23 illustrating the relationship between tissue contacting surfaces of the staple cartridge.
Figure 29:
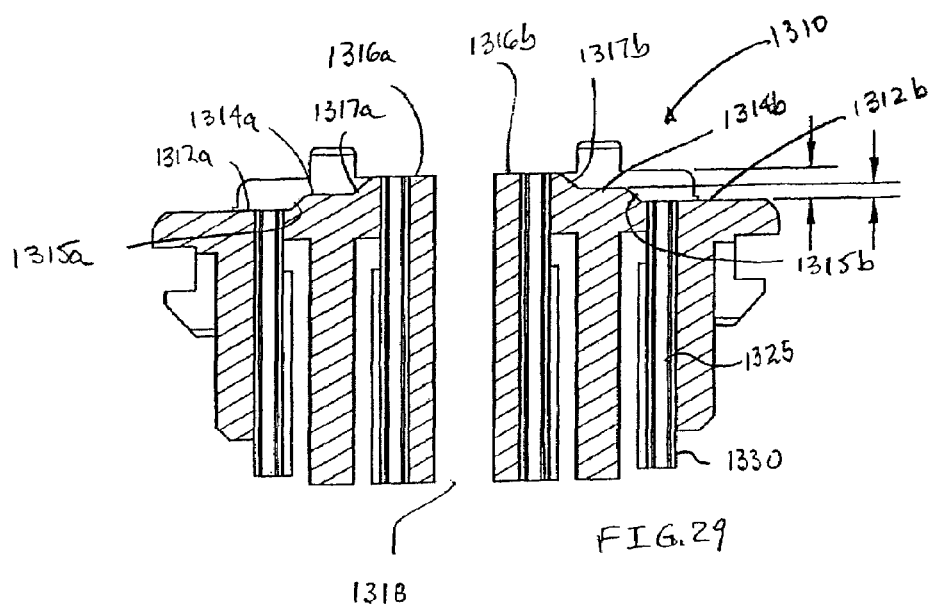
FIG. 29 is a front cross-sectional view of the cartridge of FIG. 27 taken along section line 29-29.
Figure 30:
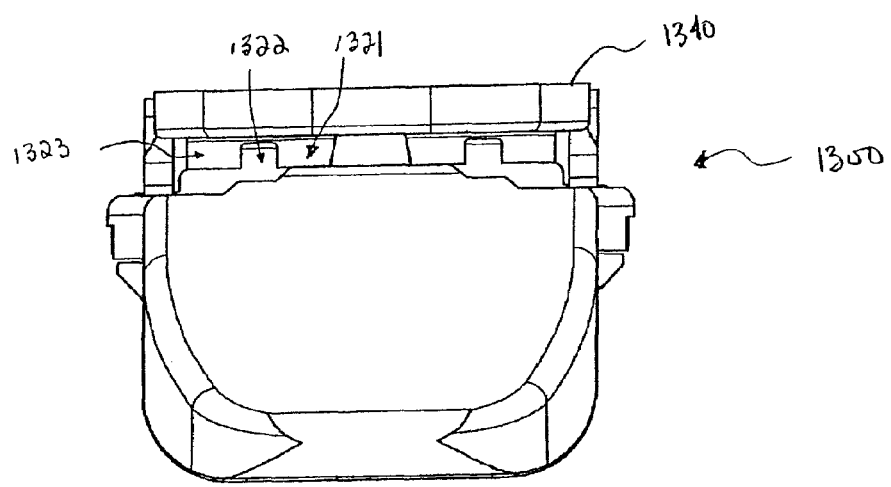
FIG. 30 is a front elevational view of the operative tool of FIG. 27.

Staple cartridge 1310 includes a plurality of tissue contacting surfaces. In one embodiment, staple cartridge 1310 includes tissue contacting surfaces 1312, 1314, and 1316. Tissue contacting surfaces 1312, 1314, and 1316 are substantially planar surfaces that are substantially parallel to the other tissue contacting surfaces, but are spaced apart (i.e. the tissue contacting surfaces are in a stepped configuration) as seen in FIGS. 24 and 29. Referring also to FIG. 29, a wall surface 1315 extends between tissue contacting surfaces 1312 and 1314, while a wall surface 1317 extends between tissue contacting surfaces 1314 and 1316. Wall surfaces 1315, 1317 are generally planar surfaces that define an angle with respect to an adjacent tissue contacting surface. As illustrated in FIG. 29, wall surfaces 1315, 1317 are arranged such that each of the wall surfaces is in an angular relationship with the adjacent tissue contacting surfaces 1312, 1314, and 1316. The angle defined between the wall surface and the adjacent tissue contacting surface may be in a range of angles that is greater than 0° to about 90°.

Providing tissue contacting surfaces 1312, 1314, and 1316 in a stepped configuration (FIG. 29), improves the anastomotic strength and the degree of hemostasis obtained at the cut line when layers of body tissue are clamped between anvil member 1340 and staple cartridge 1310. In particular, this arrangement provides gradual tissue loading or compression due to the varying gap defined between tissue contacting surface 1306 of anvil member 1340 and tissue contacting surfaces 1312, 1314, 1316 of staple cartridge 1310 when they are in the approximated position, thereby minimizing tissue trauma while maintaining a relatively high degree of hemostasis and anastomotic strength. Notably, when anvil member 1340 and staple cartridge 1310 are in the approximated position, first, second, and third tissue gaps are defined between tissue contacting surfaces 1312, 1314, 1316 and a tissue contacting surface 1306 of anvil member 1340. As such, the first tissue gap 1321 is the smallest, while the third tissue gap 1323 is the greatest with the second tissue gap 1322 in-between the first and third tissue gaps. It is envisioned that the tissue contacting surface 1306 of anvil member 1340 includes a plurality of depressions for forming completed surgical fasteners.

Figure 25:
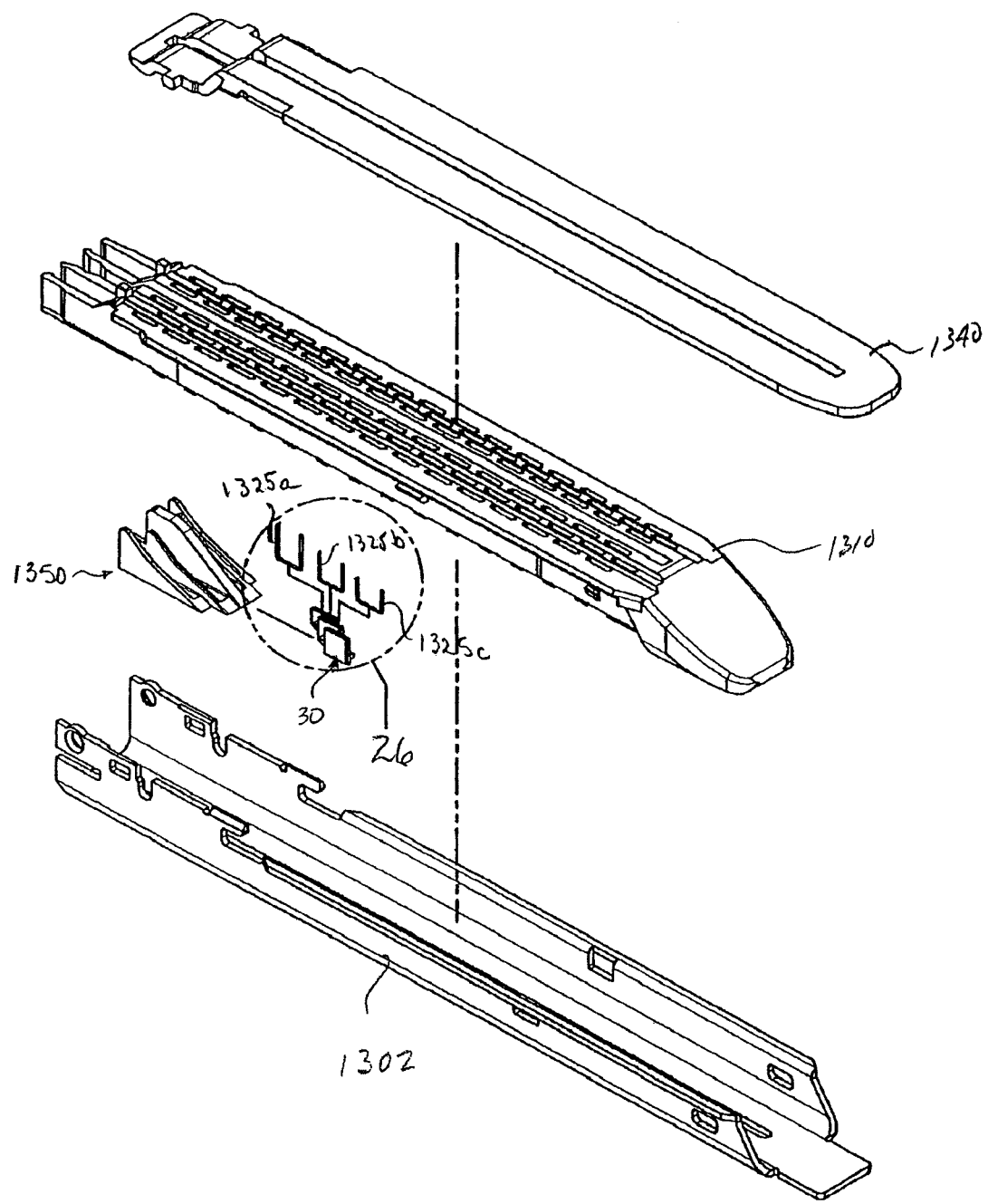
FIG. 25 is an exploded view of the operative tool showing a number of staples, a staple pusher, and a sled.
Figure 26:
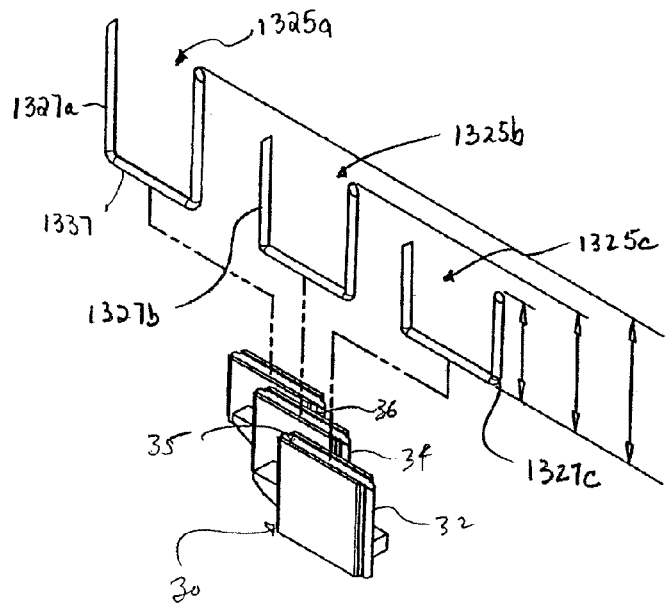
FIG. 26 is an enlarged perspective view of the section of detail in FIG. 25 illustrating the leg lengths of the staples.
Figure 27:
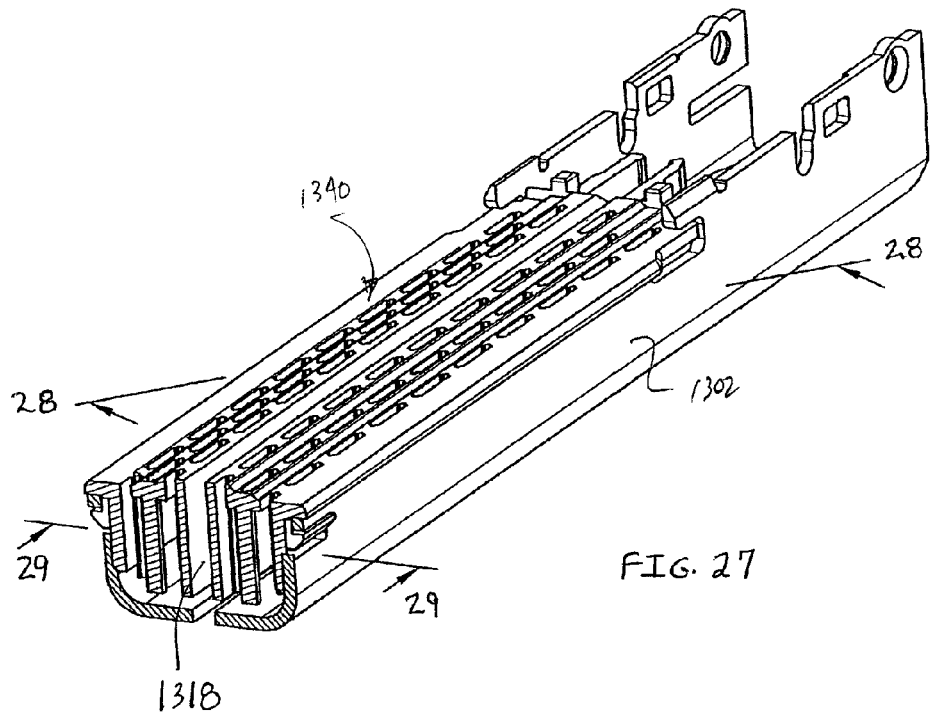
FIG. 27 is a perspective cross-sectional view of the operative tool of FIG. 23 with the anvil member removed.
Figure 28:
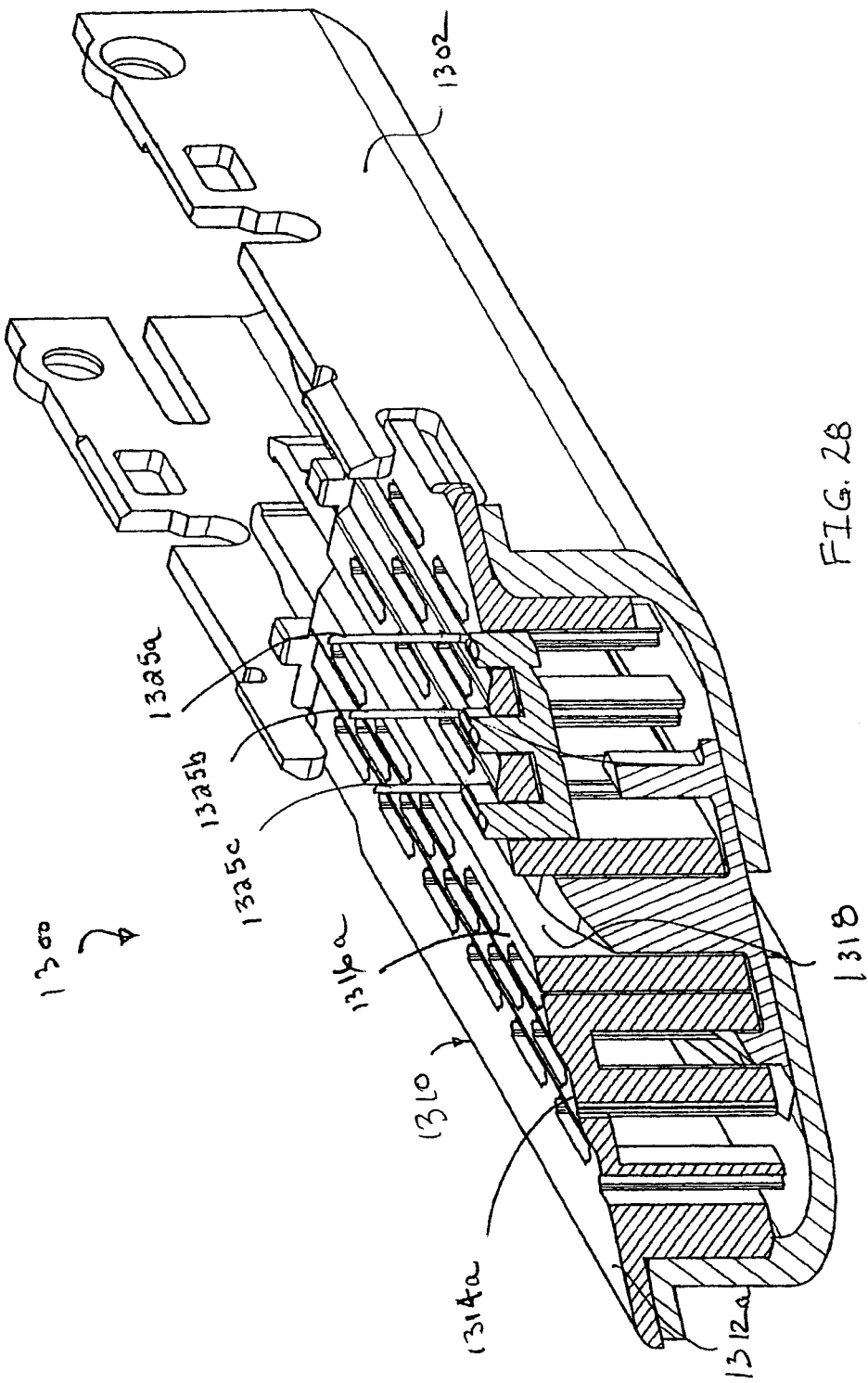
FIG. 28 is a cross-sectional view of the cartridge of FIG. 27 including staples having different leg lengths taken along section line 28-28.

Staple cartridge 1310 includes a plurality of surgical fasteners disposed in retention slots 1330 that are open at tissue contacting surfaces 1312, 1314, 1316. Referring now to FIGS. 25 and 26, the arrangement of the surgical fasteners is illustrated. Staple cartridge 1310 includes surgical fasteners or staples 1325a, 1325b, and 1325c. Staples 1325a, 1325b, and 1325c are substantially similar to staples 25a, 25b, and 25c that were previously discussed. Staples 1325a, 1325b, and 1325c each include a backspan 1337. Briefly, legs 1327a of surgical fasteners 1325a have a first leg length, legs 1327b of surgical fasteners 1325b have a second leg length, and legs 1327c of surgical fasteners 1325c have a third leg length. In one embodiment, legs 1327c of surgical fasteners 1325c have a leg length of about 3.0 mm, legs 1327b of surgical fasteners 1325b have a leg length of about 3.5 mm, and legs 1327a of surgical fasteners 1325a have a leg length of about 4.0 mm. It is contemplated that other embodiments of the present disclosure include legs 1327c in a range of about 2.0 mm to about 4.0 mm, legs 1327b in a range of about 2.5 mm to about 4.5 mm, and legs 1327a in a range of about 3.0 mm to about 5.0 mm. In certain preferred embodiments, surgical fasteners 1325a have the longest leg length, surgical fasteners 1325c have the shortest leg length, and surgical fasteners 1325b have a leg length therebetween. It is contemplated that the staples in the staple cartridge 1310 can range from about 2.0 mm to about 5.0 mm. Surgical fasteners 1325a are arranged in a longitudinally extending row located in tissue contacting surface 1312; surgical fasteners 1325b are arranged in a longitudinally extending row located in tissue contacting surface 1314; and surgical fasteners 1325c are arranged in a longitudinally extending row located in tissue contacting surface 1316. In this arrangement, layers of body tissue that are fastened using staple cartridge 1310 have improved hemostasis and anastomotic strength. It is envisioned and within the scope of the present disclosure that any number of arrangements are possible.

Surgical fasteners 1325a-c cooperate with staple pusher 30 (FIG. 26) and sled 1350 (FIG. 25) such that the longitudinal translation of sled 1350 by a drive beam through staple cartridge 1310 urges pushers 30 in a vertical direction to eject surgical fasteners 1325a-c. As shown in FIG. 26, staple pusher 30 includes pusher plates 32, 34, and 36, each of which has a different vertical dimension. Pusher plate 32 has the greatest vertical dimension and cooperates with surgical fastener 1325c, while pusher plate 36 has the smallest vertical dimension and cooperates with surgical fastener 1325a. Pusher plate 34 has a vertical dimension greater than pusher plate 36, but less than pusher plate 32 and cooperates with surgical fastener 1325b. By providing surgical fasteners 1325a-c and pusher plates 30 with complementary heights, tips of surgical fasteners 1325a-c are substantially flush with their respective tissue contacting surfaces prior to ejecting surgical fasteners 1325a-c from their respective retention slots. It is also envisioned that other arrangements of pusher plates and surgical fasteners may be used. For example, the pusher plates may have heights that are selected to define a gap with the tissue contacting surface 1306 for forming a staple having a leg length of a particular size.

As illustrated in FIG. 25, staple cartridge 1310 fits into cartridge body 1302. In one embodiment, staple cartridge 1310 is replaceable. After the user has fired the staples in staple cartridge 1310, the user removes staple cartridge 1310 from cartridge body 1302 and installs a new staple cartridge 1310 having a full complement of staples. In an alternate embodiment, staple cartridge 1310 is fixedly attached to cartridge body 1302. In such an embodiment, operative tool assembly 1300 including anvil member 1340, body 1302, and staple cartridge 1310 may constitute a replaceable loading unit so that upon the installation of a new loading unit, a new knife blade is also provided. Staple cartridge 1310 may also include a knife channel 1318 to allow passage of a knife blade and drive beam.

Figure 31:
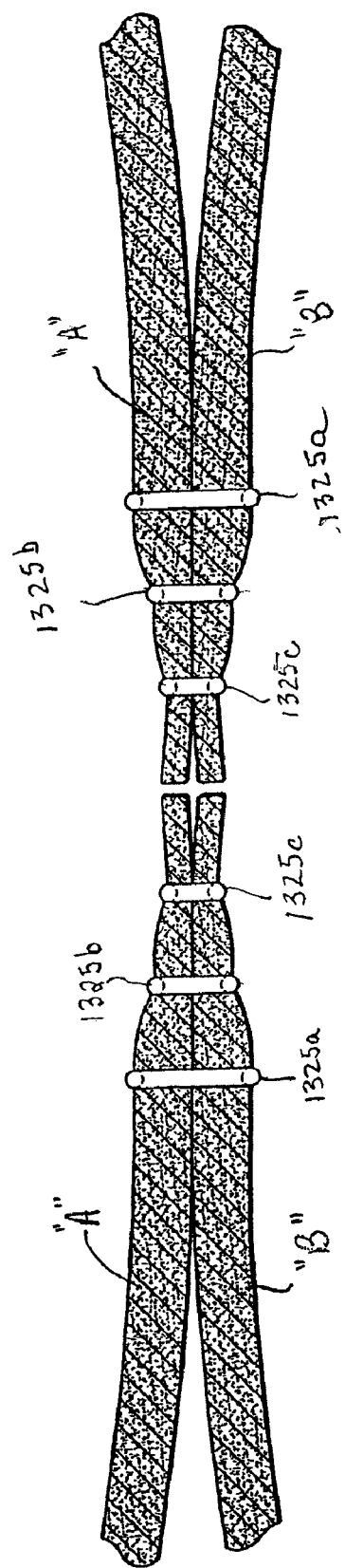
FIG. 31 is a cross-sectional side elevational view of a tissue interface following the firing of operative tool shown in FIGS. 23-30.

In a certain embodiments, the staples are arranged in the staple cartridge 1310 so that staples 1325a are disposed in retention slots 1330 (FIG. 29) that extend in a linear row, along tissue contacting surface 1312. Staples 1325b are disposed in retention slots 1330 that extend in a linear row, along tissue contacting surface 1314. Staples 1325a have leg lengths that are longer than the leg lengths of staples 1325b and are disposed further away from the knife channel 1318, as compared to staples 1325b. In the embodiment shown in FIGS. 23-31, the staple cartridge 1310 further has staples 1325c, which have leg lengths that are shorter than the leg lengths of staples 1325a and 1325b, and are disposed adjacent the knife channel 1318. As shown in FIG. 31, when the staples are deployed and formed in tissue, the smaller staples 1325c are disposed adjacent the cut line in the tissue, with the intermediate-sized staples 1325b being adjacent to staples 1325c and outwardly from staples 1325c with respect to the cut line. Staples 1325a, which are the largest staples, are disposed outwardly of the staples 1325b and 1325c. This arrangement provides improved hemostasis in the tissue.

In a surgical stapling instrument such as surgical stapling instrument 300 (FIG. 5) or surgical stapling instrument 200 (FIG. 4), two linear rows of each size staple are provided, on opposite sides of the knife channel 1318. As seen in FIG. 29, the staple cartridge 1310 has outer tissue contacting surfaces 1312a and 1312b. Retention slots 1330 housing staples 1325a are defined in the outer tissue contacting surfaces 1312a and 1312b. Retention slots 1330 housing staples 1325b are defined in the intermediate tissue contacting surfaces 1314a and 1314b. Retention slots 1330 housing staples 1325c are defined in the inner tissue contacting surfaces 1316a and 1316b. Wall surface 1315a provides a sloping surface extending generally from the tissue contacting surfaces 1312a to tissue contacting surface 1314a. A wall surface 1315b is arranged similarly on the opposite side of the knife channel 1318, as shown in FIG. 29. Wall surface 1317a extends generally between tissue contacting surfaces 1314a and 1316a and a similar wall surface 1317b is provided on the opposite side of the knife channel 1318. The sloping wall surfaces 1315a, 1315b, 1317a and 1317b provide a gradually varying compressive force on the tissue when the surgical stapling instrument is used. When tissue is clamped between anvil member 1340 and staple cartridge 1310, fluid within the tissue flows generally outwardly and the sloping wall surfaces facilitate this process.

In tool assemblies according to the present disclosure, staples having different leg lengths may be arranged so that the staples with the larger leg lengths are arranged adjacent the knife channel. In addition, the staple cartridge may have a single planar tissue contacting surface and the anvil member may be provided with more than one tissue contacting surface so as to define more than one gap with respect to the tissue contacting surface of the staple cartridge. One or both of the staple cartridge and anvil member may have stepped surfaces, angled or sloped surfaces, or curved surfaces that are selected to correspond to staples having predetermined leg lengths. In certain embodiments, more than one tissue contacting surface is provided, on the staple cartridge, the anvil member, or both, with sloped surfaces extending therebetween. In certain embodiments, the staple pushers have heights corresponding to the different staple sizes.

Referring additionally to FIG. 31, following the firing of surgical stapling instrument 1300, the resulting tissue interface is seen in cross-section. Accordingly, some or all of surgical fasteners 1325a-1325c serve to hold tissues "A" and "B" to one another while the surgical fasteners also provide the hemostasis.

All of the presently disclosed embodiments of the surgical stapling instrument provide a variable pressure gradient (i.e. load profile) to the layers of tissue that are joined together with the surgical fasteners. Therefore, the layers of tissue that are proximate to the center of the surgical stapling instrument (i.e. center of the staple cartridge) are subjected to higher compressive forces (i.e. loads), thereby forming thinner layers of tissue as compared to layers of tissue that are further away from the center of the surgical stapling instrument.

Since the layers of tissue nearest the center of the surgical stapling instrument can be compressed more, a smaller sized surgical staple or fastener can be used to mechanically suture (i.e. fasten) the transected layers of tissue. Further still, providing a gradual compression gradient to the layers of tissue to be joined (see FIG. 16B), may result in a higher degree of hemostasis. Due to the contoured shape of the staple cartridge, the layers of tissue can be compressed more at the center of the surgical stapling instrument, because the layers of tissue can translate (i.e. move) from a region of relatively high pressure (i.e. at the center) to a region of relatively low pressure (i.e. at the edges) as the anvil member is moved relative to the staple cartridge, thereby defining the pressure gradient.

In a further embodiment, the staple cartridge 1410 is as shown above in FIGS. 23-31, except that the wall surfaces 1417a and 1417b are convex, non-planar surfaces. (See FIG. 32). It is contemplated that any of the wall surfaces 1415a, 1417a, 1415b and 1417b are non-planar and may be concave or convex. The tissue contacting surfaces 1412a, 1414a, 1416a, 1412a, 1414a, and/or 1416a may also be planar or non-planar.

Figure 32:
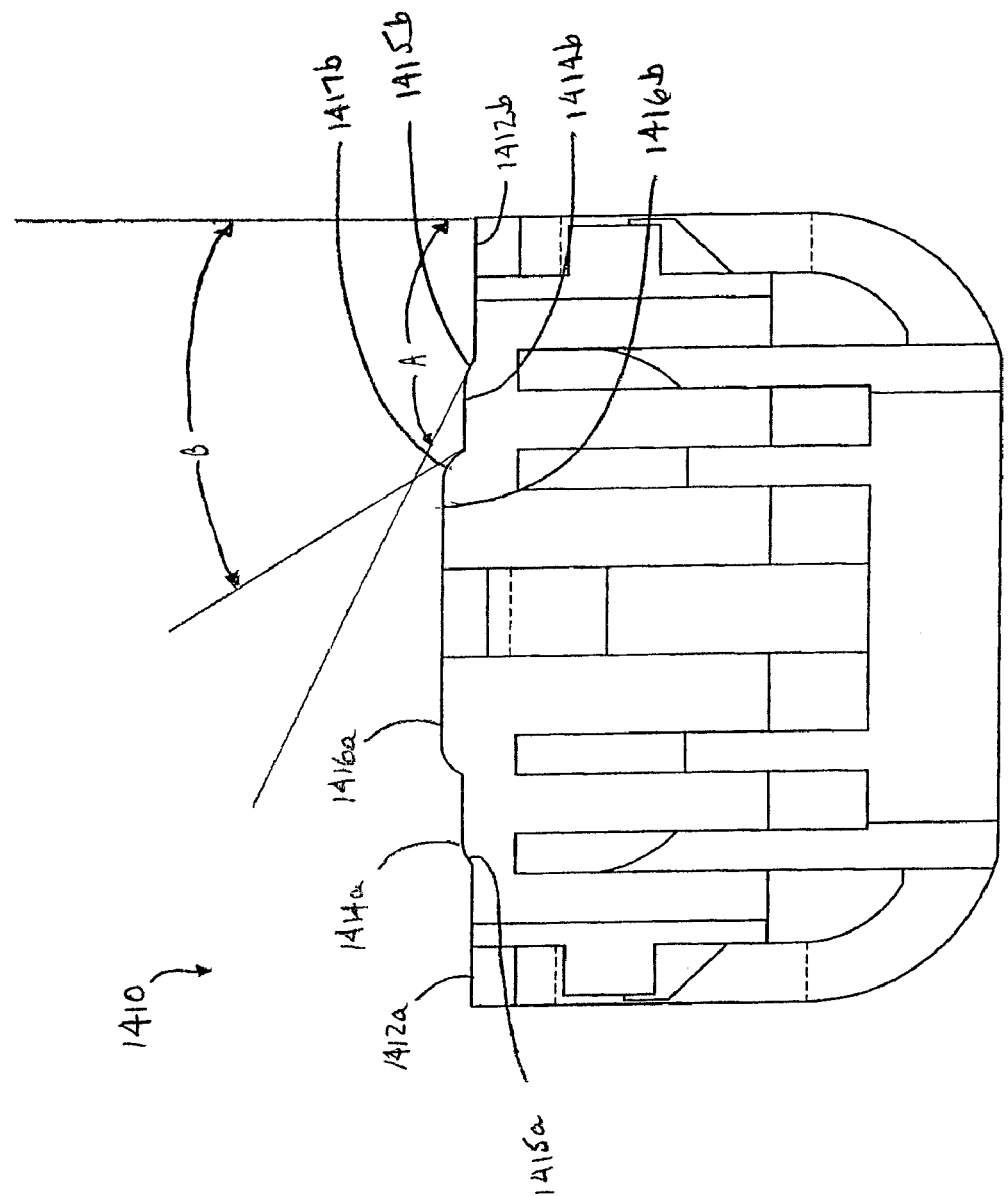
FIG. 32 is front cross-sectional view of an alternate embodiment of the cartridge shown in FIG. 29.

FIG. 32 also shows an angle A between wall surface 1315b and a reference line, which is shown as a vertical line, as well as an angle B between wall surface 1317b and the reference line. Angle A is desirably greater than angle B. In one preferred embodiment, angle A is about 63 degrees and angle B is about 42 degrees.

In addition, while each of the surgical stapling instruments described above and shown herein include tissue contacting surfaces having a stepped profile, it is envisioned that any of the surgical stapling instruments disclosed herein can have tissue contacting surfaces having any one of a number of profiles including and not limited to angles, conical, tapered, arcuate and the like, as disclosed in commonly assigned U.S. patent application Ser. No. 10/411,686, filed on May 11, 2003, entitled "Surgical Stapling Apparatus Including an Anvil and Cartridge Each Having Cooperating Mating Surfaces," currently assigned to Tyco Healthcare Group LP, the entire contents of which is incorporated herein by reference.

It will be understood that various modifications may be made to the embodiments of the presently disclosed surgical stapling instruments. Therefore, the above description should not be construed as limiting, but merely as exemplifications of embodiments. Those skilled in the art will envision other modifications within the scope and spirit of the present disclosure.

What is claimed is:

1. A surgical instrument comprising:
a cartridge having first and second rows of retention slots and fasteners disposed in the first and second rows of retention slots, each fastener having a pair of legs, wherein at least one fastener in the first row of retention slots has a first leg length and at least one fastener in the second row of retention slots has a second leg length that is different from the first leg length;
an anvil member having first and second surfaces;
a first gap defined between the first surface and the cartridge; and
a second gap defined between the second surface and the cartridge, wherein the first gap is different from the second gap.

2. The surgical instrument of claim 1, wherein the first row of retention slots is located adjacent a knife channel and the first leg length is less than the second leg length.

3. The surgical instrument of claim 2, wherein the first gap is proximate to a knife channel and the first gap is less than the second gap.

4. The surgical instrument of claim 1, wherein the first surface defines a first plane and the second surface defines a second plane, the first plane being substantially parallel to the second plane and spaced apart therefrom.

5. The surgical instrument of claim 1, wherein the first surface defines a first plane and the second surface defines a second plane such that an angle is defined between the first and second planes.

6. The surgical instrument of claim 1, wherein at least one of the first surface and the second surface is curved.

7. The surgical instrument of claim 1, wherein at least one of the first surface and the second surface is planar.

8. The surgical instrument of claim 1, wherein the cartridge defines a knife channel, the first row of retention slots and the second row of retention slots are disposed on a first side of the knife channel, and further comprising a third row of retention slots and a fourth row of retention slots, the third row of retention slots and the fourth row of retention slots being disposed on a second side of the knife channel, wherein the first row of retention slots is located adjacent the knife channel and the first leg length is less than the second leg length.

9. The surgical instrument of claim 8, further comprising fasteners in the third row of retention slots and in the fourth row of retention slots, wherein at least one of the fasteners in the third row of fasteners is located adjacent the knife channel and has a third leg length and at least one of the fasteners in the fourth row of fasteners has a fourth leg length.

10. The surgical instrument of claim 9, wherein the third leg length is less than the fourth leg length.

11. The surgical instrument of claim 1, wherein the first row of retention slots is longitudinally extending and the second row of retention slots is longitudinally extending.

12. A surgical instrument comprising:
a cartridge having an outer wall, a central longitudinal axis, first and second rows of retention slots, and fasteners disposed in the first and second rows of retention slots, the cartridge defining a first surface, each fastener having a pair of legs, wherein at least one fastener in the first row of retention slots has a first leg length and at least one fastener in the second row of retention slots has a second leg length that is different from the first leg length;
an anvil member having a second surface, the second surface having a configuration selected from the group consisting of curved and angled; and
a gap defined between the first surface of the cartridge and the second surface of the anvil, wherein the gap varies between the central longitudinal axis of the cartridge and the outer wall of the cartridge.

13. The surgical instrument of claim 12, wherein the gap is at a minimum along the central longitudinal axis.

14. The surgical instrument of claim 13, wherein the first row of fasteners is disposed adjacent the central longitudinal axis and the first leg length is less than the second leg length.

15. The surgical instrument of claim 12, wherein the cartridge defines a knife channel, the first row of retention slots and the second row of retention slots are disposed on a first side of the knife channel, and further comprising a third row of retention slots and a fourth row of retention slots, the third row of retention slots and the fourth row of retention slots being disposed on a second side of the knife channel, wherein the first row of retention slots is located adjacent the knife channel and the first leg length is less than the second leg length.

16. The surgical instrument of claim 15, further comprising fasteners in the third row of retention slots and in the fourth row of retention slots, wherein at least one of the fasteners in the third row of fasteners is located adjacent the knife channel and has a third leg length and at least one of the fasteners in the fourth row of fasteners has a fourth leg length.

17. The surgical instrument of claim 16, wherein the third leg length is less than the fourth leg length.

18. The surgical instrument of claim 12, wherein the first row of retention slots is longitudinally extending and the second row of retention slots is longitudinally extending.

19. A surgical instrument comprising:
a cartridge having first and second rows of retention slots and fasteners disposed in the first and second rows of retention slots, each fastener having a pair of legs, wherein at least one fastener in the first row of retention slots has a first leg length and at least one fastener in the second row of retention slots has a second leg length that is different from the first leg length, the cartridge having a first surface and a second surface, at least one of the first surface and the second surface being selected from the group consisting of a planar surface and a curved surface;
an anvil member;
a first gap defined between the first surface and the anvil member; and
a second gap defined between the second surface and the anvil member, wherein the first gap is different from the second gap.

20. The surgical instrument of claim 19, wherein the first row of retention slots is located adjacent a knife channel and the first leg length is less than the second leg length.

21. The surgical instrument of claim 20, wherein the first gap is proximate to a knife channel and the first gap is less than the second gap.

22. The surgical instrument of claim 19, wherein the first surface defines a first plane and the second surface defines a second plane, the first plane being substantially parallel to the second plane and spaced apart therefrom.

23. The surgical instrument of claim 19, wherein the first surface defines a first plane and the second surface defines a second plane such that an angle is defined between the first and second planes.

24. The surgical instrument of claim 19, wherein the cartridge defines a knife channel, the first row of retention slots and the second row of retention slots are disposed on a first side of the knife channel, and further comprising a third row of retention slots and a fourth row of retention slots, the third row of retention slots and the fourth row of retention slots being disposed on a second side of the knife channel, wherein the first row of retention slots is located adjacent the knife channel and the first leg length is less than the second leg length.

25. The surgical instrument of claim 24, further comprising fasteners in the third row of retention slots and in the fourth row of retention slots, wherein at least one of the fasteners in the third row of fasteners is located adjacent the knife channel and has a third leg length and at least one of the fasteners in the fourth row of fasteners has a fourth leg length.

26. The surgical instrument of claim 25, wherein the third leg length is less than the fourth leg length.

27. A surgical instrument comprising:
a cartridge having an outer wall, a central longitudinal axis, first and second rows of retention slots, and fasteners disposed in the first and second rows of retention slots, the cartridge defining a first surface, each fastener having a pair of legs, wherein at least one fastener in the first row of retention slots has a first leg length and at least one fastener in the second row of retention slots has a second leg length that is different from the first leg length, the first surface having a configuration selected from the group consisting of curved and angled;
an anvil member having a second surface; and
a gap defined between the first surface of the cartridge and the second surface of the anvil, wherein the gap varies between the central longitudinal axis of the cartridge and the outer wall of the cartridge.

28. The surgical instrument of claim 27, wherein the gap is at a minimum along the central longitudinal axis.

29. The surgical instrument of claim 28, wherein the first row of fasteners is disposed adjacent the central longitudinal axis and the first leg length is less than the second leg length.

30. The surgical instrument of claim 29, further comprising fasteners in the third row of retention slots and in the fourth row of retention slots, wherein at least one of the fasteners in the third row of fasteners is located adjacent the knife channel and has a third leg length and at least one of the fasteners in the fourth row of fasteners has a fourth leg length.

31. The surgical instrument of claim 30, wherein the third leg length is less than the fourth leg length.

32. The surgical instrument of claim 27, wherein the cartridge defines a knife channel, the first row of retention slots and the second row of retention slots are disposed on a first side of the knife channel, and further comprising a third row of retention slots and a fourth row of retention slots, the third row of retention slots and the fourth row of retention slots being disposed on a second side of the knife channel, wherein the first row of retention slots is located adjacent the knife channel and the first leg length is less than the second leg length.

33. A surgical instrument comprising:
a cartridge having first and second rows of retention slots and fasteners disposed in the first and second rows of retention slots, each fastener having a pair of legs, wherein at least one fastener in the first row of retention slots has a first leg length and at least one fastener in the second row of retention slots has a second leg length that is different from the first leg length;
an anvil member having first and second surfaces, the first surface being generally arcuate and the second surface being generally arcuate;
a first gap defined between the first surface and the cartridge; and a second gap defined between the second surface and the cartridge, wherein the first gap is different from the second gap.

34. The surgical instrument of claim 33, wherein the first row of retention slots is located adjacent a knife channel and the first leg length is less than the second leg length.

35. The surgical instrument of claim 34, wherein the first gap is proximate to a knife channel and the first gap is less than the second gap.

36. The surgical instrument of claim 33, wherein the second surface has a lower height than the first surface.

37. The surgical instrument of claim 33, wherein the cartridge defines a knife channel, the first row of retention slots and the second row of retention slots are disposed on a first side of the knife channel, and further comprising a third row of retention slots and a fourth row of retention slots, the third row of retention slots and the fourth row of retention slots being disposed on a second side of the knife channel.

38. The surgical instrument of claim 37, wherein the anvil has a third surface and a fourth surface, the third surface being generally arcuate and the fourth surface being generally arcuate.

39. The surgical instrument of claim 38, further comprising fasteners in the third row of retention slots and fasteners in the fourth row of retention slots, wherein at least one of the fasteners in the third row of fasteners is located adjacent the knife channel and has a third leg length and at least one of the fasteners in the fourth row of fasteners has a fourth leg length.

40. The surgical instrument of claim 39, wherein the first leg length is less than the second leg length and the third leg length is less than the fourth leg length.

41. A surgical instrument comprising:
a cartridge having first and second rows of retention slots and fasteners disposed in the first and second rows of retention slots, each fastener having a pair of legs, wherein at least one fastener in the first row of retention slots has a first leg length and at least one fastener in the second row of retention slots has a second leg length that is different from the first leg length, the cartridge having a first surface and a second surface, the first surface being generally arcuate and the second surface being generally arcuate;
an anvil member;
a first gap defined between the first surface and the anvil member; and
a second gap defined between the second surface and the anvil member, wherein the first gap is different from the second gap.

42. The surgical instrument of claim 41, wherein the first row of retention slots is located adjacent a knife channel and the first leg length is less than the second leg length.

43. The surgical instrument of claim 42, wherein the first gap is proximate to a knife channel and the first gap is less than the second gap.

44. The surgical instrument of claim 41, wherein the second surface has a lower height than the first surface.

45. The surgical instrument of claim 41, wherein the cartridge defines a knife channel, the first row of retention slots and the second row of retention slots are disposed on a first side of the knife channel, and further comprising a third row of retention slots and a fourth row of retention slots, the third row of retention slots and the fourth row of retention slots being disposed on a second side of the knife channel.

46. The surgical instrument of claim 45, wherein the cartridge has a third surface and a fourth surface, the third surface being generally arcuate and the fourth surface being generally arcuate.

47. The surgical instrument of claim 46, further comprising fasteners in the third row of retention slots and fasteners in the fourth row of retention slots, wherein at least one of the fasteners in the third row of fasteners is located adjacent the knife channel and has a third leg length and at least one of the fasteners in the fourth row of fasteners has a fourth leg length.

48. The surgical instrument of claim 47, wherein the first leg length is less than the second leg length and the third leg length is less than the fourth leg length.

* * * * *